US010562910B2

(12) United States Patent
Wang et al.

(10) Patent No.: US 10,562,910 B2
(45) Date of Patent: *Feb. 18, 2020

(54) NITROGEN-CONTAINING TRICYCLIC COMPOUNDS AND USES THEREOF IN MEDICINE

(71) Applicant: SUNSHINE LAKE PHARMA CO., LTD., Dongguan, Guangdong (CN)

(72) Inventors: Xiaojun Wang, Dongguan (CN); Xinye Yang, Dongguan (CN); Junwen Wu, Dongguan (CN); Shaohui Xiong, Dongguan (CN); Shengqiang Pan, Dongguan (CN); Shengtian Cao, Dongguan (CN); Yingjun Zhang, Dongguan (CN)

(73) Assignee: NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 0 days.

This patent is subject to a terminal disclaimer.

(21) Appl. No.: 16/322,945

(22) PCT Filed: Aug. 2, 2017

(86) PCT No.: PCT/CN2017/095724
§ 371 (c)(1),
(2) Date: Feb. 2, 2019

(87) PCT Pub. No.: WO2018/024224
PCT Pub. Date: Feb. 8, 2018

(65) Prior Publication Data
US 2019/0169203 A1 Jun. 6, 2019

(30) Foreign Application Priority Data
Aug. 5, 2016 (CN) .......................... 2016 1 0640043

(51) Int. Cl.
C07D 491/044 (2006.01)
C07D 491/056 (2006.01)
A61K 31/4164 (2006.01)
A61P 9/04 (2006.01)
A61K 31/4353 (2006.01)
A61P 15/00 (2006.01)
A61P 5/50 (2006.01)
A61P 9/12 (2006.01)
A61P 7/02 (2006.01)
A61P 9/10 (2006.01)
A61K 31/42 (2006.01)
C07D 491/107 (2006.01)

(52) U.S. Cl.
CPC ...... C07D 491/044 (2013.01); A61K 31/4164 (2013.01); A61K 31/42 (2013.01); A61K 31/4353 (2013.01); A61P 5/50 (2018.01); A61P 7/02 (2018.01); A61P 9/04 (2018.01); A61P 9/10 (2018.01); A61P 9/12 (2018.01); A61P 15/00 (2018.01); C07D 491/056 (2013.01); C07D 491/107 (2013.01)

(58) Field of Classification Search
CPC ............ C07D 491/044; C07D 491/056; C07D 491/107; A61P 5/50; A61P 7/02; A61P 9/10; A61P 9/12; A61P 9/04; A61P 15/00; A61K 31/4164; A61K 31/42; A61K 31/4353
USPC .......................................................... 546/89
See application file for complete search history.

(56) References Cited

U.S. PATENT DOCUMENTS

| | | | |
|---|---|---|---|
| 6,602,898 B1 | 8/2003 | Jinno et al. |
| 6,639,078 B1 | 10/2003 | Haffner et al. |
| 6,700,013 B2 | 3/2004 | Jinno et al. |
| 6,974,830 B2 | 12/2005 | Bauer et al. |
| 6,984,650 B2 | 1/2006 | Haffner et al. |
| 7,034,046 B2 | 4/2006 | Bauer et al. |
| 7,098,336 B2 | 8/2006 | Bauer et al. |
| 7,319,109 B2 | 1/2008 | Boggs et al. |
| 7,410,997 B2 | 8/2008 | Jinno et al. |
| 7,705,028 B2 | 4/2010 | Caldwell et al. |
| 7,863,302 B2 | 1/2011 | Bell et al. |
| 7,960,552 B2 | 6/2011 | Bass, III et al. |
| 8,106,077 B2 | 1/2012 | Bell et al. |
| 8,153,624 B2 | 4/2012 | Genin et al. |

(Continued)

FOREIGN PATENT DOCUMENTS

| | | |
|---|---|---|
| CN | 104045635 A | 9/2014 |
| CN | 104513213 A | 4/2015 |

(Continued)

OTHER PUBLICATIONS

Ali; Ann Transl Med 2015, 3, 5. DOI: 10.3978/j.issn.2305-5839.2014.12.06 (Year: 2015).*

(Continued)

Primary Examiner — Daniel R Carcanague
(74) Attorney, Agent, or Firm — Kam Wah Law

(57) ABSTRACT

A nitrogen-containing tricyclic compound which acts as modulator of FXR, or a stereoisomer, a geometric isomer, a tautomer, an N-oxide, a hydrate, a solvate, a metabolite, a pharmaceutically acceptable salt or a prodrug thereof, and the use of the compound for the treatment of disease and/or condition mediated by FXR are described. And a pharmaceutical composition containing the compound disclosed herein and a method of treatment of disease and/or condition mediated by FXR comprising administering the compound or the pharmaceutical composition thereof are also described.

11 Claims, No Drawings

(56) References Cited

U.S. PATENT DOCUMENTS

| | | | |
|---|---|---|---|
| 8,158,665 B2 | 4/2012 | Caldwell et al. | |
| 8,193,192 B2 | 6/2012 | Kremoser et al. | |
| 8,952,042 B2 | 2/2015 | Kremoser et al. | |
| 9,139,539 B2 | 9/2015 | Kinzel et al. | |
| 9,150,568 B2 | 10/2015 | Tully et al. | |
| 9,539,244 B2 | 1/2017 | Kinzel et al. | |
| 9,751,874 B2 | 9/2017 | Gege et al. | |
| 9,820,979 B2 | 11/2017 | Kinzel et al. | |
| 9,932,332 B2 | 4/2018 | Gege | |
| 9,938,278 B2 | 4/2018 | Gege et al. | |
| 10,080,741 B2 | 9/2018 | Or et al. | |
| 10,080,742 B2 | 9/2018 | Or et al. | |
| 10,080,743 B2 | 9/2018 | Or et al. | |
| 10,183,917 B2 * | 1/2019 | Wang | C07D 249/06 |
| 2008/0096921 A1 | 4/2008 | Navas, III et al. | |
| 2010/0120775 A1 | 5/2010 | Bass, III et al. | |
| 2010/0184809 A1 | 7/2010 | Kremoser et al. | |
| 2010/0249179 A1 | 9/2010 | Deaton et al. | |
| 2011/0034507 A1 | 2/2011 | Akwabi-Ameyaw et al. | |
| 2013/0261108 A1 | 10/2013 | Tully et al. | |
| 2014/0039007 A1 | 2/2014 | Tully | |
| 2015/0366856 A1 | 12/2015 | Tully et al. | |
| 2017/0333399 A1 | 11/2017 | Or et al. | |
| 2017/0334893 A1 | 11/2017 | Or et al. | |
| 2017/0334894 A1 | 11/2017 | Or et al. | |
| 2017/0355693 A1 | 12/2017 | Blomgren et al. | |
| 2017/0368038 A1 | 12/2017 | Badman et al. | |
| 2018/0030003 A1 | 2/2018 | Wang et al. | |
| 2018/0099957 A1 | 4/2018 | Ma et al. | |
| 2018/0141941 A1 | 5/2018 | He et al. | |
| 2018/0200243 A1 | 7/2018 | Kinzel et al. | |

FOREIGN PATENT DOCUMENTS

| | | | | |
|---|---|---|---|---|
| CN | 106146483 A | 11/2016 | | |
| CN | 106632294 A | 5/2017 | | |
| CN | 107021957 A | 8/2017 | | |
| CN | 108218852 A | 6/2018 | | |
| CN | 108264506 A | 7/2018 | | |
| CN | 108341822 A | 7/2018 | | |
| CN | 107021958 A | 8/2018 | | |
| JP | 2007230909 A | 9/2007 | | |
| WO | WO2009149795 A3 | 2/2010 | | |
| WO | WO-2016103037 A1 * | 6/2016 | | C07D 487/14 |
| WO | WO-2016127924 A1 * | 8/2016 | | C07D 249/06 |
| WO | WO-2016174616 A1 * | 11/2016 | | C07D 493/04 |
| WO | WO2017147047 A1 | 2/2017 | | |
| WO | WO2017118294 A1 | 7/2017 | | |
| WO | WO2017128896 A1 | 8/2017 | | |
| WO | WO2017133521 A1 | 8/2017 | | |
| WO | WO2018039384 A1 | 3/2018 | | |
| WO | WO2018039386 A1 | 3/2018 | | |
| WO | WO2018059314 A1 | 4/2018 | | |
| WO | WO2018075207 A1 | 4/2018 | | |
| WO | WO2018085148 A1 | 5/2018 | | |
| WO | WO2018133730 A1 | 7/2018 | | |
| WO | WO2019149158 * | 9/2019 | | C07D 491/044 |

OTHER PUBLICATIONS

Chemical Abstracts STN Registry Database Record for RN 801249-34-3, entered on Dec. 22, 2004. (Year: 2004).*

Claudel; Arterioscler Thromb Vasc Biol. 2005, 25, 2020-2031. DOI: 10.1161/01.ATV.0000178994.21828.a7 (Year: 2005).*

Mudaliar; Gastroenterology 2013, 145, 574-582. DOI: 10.1053/j.gastro.2013.05.042 (Year: 2013).*

Pellicciari; Journal of Medicinal Chemistry 2005, 48, 5383-5402. DOI: 10.1021/jm0582221 (Year: 2005).*

Zou; Arch Pharm Res 2012, 35, 2093-2104. DOI: 10.1007/s12272-012-1206-4 (Year: 2012).*

International Search Report of PCT/CN2017/095724, dated Oct. 23, 2017.

Written Opinion of PCT/CN2017/095724, dated Oct. 23, 2017.

* cited by examiner

NITROGEN-CONTAINING TRICYCLIC COMPOUNDS AND USES THEREOF IN MEDICINE

CROSS-REFERENCE TO RELATED APPLICATIONS

This is a U.S. national stage application of the International Patent Application No. PCT/CN2017/095724, filed Aug. 2, 2017, which claims priority to Chinese Patent Application No. 201610640043.5, filed Aug. 5, 2016, both of which are incorporated herein by reference in their entirety.

FIELD OF THE INVENTION

The present invention relates to nitrogen-containing tricyclic compounds which can bind to the FXR and act as FXR modulators, and pharmaceutical compositions thereof, as well as the uses of said compounds and pharmaceutical compositions in the preparation of medicaments for the treatment of diseases and/or conditions mediated by FXR.

BACKGROUND OF THE INVENTION

FXR is a member of the nuclear hormone receptor superfamily, and is mainly expressed in the liver, kidneys and intestines (Seol et al. *Mol. Endocrinol* (1995), 9:72-85; Forman Cell (1995), 81:687-693). It functions as a heterodimer with the RXR, and regulates gene transcription by binding to the response elements of the target gene promoter. The FXR-RXR heterodimer binds with highest affinity to an inverted repeat-1 (IR-1) response element, wherein consensus receptor-binding hexamers are separated by a nucleotide. FXR is activated by bile acids (cholesterol metabolism end products) (Makishima et al., *Science* (1999), 284:1362-1365; Parks et al., *Science* (1999), 284:1365-1368; Wang et al., *Mol. Cell.* (1999), 3:543-553), and the bile acid is used to inhibit cholesterol catabolism. (Urizar et al., (2000) *J. Biol. Chem.* 275:39313-393170).

FXR is a critical regulator of cholesterol homeostasis, triglyceride synthesis and adipogenesis (Crawley, Expert Opinion Ther. *Patents* (2010), 20:1047-1057). In addition to target for treating dyslipidemia, obesity, vitamin D-related diseases, intestinal diseases, drug-induced side effects as well as hepatitis (Crawley, Expert Opinion Ther. Patents (2010), 20:1047-1057), FXR is also the target of hepatic and gall disease, chronic hepatitis, nonalcoholic fatty liver disease (NAFLD), nonalcoholic steatohepatitis (NASH), cholestasis, liver fibrosis, cirrhosis of liver, hepatitis B, metabolic diseases, lipid metabolism disorders, carbohydrate metabolic diseases, cardiovascular and metabolic diseases, atherosclerosis, type II diabetes and diabetic complications (Frank G. Schaap et al., *Journal of Medicinal Chemistry*, (2005), 48:5383-5402).

Small molecule compounds which act as FXR modulators have been disclosed in the following patents: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2009/149795, WO 2008/025539, WO 2008/025540, WO 2012/087520, WO 2012/087521, WO 2012/087519, WO2013/007387 and WO 2015/036442. R. C. Buijsman et al. also reviewed more-small molecule modulators of FXR (R. C. Buijsman et al., *Curr. Med. Chem.* 2005, 12, 1017-1075).

Although the development of FXR modulators has a certain progress, the development space is still enormous.

SUMMARY OF THE INVENTION

The object of the present invention is to provide novel nitrogen-containing tricyclic compounds which act as FXR modulators. The biological activity and pharmacokinetic properties of the compounds disclosed herein are superior to these of the known FXR modulators.

The present invention provides a compound, or a pharmaceutical composition thereof, which binds to FXR and acts as modulator of FXR. The present invention further relates to said compound or the use of said compound in the preparation of a medicament for the treatment of diseases and/or conditions through said compound binding to the FXR nuclear receptor. The present invention further describes the synthetic method of the compound. The compounds of the invention exhibit improved biological activity and pharmacokinetic advantages.

Specifically, in one aspect, provided herein is a compound having formula (I), or a stereoisomer, a geometric isomer, a tautomer, an N-oxide, a hydrate, a solvate, a metabolite, a pharmaceutically acceptable salt or a prodrug thereof,

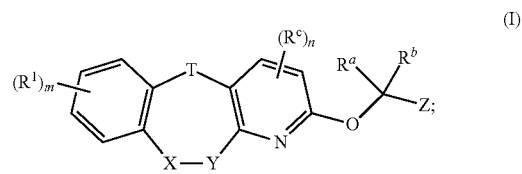

wherein:

T is —NH—, —O—, —S—, —C(═O)— or —CH$_2$—;

each of X and Y is independently a bond, —O—, —S(═O)$_t$—, —NR$^x$—, —CR$^y$R$^z$— or —C(═O)—, or —X—Y— is —CHR$^h$—CHR$^k$— or —CR$^y$═CR$^z$—;

each R$^x$ is independently hydrogen, deuterium, alkyl, aminoalkyl, haloalkyl, cycloalkyl, heterocyclyl, aryl, halosubstituted aryl or arylalkyl;

each R$^y$ and R$^z$ is independently hydrogen, deuterium, F, Cl, Br, I, hydroxy, amino, nitro, cyano, alkyl, haloalkyl, hydroxyalkyl, aminoalkyl, alkoxy, alkylamino, alkenyl, alkynyl, cycloalkyl, heterocyclyl, aryl, halo-substituted aryl or arylalkyl; or R$^y$ and R$^z$, together with the same carbon atom to which they are attached, independently and optionally form a cycloalkane ring or heterocyclic ring, and wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;

each of R$^h$ and R$^k$ is independently hydrogen, deuterium, F, Cl, Br, I, hydroxy, amino, nitro, cyano, methyl, ethyl, isopropyl or trifluoromethyl; or R$^h$ and R$^k$ together with the carbon atoms to which they are attached, form a cycloalkane ring or a heterocyclic ring, wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;

each of R$^a$ and R$^b$ is independently hydrogen, deuterium or C$_{1-3}$ alkyl;

each R$^c$ is independently hydrogen, deuterium, F, Cl, Br, I, oxo, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxymethyl, isopropoxymethyl, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—$C_{1-3}$ alkyl, —C(=O)NHS(=O)$_2$—$C_{1-3}$ alkyl, —C(=O)NHS(=O)$_2$-phenyl, —C(=O)NH—$C_{1-3}$ alkylene-S(=O)$_2$OH, —C(=O)NH—$C_{1-3}$ alkylene-C(=O)OH, —S(=O)$_2$NH$_2$, —S(=O)$_2$OH, —S(=O)$_2$—$C_{1-3}$ alkyl, —C(=O)NH$_2$ or —C(=O)N(CH$_3$)$_2$;

each $R^1$ is independently hydrogen, deuterium, F, Cl, Br, I, hydroxy, amino, nitro, cyano, alkyl, haloalkyl, hydroxyalkyl, aminoalkyl, alkoxy, alkylamino, haloalkoxy, alkoxyalkyl, alkenyl, alkynyl, cycloalkyl, cycloalkoxy, cycloalkylalkyl, heterocyclyl, heterocyclylalkyl, aryl, halo-substituted aryl, arylalkyl, heteroaryl, -$L^1$-C(=O)O$R^8$, -$L^1$-S(=O)$_t$$R^9$, —O-$L^2$-C(=O)O$R^8$, —O-$L^2$-S(=O)$_t$$R^9$, —C(=O)N$R^{10}$$R^{11}$, —C(=O)N($R^{10}$)S(=O)$_2$$R^9$, —C(=N$R^{10}$)N$R^{10}$$R^{11}$, —C(=O)N($R^{10}$)-$L^3$-S(=O)$_2$O$R^8$, —C(=O)N($R^{10}$)C(=O)O$R^8$ or —C(=O)N($R^{10}$)-$L^3$-C(=O)O$R^8$; or two adjacent $R^1$, together with the ring atoms to which they are attached independently and optionally form a carbocyclic ring, heterocyclic ring, aromatic ring or heteroaromatic ring, and wherein each $R^1$ is independently and optionally substituted with one or more $R^{12}$;

each $R^8$ is independently hydrogen, deuterium, alkyl, aminoalkyl, alkenyl, alkynyl, haloalkyl, cycloalkyl, heterocyclyl or aryl;

each $R^9$ is independently hydrogen, deuterium, hydroxy, amino, alkyl, aminoalkyl, alkenyl, alkynyl, haloalkyl, cycloalkyl, heterocyclyl aryl or —N$R^{10}$$R^{11}$;

each $R^{10}$ and $R^{11}$ is independently hydrogen, deuterium, alkyl, aminoalkyl, alkenyl, alkynyl, haloalkyl, cycloalkyl, heterocyclyl or aryl; or $R^{10}$ and $R^{11}$, together with the nitrogen atom to which they are attached, independently and optionally form a heterocyclic ring or heteroaromatic ring;

each $R^{12}$ is independently hydrogen, deuterium, F, Cl, Br, I, oxo, hydroxy, amino, nitro, cyano, alkyl, haloalkyl, alkoxy, alkylamino, alkenyl, alkynyl, cycloalkyl, heterocyclyl, aryl or heteroaryl;

each $L^1$ is independently a bond, —NH—, —C(=O)—, $C_{1-3}$ alkylene, $C_{2-4}$ alkenylene or $C_{2-4}$ alkynylene;

each $L^2$ is independently $C_{1-3}$ alkylene, $C_{2-4}$ alkenylene or $C_{2-4}$ alkynylene;

each $L^3$ is independently a bond or $C_{1-3}$ alkylene;

Z is

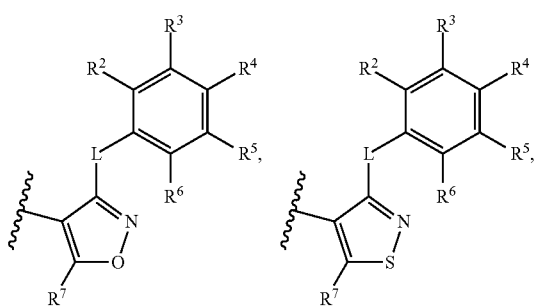

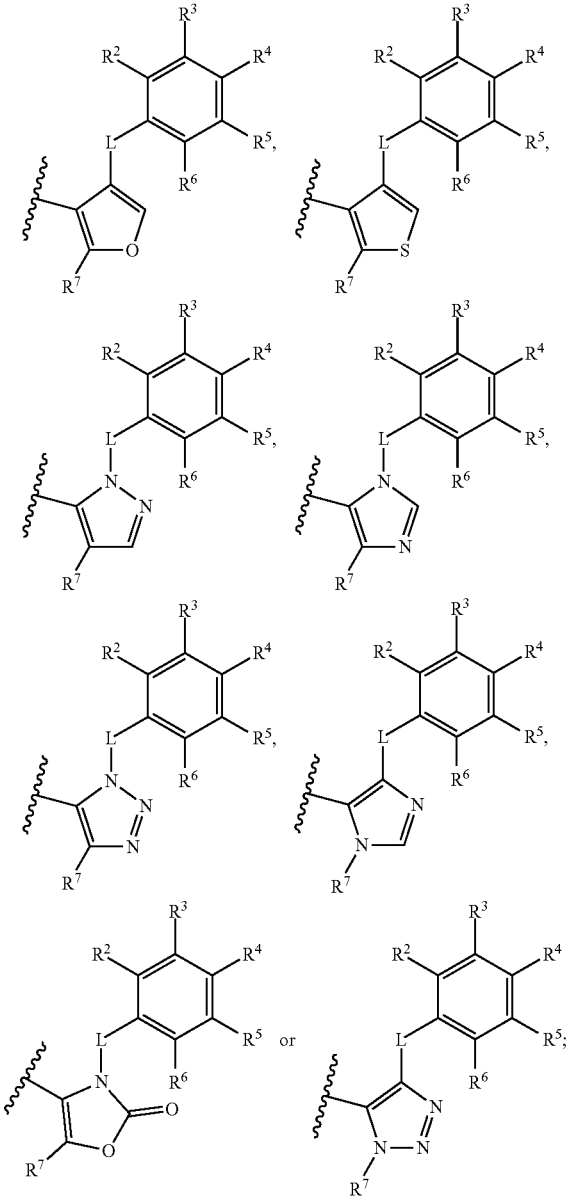

each $R^2$, $R^3$, $R^4$, $R^5$ and $R^6$ is independently hydrogen, deuterium, F, Cl, Br, I, hydroxy, —O—CH$_2$—CH$_2$— or —CH$_2$—O—CH$_2$—;

each $R^2$, $R^3$, $R^4$, $R^5$ and $R^6$ is independently hydrogen, deuterium, F, Cl, Br, I, hydroxy, amino, nitro, cyano, $C_{1-3}$ alkyl, $C_{1-3}$ haloalkyl, $C_{1-3}$ alkoxy or $C_{1-3}$ haloalkoxy;

each $R^7$ is independently hydrogen, deuterium, F, Cl, Br, I, hydroxy, amino, nitro, cyano, $C_{1-6}$ alkyl, $C_{1-6}$ hydroxyalkyl, $C_{1-6}$ haloalkyl, $C_{1-6}$ alkoxy, $C_{1-6}$ alkylamino, $C_{1-6}$ alkoxy-$C_{1-6}$ alkyl, $C_{3-6}$ cycloalkyl or $C_{2-6}$ heterocyclyl, and wherein the $C_{3-6}$ cycloalkyl and $C_{2-6}$ heterocyclyl is independently and optionally substituted with substituents selected from F, Cl, Br, I, hydroxy, amino, nitro and cyano;

m is 0, 1, 2, 3 or 4;

n is 0, 1 or 2; and each t is independently 0, 1 or 2;

with the proviso that a compound having formula (I) is not:

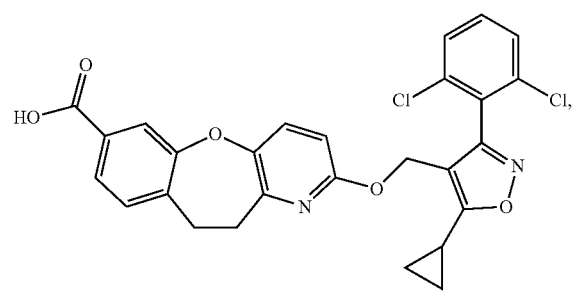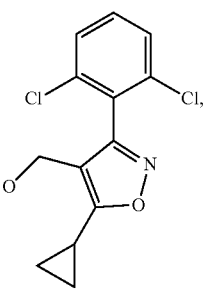
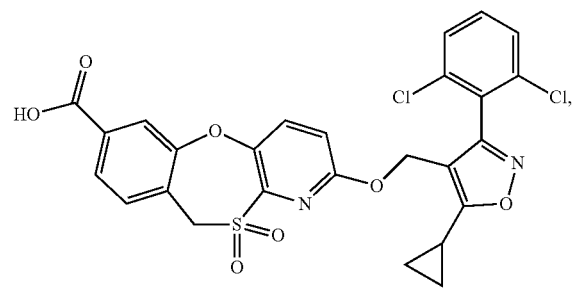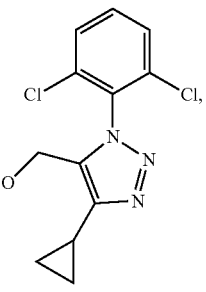
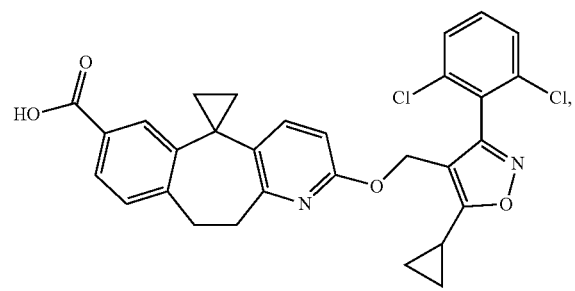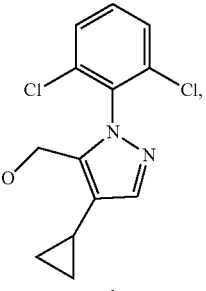
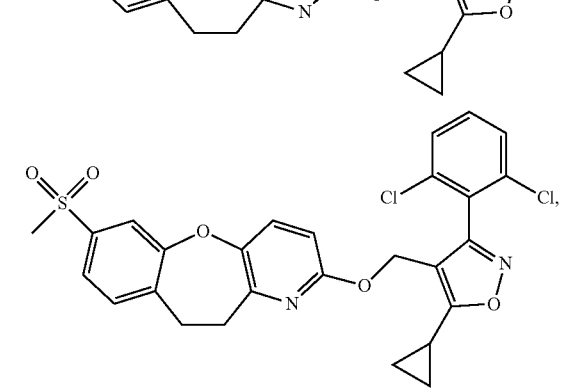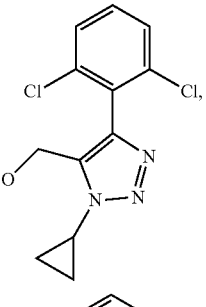
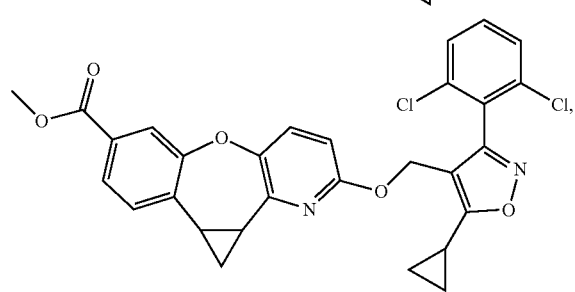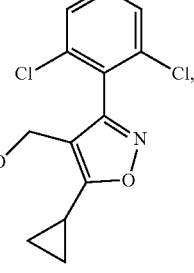
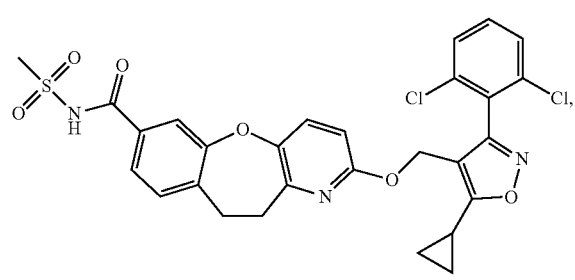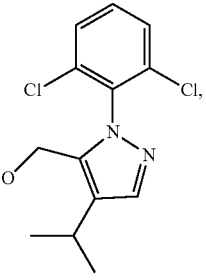

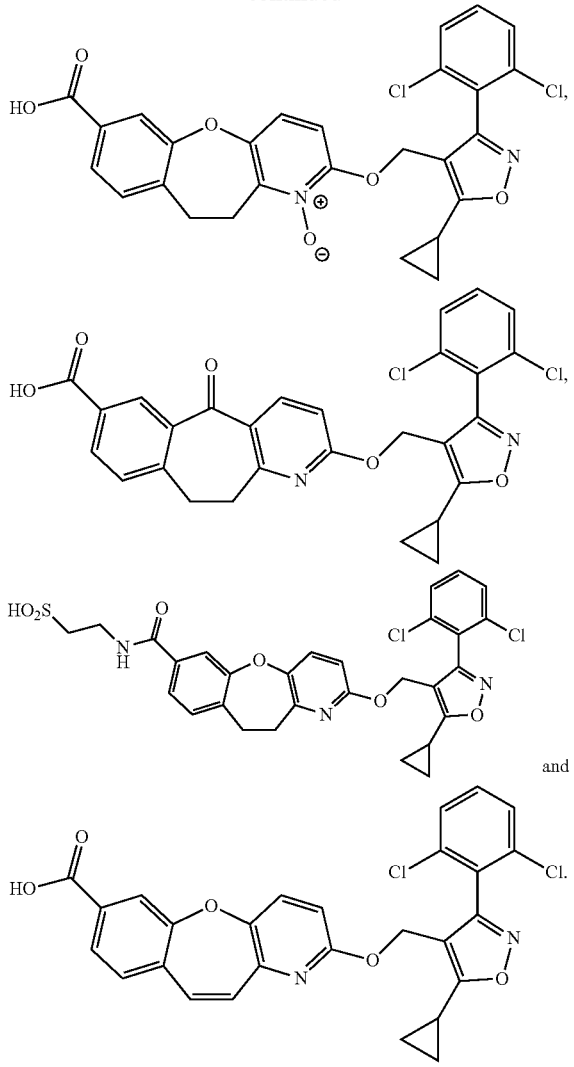

In some embodiments, each $R^x$ is independently hydrogen, deuterium, $C_{1-6}$ alkyl, $C_{1-6}$ aminoalkyl, $C_{1-6}$ haloalkyl, $C_{3-6}$ cycloalkyl, $C_{2-6}$ heterocyclyl, phenyl, halo-substituted phenyl or benzyl;

each $R^y$ and $R^z$ is independently hydrogen, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{2-6}$ alkenyl, $C_{2-6}$ alkynyl, $C_{3-6}$ cycloalkyl, $C_{2-6}$ heterocyclyl, phenyl, halo-substituted phenyl or benzyl; or $R^y$ and $R^z$ together with the same carbon atom to which they are attached, independently and optionally form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl;

each of $R^h$ and $R^k$ is independently methyl, ethyl, isopropyl or trifluoromethyl; or $R^h$ and $R^k$ together with the carbon atoms to which they are attached, form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl.

In other embodiments, each $R^x$ is independently hydrogen, deuterium, methyl, ethyl, isopropyl, aminomethyl, difluoromethyl, trifluoromethyl, cyclopropyl, cyclohexyl, tetrahydropyranyl, piperidinyl, phenyl, halo-substituted phenyl or benzyl;

each $R^y$ and $R^z$ is independently hydrogen, deuterium, F, Cl, Br, I, hydroxy, amino, nitro, cyano, methyl, ethyl, n-propyl, isopropyl, difluoromethyl, trifluoromethyl, 2,2-difluoroethyl, 2,2,2-trifluoroethyl, hydroxymethyl, 2-hydroxyethyl, aminomethyl, methoxy, ethoxy, isopropoxy, t-butoxy, methylamino, dimethylamino, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, halo-substituted phenyl or benzyl; or $R^y$ and $R^z$, together with the same carbon atom to which they are attached, independently and optionally form cyclopropane, cyclobutane, cyclopentane, cyclohexane, azetidine, tetrahydrofuran, pyrrolidine, piperidine, piperazine, tetrahydropyran, morpholine or thiomorpholine, and wherein the cyclopropane, cyclobutane, cyclopentane, cyclohexane, azetidine, tetrahydrofuran, pyrrolidine, piperidine, piperazine, tetrahydropyran, morpholine and thiomorpholine is independently and optionally substituted with substituents selected from F, Cl, Br, I, hydroxy, amino, nitro, cyano, methyl, ethyl, isopropyl and trifluoromethyl;

each of $R^h$ and $R^k$ is independently methyl, ethyl, isopropyl or trifluoromethyl; or $R^h$ and $R^k$, together with the carbon atoms to which they are attached, form cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinylene or thiomorpholinylene, and wherein the cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinylene and thiomorpholinylene is independently and optionally substituted with substituents selected from F, Cl, Br, I, hydroxy, amino, nitro, cyano, methyl, ethyl, isopropyl and trifluoromethyl.

In some embodiments, each $R^1$ is independently hydrogen, deuterium, F, Cl, Br, I, oxo, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy, $C_{1-6}$ alkoxy-$C_{1-3}$ alkyl, $C_{2-6}$ alkenyl, $C_{2-6}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, -$L^1$-C(=O)OR$^8$, -$L^1$-S(=O)$_r$R$^9$, —O-$L^2$-C(=O)OR, —O-$L^2$-S(=O)$_r$R$^9$, —C(=O)NR$^{10}$R$^{11}$, —C(=O)N(R$^{10}$)S(=O)$_2$R$^9$, —C(=NR$^{10}$)NR$^{10}$R$^{11}$, —C(=O)N(R$^{10}$)-$L^3$-S(=O)$_2$OR$^8$, —C(=O)N(R$^{10}$)C(=O)OR$^8$ or —C(=O)N(R$^{10}$)-$L^3$-C(=O)OR$^8$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each the $R^1$ is independently and optionally substituted with one or more $R^{12}$;

each $R^8$ is independently hydrogen, deuterium, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl or phenyl;

each $R^9$ is independently hydrogen, deuterium, hydroxy, amino, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl, phenyl or —NR$^{10}$R$^{11}$;

each $R^{10}$ and $R^{11}$ is independently hydrogen, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-6}$ heterocyclyl or phenyl, or $R^{10}$ and $R^{11}$ together with the nitrogen atom to which they are attached, independently and optionally form a $C_{2-6}$ heterocyclic ring or $C_{1-5}$ heteroaromatic ring;

each $R^{12}$ is independently hydrogen, deuterium, F, Cl, Br, I, oxo, hydroxy, amino, nitro, cyano, $C_{1-6}$ alkyl, $C_{1-6}$ haloalkyl, $C_{1-6}$ alkoxy, $C_{1-6}$ alkylamino, $C_{2-6}$ alkenyl, $C_{2-6}$ alkynyl, $C_{3-6}$ cycloalkyl, $C_{2-6}$ heterocyclyl, phenyl or $C_{1-5}$ heteroaryl.

In other embodiments, each $R^1$ is independently hydrogen, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy, $C_{1-3}$ alkoxy-$C_{1-3}$ alkyl, $C_{2-4}$ alkenyl, $C_{2-4}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, -L$^1$-C(=O)OR$^8$, -L$^1$-S(=O)$_t$R$^9$, —O-L$^2$-C(=O)OR$^8$, —O-L$^2$-S(=O)$_t$R$^9$, —C(=O)NR$^{10}$R$^{11}$, —C(=O)N(R$^{10}$)S(=O)$_2$R$^9$, —C(=NR$^{10}$)NR$^{10}$R$^{11}$, —C(=O)N(R$^{10}$)-L$^3$-S(=O)$_2$OR$^8$, —C(=O)N(R$^{10}$)C(=O)OR$^8$ or —C(=O)N(R$^{10}$)-L$^3$-C(=O)OR$^8$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each $R^1$ is independently and optionally substituted with one or more $R^{12}$;

each $R^8$ is independently hydrogen, deuterium, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl or phenyl;

each $R^9$ is independently hydrogen, deuterium, hydroxy, amino, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl, phenyl or —NR$^{10}$R$^{11}$;

each $R^{10}$ and $R^{11}$ is independently hydrogen, deuterium, $C_{1-3}$ alkyl, $C_{1-3}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or phenyl; or $R^{10}$ and $R^{11}$, together with the nitrogen atom to which they are attached, independently and optionally form a $C_{2-6}$ heterocyclic ring or $C_{1-5}$ heteroaromatic ring;

each $R^{12}$ is independently hydrogen, deuterium, F, Cl, Br, I, oxo, hydroxy, amino, nitro, cyano, $C_{1-3}$ alkyl, $C_{1-3}$ haloalkyl, $C_{1-3}$ alkoxy, $C_{1-3}$ alkylamino, $C_{2-4}$ alkenyl, $C_{2-4}$ alkynyl, $C_{3-6}$ cycloalkyl, $C_{2-6}$ heterocyclyl, phenyl or $C_{1-5}$ heteroaryl.

In other embodiments, each $R^1$ is independently hydrogen, deuterium, F, Cl, Br, I, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxylmethyl, isopropoxylmethyl, ethenyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—$C_{1-3}$ alkyl, —C(=O)NHS(=O)$_2$—$C_{1-3}$ alkyl, —C(=O)NHS(=O)$_2$-phenyl, —C(=O)NH—$C_{1-3}$ alkylene-S(=O)$_2$OH, —C(=O)NH—$C_{1-3}$ alkylene-C(=O)OH, —S(=O)$_2$NH$_2$, —S(=O)$_2$OH, —S(=O)$_2$—$C_{1-3}$ alkyl, —C(=O)NH$_2$ or —C(=O)N(CH$_3$)$_2$; wherein each $R^1$ is independently and optionally substituted with one or more $R^{12}$;

each $R^{12}$ is independently hydrogen, deuterium, F, Cl, Br, I, oxo, hydroxy, amino, nitro, cyano, methyl, trifluoromethyl, methoxy, methylamino, vinyl, ethynyl, cyclopropyl, cyclohexyl, tetrahydrofuranyl, piperazinyl, phenyl or pyridinyl.

In some embodiments, each $R^2$, $R^3$, $R^4$, $R^5$ and $R^6$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy;

each $R^7$ is independently hydrogen, deuterium, F, Cl, Br, I, hydroxy, amino, nitro, cyano, methyl, ethyl, isopropyl, t-butyl, hydroxymethyl, 2-hydroxyisopropyl, difluoromethyl, trifluoromethyl, 2-fluoroisopropyl, methoxy, isopropoxy, t-butoxy, dimethylamino, isopropoxymethyl, t-butoxymethyl, cyclopropyl, cyclobutyl, cyclopentyl, cyclohexyl, tetrahydrofuranyl, pyrrolidinyl, piperidinyl, piperazinyl, morpholinyl or thiomorpholinyl, and wherein the cyclopropyl, cyclobutyl, cyclopentyl, cyclohexyl, tetrahydrofuranyl, pyrrolidinyl, piperidinyl, piperazinyl, morpholinyl and thiomorpholinyl is independently and optionally substituted with substituents selected from F, Cl, Br, I, hydroxy, amino, nitro and cyano.

In one aspect, provided herein is a pharmaceutical composition comprising the compound described above, the pharmaceutical composition optionally further comprise a pharmaceutically acceptable carrier, excipient, diluent, adjuvant, vehicle or a combination thereof.

In one aspect, provided herein is use of the compound described above in the manufacture of a medicament for preventing, managing, treating or lessening a disease mediated by FXR in a patient.

In some embodiments, the disease mediated by FXR is a cardiovascular and cerebrovascular disease, a disease related to dyslipidemia, metabolic syndrome, a hyperproliferative disease, fibrosis, an inflammatory disease or a disease related to liver and gallbladder.

In one aspect, provided herein is the compound described above for use in preventing, managing, treating or lessening a disease mediated by FXR in a patient.

In other aspect, provided herein is a method of preparing, separating or purifying the compound described above.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The present invention is expected to cover all alternatives, variants and equivalents, which may be included within the scope of the invention as defined in claim. Those skilled in the art will recognize many methods and materials similar or equivalent to those described herein, which may be applied to the practice of the present invention. The present invention is by no means limited to the methods and materials described herein. There are a lot of literature and similar substances distinguished or inconsistent with the present invention, including but not limited to the definitions of terms, the use of terminology, described techniques, or the like, this application controls.

The present invention will apply the following definitions unless otherwise specified. For purposes of this invention, the chemical elements are defined according to the Periodic Table, CAS version and chemical manuals, 75, thEd, 1994. Additionally, general principles of organic chemistry are described in "Organic Chemistry", Thomas Sorrell, University Science Books, Sausalito: 1999, and Smith et al., and "March's Advanced Organic Chemistry", John Wiley & Sons, New York: 2007, all of which are incorporated herein by reference in their entireties.

The term "comprise" is an open expression, it includes the contents disclosed herein, but don't exclude other contents.

As described herein, compounds disclosed herein may optionally be substituted with one or more substituents, such as are illustrated generally formula in the invention, or as exemplified by particular classes, subclasses, and species of the invention. It will be appreciated that the phrase "optionally substituted" is used interchangeably with the phrase "substituted or unsubstituted". In general, the term "optionally" whether or not located before the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents may be, but are not limited to H, F, Cl, Br, I, nitro, cyano, oxo (=O), hydroxy, alkyl, hydroxyalkyl, alkylamino, aminoalkyl, haloalkoxy, cycloalkyl, amino, aryl, heterocyclyl, heteroaryl, alkenyl, alkynyl, cycloalkyloxy, alkoxy, alkoxyalkyl, haloalkyl, —COOH, -alkylene-C(=O)O-alkyl, -alkylene-S(=O)$_2$-alkyl, -alkylene-S(=O)$_2$-amino, —S(=O)$_2$-alkyl, —S(=O)$_2$-amino, —S(=O)$_2$OH, —O-alkylene-C(=O)O-alkyl, —O-alkylene-S(=O)$_2$-alkyl, —O-alkylene-S(=O)$_2$-amino, —O-alkylene-S(=O)$_2$OH, —C(=O)NH$_2$, —C(=O)NH-alkyl, —C(=O)N(alkyl)-alkyl, —C(=O)NHS(=O)$_2$-alkyl, —C(=O)NHS(=O)$_2$-amino, —C(=O)NHS(=O)$_2$OH, —N(R$^{10}$)C(=O)NR$^{10}$R$^{11}$, —OC(=O)R$^9$, —N(haloalkyl)-alkyl, —N(alkyl)-S(=O)$_2$-alkyl, —NHS(=O)$_2$-alkyl, —NHS(=O)$_2$-haloalkyl, —N(alkyl)S(=O)$_2$-haloalkyl, —N(alkyl)S(=O)$_2$-alkylamino, —NHC(=O)-alkyl, —NHC(=O)-haloalkyl, —N(alkyl)C(=O)-haloalkyl, —N(alkyl)C(=O)-alkylamino, —N(alkyl)C(=O)O-alkyl, —NHC(=O)O-alkyl, —NHC(=O)O-haloalkyl, —N(alkyl)C(=O)O-haloalkyl, —N(alkyl)C(=O)O-aminoalkyl, —NHC(=O)—NH$_2$, —NHC(=O)NH-(alkyl), —NHC(=O)NH(haloalkyl), —NHC(=O)N(alkyl)-alkyl, —OC(=O)-alkyl, —OC(=O)-amino, —OC(=O)-alkylamino, —OC(=O)-aminoalkyl, —OC(=O)-alkoxy, —C(=O)N(alkyl)S(=O)$_2$-alkyl, —C(=O)N(alkyl)S(=O)$_2$-amino, —C(=O)NH—S(=O)$_2$OH, —C(=NH)NH$_2$, —C(=NH)NH-alkyl, —C(=NH)N(alkyl)-alkyl, —C(=N-alkyl)-NH$_2$, —C(=O)NH-alkylene-S(=O)$_2$OH, —C(=O)NHC(=O)OH, —C(=O)NHC(=O)O-alkyl, —C(=O)N(alkyl)C(=O)O-alkyl, —C(=O)NH-alkylene-C(=O)OH and —C(=O)NH-alkylene-C(=O)O-alkyl, and the like, and wherein R$^9$, R$^{10}$ and R$^{11}$ are as defined herein.

The term "alkyl" refers to a saturated linear or branched-chain monovalent hydrocarbon radical of 1 to 20 carbon atoms, or 1 to 10 carbon atoms, or 1 to 6 carbon atoms, or 1 to 4 carbon atoms, or 1 to 3 carbon atoms, or 1 to 2 carbon atoms, wherein the alkyl radical may be optionally and independently substituted with one or more substituents described herein. Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl and n-octyl, etc. The term "alkyl" or the prefix "alk-" is inclusive of both straight chain and branched saturated carbon chain. The term "alkylene" used herein refers to a saturated divalent hydrocarbon group derived from a straight or branched chain saturated hydrocarbon by the removal of two hydrogen atoms, such examples include, but are not limited to methylene, ethylidene and isopropylidene, and the like.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp$^2$ double bond, wherein the alkenyl radical may be independently and optionally substituted with one or more substituents described herein, and includes radicals having "cis" and "trans" orientations, or alternatively, "E" and "Z" orientations. Examples include, but are not limited to, ethenyl or vinyl (—CH=CH$_2$), allyl (—CH$_2$CH=CH$_2$), but-3-enyl (—CH$_2$CH$_2$CH=CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is independently and optionally substituted with one or more substituents described herein. Examples include, but are not limited to, ethynyl (—C≡CH), propargyl (—CH$_2$C≡CH), and the like.

The term "heteroatom" refers to one or more of O, S, N, P and Si, including any oxidized form of C, N, S, or P; the quaternized form of any basic N; or a substitutable nitrogen of a heterocyclic ring, for example, N (as in 3,4-dihydro-2H-pyrrolyl), NH (as in pyrrolidinyl) or NR (as in N-substituted pyrrolidinyl); or —CH$_2$— of a heterocyclic ring is oxidized to form —C(=O)— form.

The term "halogen" or "halo" refers to fluoro (F), chloro (Cl), bromo (Br), or iodo (I).

The term "unsaturated" refers to a moiety having one or more units of unsaturation.

The term "alkoxy" refers to an alkyl group, as defined herein, attached to the remaining part of the molecule through an oxygen atom. In some embodiments, alkoxy is C$_{1-4}$ alkoxy. Examples include, but are not limited to, methoxy, ethoxy, propoxy, butoxy, and the like. The alkoxy group may be optionally substituted with one or more substituents disclosed herein.

The term "alkoxyalkyl" refers to an alkyl group substituted with one or more alkoxy, and alkoxy and alkyl are as defined herein. In some embodiments, alkoxyalkyl is C$_{1-6}$ alkoxy-C$_{1-6}$ alkyl. In other embodiments, alkoxyalkyl is C$_{1-3}$ alkoxy-C$_{1-3}$ alkyl. And each said alkoxyalkyl can be independently and optionally substituted with one or more substituents described herein.

The terms "haloalkyl", "haloalkenyl" or "haloalkoxy" refer to alkyl, alkenyl, or alkoxy, as the case may be, substituted with one or more halogen atoms. In some embodiments, haloalkyl is $C_{1-6}$ haloalkyl. In other embodiments, haloalkyl is $C_{1-3}$ haloalkyl. In some embodiments, haloalkoxy is $C_{1-6}$ haloalkoxy. In other embodiments, haloalkoxy is $C_{1-3}$ haloalkoxy. Some non-limiting examples of "haloalkyl", "haloalkenyl" or "haloalkoxy" groups include trifluoromethyl, 2-chloro-vinyl, 2,2-difluoroethyl, trifluoromethoxy, and the like. And wherein optionally each of the haloalkyl, haloalkenyl or haloalkoxy may be optionally substituted with one or more substituents described herein.

The term "alkylamino" refers to "N-alkylamino" and "N,N-dialkylamino", wherein amino groups are independently substituted with one alkyl radical or two alkyl radicals, respectively. In some embodiments, the alkylamino group is $C_{1-6}$ alkylamino or a ($C_{1-6}$ alkyl) amino group. In other embodiments, the alkylamino group is $C_{1-3}$ alkylamino or a ($C_{1-3}$ alkyl) amino group. Some non-limiting examples of such group include, N-methylamino, N-ethylamino, N,N-dimethylamino, N,N-diethylamino, and the like. And wherein the alkylamino radical is optionally substituted with one or more substituents described herein.

The term "cycloalkyl" or "cycloalkane" refers to a monovalent or multivalent saturated ring having 3 to 12 carbon atoms as a monocyclic, bicyclic, or tricyclic carbon ring system, but not an aromatic ring. In some embodiments, the cycloalkyl group contains 3 to 12 carbon atoms. In other embodiments, the cycloalkyl group contains 3 to 8 carbon atoms. In still other embodiments, the cycloalkyl group contains 3 to 6 carbon atoms. Examples include, but are not limited to, cyclopropyl, cyclobutyl, cyclopentyl, cyclohexyl, and the like. The cycloalkyl group may be optionally substituted with one or more substituents disclosed herein.

The term "cycloalkyloxy" refers to a cycloalkyl attached to the rest of the compound molecule through an oxygen atom, and cycloalkyl is as defined herein.

The term "cycloalkylalkyl" refers to a cycloalkyl attached to the rest of the compound molecule through an alkyl, and cycloalkyl and alkyl are as defined herein.

The term "carbocycle", "carbocyclyl", or "carbocyclic ring" refers to a monovalent or multivalent non-aromatic, saturated or partially unsaturated ring having 3 to 12 carbon atoms as a monocyclic, bicyclic or tricyclic ring system. A carbobicyclic ring system includes a spiro carbobicyclyl or a fused carbobicyclyl. In some embodiments, suitable carbocyclyl groups include 3-8 carbon atoms; in other embodiments, carbocyclyl groups include 3-6 carbon atoms. Suitable carbocyclyl groups include, but are not limited to, cycloalkyl, cycloalkenyl, and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cyclohendecyl, cyclododecyl, and the like. The said carbocyclyl groups may be independently unsubstituted or substituted by one or more groups disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms, but not an aromatic ring, of which at least one ring atom is a heteroatom. Unless otherwise specified, the heterocyclyl group may be carbon or nitrogen linked, and the heteroatom is as defined herein. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl and 2-oxa-5-azabicyclo[2.2.1]hept-5-yl. Some non-limiting examples of heterocyclyl wherein —$CH_2$— group is replaced by —C(=O)— moiety include 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized include sulfolanyl, 1,1-dioxo-thiomorpholinyl. The heterocyclyl group may be optionally substituted with one or more substituents disclosed herein.

The term "heterocyclylalkyl" refers to a heterocyclyl attached to the rest of the compound molecule through an alkyl, and heterocyclyl and alkyl is as defined herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members, and that has a single point or multipoint of attachment to the rest of the molecule. The term "aryl" and "aromatic ring" can be used interchangeably herein. Examples of aryl ring may include phenyl, naphthyl and anthracene. The aryl group may be optionally and independently substituted with one or more substituents disclosed herein.

The term "arylalkyl" refers to an alkyl group substituted with one or more aryl groups, wherein the alkyl group and aryl group are as defined herein. Some non-limiting examples of the arylalkyl group include phenylmethyl, phenylethyl, and the like.

The term "heteroaryl" refers to monocyclic, bicyclic and tricyclic carbocyclic ring systems having a total of five to twelve ring members, or five to ten ring members, or five to six ring members, wherein at least one ring system is an aromatic ring, and at least one ring system contains one or more hetero atoms, and wherein each ring in the system contains 5 to 7 ring members and that has a single point or multipoint of attachment to the rest of the molecule. The term "heteroaryl" and "heteroaromatic ring" or "heteroaromatic compound" can be used interchangeably herein. The heteroaryl group is optionally substituted with one or more substituents disclosed herein. In one embodiment, a 5-10 membered heteroaryl group comprises 1, 2, 3 or 4 heteroatoms independently selected from O, S and N, wherein the nitrogen atom can be further oxidized.

Some non-limiting examples of heteroaryl rings include furanyl, imidazolyl (e.g., N-imidazolyl, 2-imidazolyl, 4-imidazolyl, 5-imidazolyl), isoxazolyl, oxazolyl (e.g. 2-oxazolyl, 4-oxazolyl, 5-oxazolyl), pyrrolyl (e.g., N-pyrrolyl, 2-pyrrolyl, 3-pyrrolyl), pyridyl, pyrimidinyl (e.g. 2-pyrimidinyl, 4-pyrimidinyl, 5-pyrimidinyl), pyridazinyl, thiazolyl (e.g., 2-thiazolyl, 4-thiazolyl, 5-thiazolyl), tetrazolyl (e.g., 5-tetrazolyl), triazolyl, thienyl (e.g., 2-thienyl, 3-thienyl), pyrazolyl isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), 1,2,3,4- tetrahydroisoquinolinyl, 1,3-benzodioxolyl, indolinyl, isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, and [1,2,4]triazolo[1,5-a]pyridyl, and the like.

The term "aminoalkyl" refers to a $C_{1-10}$ linear or branched-chain alkyl group substituted with one or more amino groups. In some embodiments, the aminoalkyl is a $C_{1-6}$ alkyl substituted with one or more amino groups. Some non-limiting examples of the aminoalkyl group include aminomethyl, aminoethyl, aminopropyl, aminobutyl and aminohexyl. The aminoalkyl group is optionally substituted with one or more substituents described herein.

The term "hydroxyalkyl" refers to an alkyl group substituted with one or more hydroxy groups, wherein the alkyl group is as defined herein. Some non-limiting examples of the hydroxyalkyl group include hydroxymethyl, hydroxyethyl, and 1,2-dihydroxy-ethyl, and the like.

The term "halo-substituted aryl" refers to an aryl group substituted with one or more identical or different halogen atoms, wherein halogen and aryl are as described herein. Such examples include, but are not limited to, fluorophenyl, difluorophenyl, trifluorophenyl, chlorophenyl, dichlorophenyl, trichlorophenyl, bromophenyl, tribromophenyl, dibromophenyl, chlorofluorophenyl, fluorobromophenyl, chlorobromophenyl, and the like. The halogen-substituted aryl group is optionally substituted with one or more substituents disclosed herein.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. Wherein the alkylene group is optionally substituted with one or more substituents described herein. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by methylene (—CH$_2$—), ethylene (—CH$_2$CH$_2$—), isopropylene (—CH(CH$_3$)CH$_2$—), and the like.

The term "alkenylene" refers to an unsaturated divalent hydrocarbon group derived from an alkylene group by the removal of two hydrogen atoms. Unless otherwise specified, the alkenylene group contains 1-12 carbon atoms. Wherein the alkenylene group is optionally substituted with one or more substituents described herein. In some embodiments, the alkenylene group contains 1-6 carbon atoms. In other embodiments, the alkenylene group contains 1-4 carbon atoms. In still other embodiments, the alkenylene group contains 1-3 carbon atoms. In yet other embodiments, the alkenylene group contains 1-2 carbon atoms. Some non-limiting examples of the alkenylene group include ethenylene (—CH=CH—), propenylene (—CH$_2$CH=CH—), and the like.

The term "alkynylene" refers to a linear or branched divalent hydrocarbon radical of 2 to 12 carbon atoms with at least one site of unsaturation, i.e., a carbon-carbon, sp triple bond, wherein the alkynylene radical may be optionally substituted with one or more substituents described herein. In some embodiments, the alkynylen contains 2 to 8 carbon atoms. In other embodiments, the alkynylene contains 2 to 6 carbon atoms. In still other embodiments, the alkynylene contains 2 to 4 carbon atoms. Examples of such groups include, but are not limited to, ethynylene (—C≡C—), and the like.

As described herein, substituents connected to the center position of the ring through a bond represent that the ring to which substituents connected may be substituted in any reasonable and connectable position. For example, formula (a) represents ring E can be substituted with one or more $R^o$ substituents in any reasonable and substitutable position.

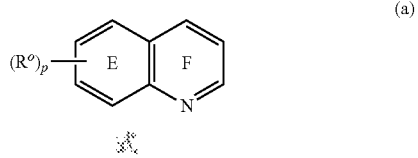

(a)

Furthermore, unless otherwise stated, the phrase "each . . . is independently" is used interchangeably with the phrase "each (of) . . . and . . . is independently". It should be understood broadly that the specific options expressed by the same symbol are independent of each other in different radicals; or the specific options expressed by the same symbol are independent of each other in same radicals.

Unless otherwise stated, structures depicted herein are also meant to include all isomeric (e.g., enantiomeric, diastereomeric, geometric or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, geometric, or conformational mixtures of the present compounds are within the scope disclosed herein.

Unless otherwise stated, structures and compounds depicted herein are also meant to include all isomeric (e.g., enantiomeric, diastereomeric, geometric or conformational) forms, N-oxide, hydrate, solvate, metabolite, pharmaceutically acceptable salt or a prodrug thereof. Therefore, single stereochemical isomers as well as enantiomer, diastereomer, geometric isomer, conformer, N-oxide, anhydrate, solvate, metabolite, pharmaceutically acceptable salt or prodrug of the compounds disclosed herein are within the scope of the present invention. Additionally, unless otherwise stated, structures depicted herein are also meant to include compounds that differ only in the presence of one or more isotopically enriched atoms.

A "metabolite" refers to a product produced through metabolism in the body of a specified compound, a pharmaceutically acceptable salt, analog or derivative, which exhibits similar activity of the compound of Formula (I) in vivo or in vitro. The metabolites of a compound may be identified using routine techniques known in the art and their activities can be determined using tests such as those described herein. Such products may result for example from oxidation, reduction, hydrolysis, amidation, deamidation, esterification, deesterification, or enzyme cleavage, and the like, of the administered compound. Accordingly, the invention includes metabolites of the compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal (formed) salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "hydrate" refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I) containing hydroxy group, for example, a pharmaceutically acceptable ester which is hydrolysed in the human or animal body to produce the parent alcohol. Some non-limiting examples of in vivo hydrolysable ester forming groups of a compound of the Formula (I) containing hydroxy group include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514), in which the amine compound is reacted with m-chloroperoxybenzoic acid (MCPBA), for example, in an inert solvent such as dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic $(C_1-C_{24})$ esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery,* 2008, 7, 255-270, and S. J. Hecker et al, Prodrugs of Phosphates and Phosphonates, *Journal of Medicinal Chemistry,* 2008, 51, 2328-2345.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC), benzyloxycarbonyl (CBZ) and 9-fluorenylmethylenoxy-carbonyl (Fmoc), and the like. Similarly, a "hydroxy-protecting group" refers to a substituent of a hydroxy group that blocks or protects the hydroxy functionality. Suitable protecting groups include methyl, methoxymethyl, acetyl and silyl, and the like. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxy-methyl, 2-(p-toluenesulfonyl)ethyl, 2-(p-nitrophenylsulfonyl)ethyl, 2-(diphenylphosphino) ethyl, nitroethyl, and the like. For a general description of protecting groups and their use, see: T W. Greene, Protective Groups in Organic Synthesis, John Wiley & Sons, New York, 1991; and P. J. Kocienski, Protecting Groups, Thieme, Stuttgart, 2005.

As used herein, the term "therapeutically effective amount" refers to an amount of a compound of the Formula (I) which is sufficient to obtain the desired therapeutic effect. Thus, a therapeutically effective amount of a compound of the Formula (I) for the treatment of conditions mediated by FXR is sufficient to treat conditions mediated by FXR.

As used herein, the term "dyslipidemia" refers to an abnormality of lipids and lipoproteins, or abnormal amounts of lipids and lipoproteins in the blood, as well as these diseases generated, caused, exacerbated or accompanied by such abnormalities (See Dorland's Illustrated Medical Dictionary, 29th edition, W.B. Saunders Publishing Company, New York, N.Y.). These diseases encompassed within the definition of dyslipidemia include hyperlipidemia, hypertriglyceridemia, low plasma HDL, high plasma LDL, high plasma VLDL, liver cholestasis, and hypercholesterolemia.

As used herein, the term "diseases related to dyslipidemia" include, but are not limited to, atherosclerosis, thrombosis, coronary artery disease, stroke and hypertension disease. And diseases related to dyslipidemia also include metabolic diseases such as obesity, diabetes, insulin resistance and complications thereof. The term "cholestasis" refers to any condition caused by that the flow of bile from the liver is blocked, which may be intrahepatic (i.e., occurring inside the liver) or extrahepatic (i.e., occurring outside the liver).

As used herein, the term "liver fibrosis" includes liver fibrosis caused by any reason, including but not limited to virus-induced liver fibrosis, such as liver fibrosis caused by the hepatitis B and hepatitis C; liver fibrosis caused by contacting with alcohol (alcoholic liver disease), pharmaceutical compounds, oxidative stress, cancer radiation or industrial chemicals; and liver fibrosis caused by primary biliary cirrhosis, fatty liver, obesity, non-alcoholic steatohepatitis, cystic fibrosis, hemochromatosis, and autoimmune hepatitis and other diseases.

As used herein, the term "non-alcoholic fatty liver disease (NAFLD)" refers to a metabolic disease associated with insulin resistance, including simple fatty liver (SFL), non-alcoholic steatohepatitis (NASH), steatohepatic fibrosis and liver cirrhosis.

As used herein, "FXR modulators" refers to a substance that directly binds to the FXR and regulates activity of the FXR, including FXR agonists, FXR partial agonists and FXR antagonists.

As used herein, the term "FXR agonist" refers to a substance that directly binds to the FXR and upregulates activity of the FXR.

Unless otherwise indicated herein or clearly contradicted by the context, the terms "a", "an", "the" and similar terms used in the context of the present invention (particularly in the context of the claims) are to be construed to cover both the singular and the plural.

DESCRIPTION OF COMPOUNDS OF THE INVENTION

The present invention relates to compounds, or pharmaceutical compositions thereof, which bind to FXR and act as modulators of the FXR). The present invention further relates to said compounds or the use thereof in the manufacture of a medicament for the treatment of diseases and/or conditions through said compounds binding to the FXR nuclear receptor disclosed herein. The present invention further describes a method for the synthesis of the compounds. The compounds of the invention exhibit improved biological activity and pharmacokinetic advantages.

The invention relates to a compound having formula (I), or a stereoisomer, a geometric isomer, a tautomer, an N-oxide, a hydrate, a solvate, a metabolite, a pharmaceutically acceptable salt or a prodrug thereof,

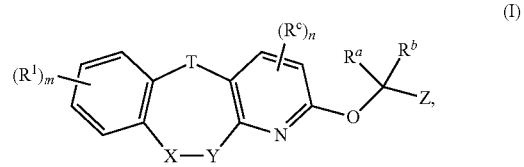

(I)

wherein:
T is —NH—, —O—, —S—, —C(=O)— or —CH$_2$—;
each of X and Y is independently a bond, —O—, —S(=O)$_t$—, —NR$^x$—, —CR$^y$R$^z$— or —C(=O)—, or —X—Y— is —CHR$^h$—CHR$^k$— or —CR$^y$=CR$^z$—;
each R$^x$ is independently hydrogen, deuterium, alkyl, aminoalkyl, haloalkyl, cycloalkyl, heterocyclyl, aryl, halo-substituted aryl or arylalkyl;
each R$^y$ and R$^z$ is independently hydrogen, deuterium, F, Cl, Br, I, hydroxy, amino, nitro, cyano, alkyl, haloalkyl, hydroxyalkyl, aminoalkyl, alkoxy, alkylamino, alkenyl, alkynyl, cycloalkyl, heterocyclyl, aryl, halo-substituted aryl or arylalkyl; or R$^y$ and R$^z$ together with the same carbon atom to which they are attached, independently and optionally form a cycloalkane ring or heterocyclic ring, and wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;
each of R$^h$ and R$^k$ is independently hydrogen, deuterium, F, Cl, Br, I, hydroxy, amino, nitro, cyano, methyl, ethyl, isopropyl or trifluoromethyl; or R$^h$ and R$^k$, together with the carbon atoms to which they are attached, form a cycloalkane ring or heterocyclic ring, wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;
each of R$^a$ and R$^b$ is independently hydrogen, deuterium or C$_{1-3}$ alkyl;
each R$^c$ is independently hydrogen, deuterium, F, Cl, Br, I, oxo, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxymethyl, isopropoxymethyl, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—$C_{1-3}$ alkyl, —C(=O)NHS(=O)$_2$—$C_{1-3}$ alkyl, —C(=O)NHS(=O)$_2$-phenyl, —C(=O)NH—$C_{1-3}$ alkylene-S(=O)$_2$OH, —C(=O)NH—$C_{1-3}$ alkylene-C(=O)OH, —S(=O)$_2$NH$_2$, —S(=O)$_2$OH, —S(=O)$_2$—$C_{1-3}$ alkyl, —C(=O)NH$_2$ or —C(=O)N(CH$_3$)$_2$;

each $R^1$ is independently hydrogen, deuterium, F, Cl, Br, I, hydroxy, amino, nitro, cyano, alkyl, haloalkyl, hydroxyalkyl, aminoalkyl, alkoxy, alkylamino, haloalkoxy, alkoxyalkyl, alkenyl, alkynyl, cycloalkyl, cycloalkoxy, cycloalkylalkyl, heterocyclyl, heterocyclylalkyl, aryl, halo-substituted aryl, arylalkyl, heteroaryl, -L$^1$-C(=O)OR$^8$, -L$^1$-S(=O)$_t$R$^9$, —O-L$^2$-C(=O)OR$^8$, —O-L$^2$-S(=O)$_t$R$^9$, —C(=O)NR$^{10}$R$^{11}$, —C(=O)N(R$^{10}$)S(=O)$_2$R$^9$, —C(=NR$^{10}$)NR$^{10}$R$^{11}$, —C(=O)N(R$^{10}$)-L$^3$-S(=O)$_2$OR$^8$, —C(=O)N(R$^{10}$)C(=O)OR$^8$ or —C(=O)N(R$^{10}$)-L$^3$-C(=O)ORB; or two adjacent $R^1$, together with the ring atoms to which they are attached, independently and optionally form a carbocyclic ring, heterocyclic ring, aromatic ring or heteroaromatic ring, and wherein each $R^1$ is independently and optionally substituted with one or more $R^{12}$;

each $R^8$ is independently hydrogen, deuterium, alkyl, aminoalkyl, alkenyl, alkynyl, haloalkyl, cycloalkyl, heterocyclyl or aryl;

each $R^9$ is independently hydrogen, deuterium, hydroxy, amino, alkyl, aminoalkyl, alkenyl, alkynyl, haloalkyl, cycloalkyl, heterocyclyl, aryl or —NR$^{10}$R$^{11}$;

each $R^{10}$ and $R^{11}$ is independently hydrogen, deuterium, alkyl, aminoalkyl, alkenyl, alkynyl, haloalkyl, cycloalkyl, heterocyclyl or aryl; or $R^{10}$ and $R^{11}$, together with the nitrogen atom to which they are attached, independently and optionally form a heterocyclic ring or heteroaromatic ring;

each $R^{12}$ is independently hydrogen, deuterium, F, Cl, Br, I, oxo, hydroxy, amino, nitro, cyano, alkyl, haloalkyl, alkoxy, alkylamino, alkenyl, alkynyl, cycloalkyl, heterocyclyl, aryl or heteroaryl;

each $L^1$ is independently a bond, —NH—, —C(=O)—, $C_{1-3}$ alkylene, $C_{2-4}$ alkenylene or $C_{2-4}$ alkynylene;

each $L^2$ is independently $C_{1-3}$ alkylene, $C_{2-4}$ alkenylene or $C_{2-4}$ alkynylene;

each $L^3$ is independently a bond or $C_{1-3}$ alkylene;

Z is

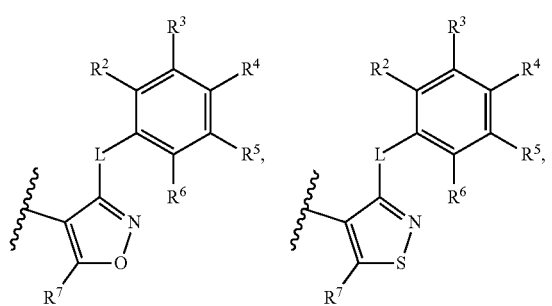

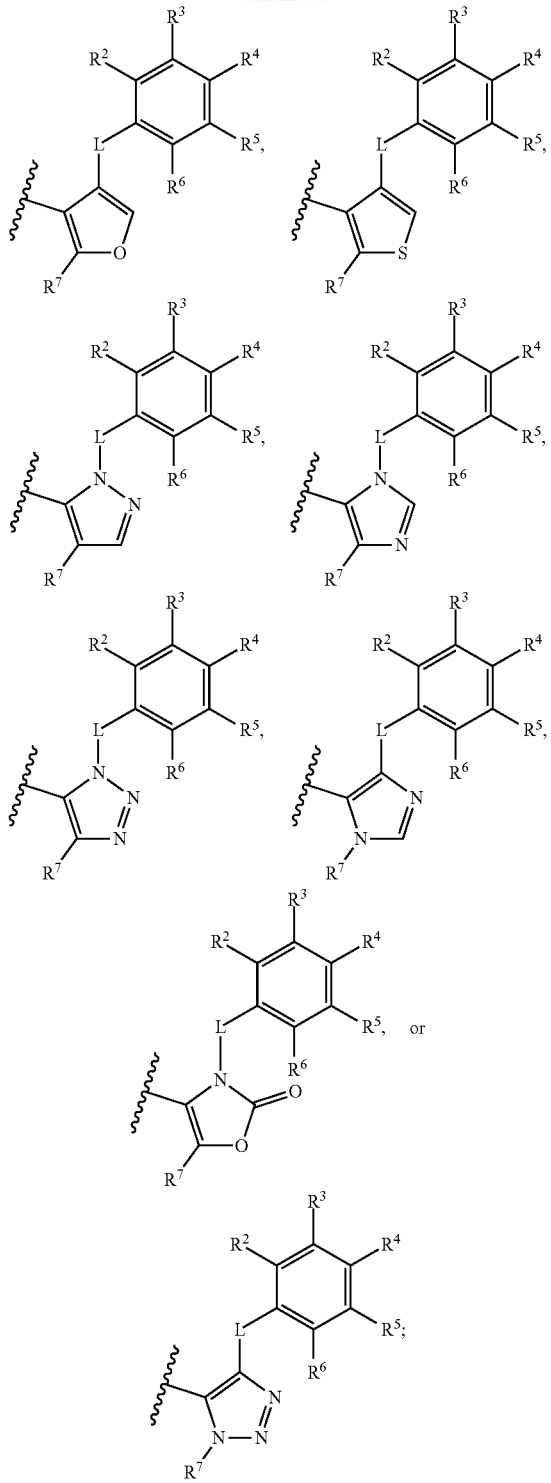

each L is independently a bond, —O—, —S—, —NH—, —CH$_2$—, —CH$_2$—CH$_2$—, —O—CH$_2$—, —O—CH$_2$—CH$_2$— or —CH$_2$—O—CH$_2$—;

each $R^2$, $R^3$, $R^4$, $R^5$ and $R^6$ is independently hydrogen, deuterium, F, Cl, Br, I, hydroxy, amino, nitro, cyano, $C_{1-3}$ alkyl, $C_{1-3}$ haloalkyl, $C_{1-3}$ alkoxy or $C_{1-3}$ haloalkoxy;

each $R^7$ is independently hydrogen, deuterium, F, Cl, Br, I, hydroxy, amino, nitro, cyano, $C_{1-6}$ alkyl, $C_{1-6}$ hydroxyalkyl, $C_{1-6}$ haloalkyl, $C_{1-6}$ alkoxy, $C_{1-6}$ alkylamino, $C_{1-6}$ alkoxy-$C_{1-6}$ alkyl, $C_{3-6}$ cycloalkyl or $C_{2-6}$ heterocyclyl, and wherein the $C_{3-6}$ cycloalkyl and $C_{2-6}$ heterocyclyl is independently and optionally substituted with substituents selected from F, Cl, Br, I, hydroxy, amino, nitro and cyano;
m is 0, 1, 2, 3 or 4;
n is 0, 1 or 2; and
each t is independently 0, 1 or 2;
with the proviso that a compound having formula (I) is not:
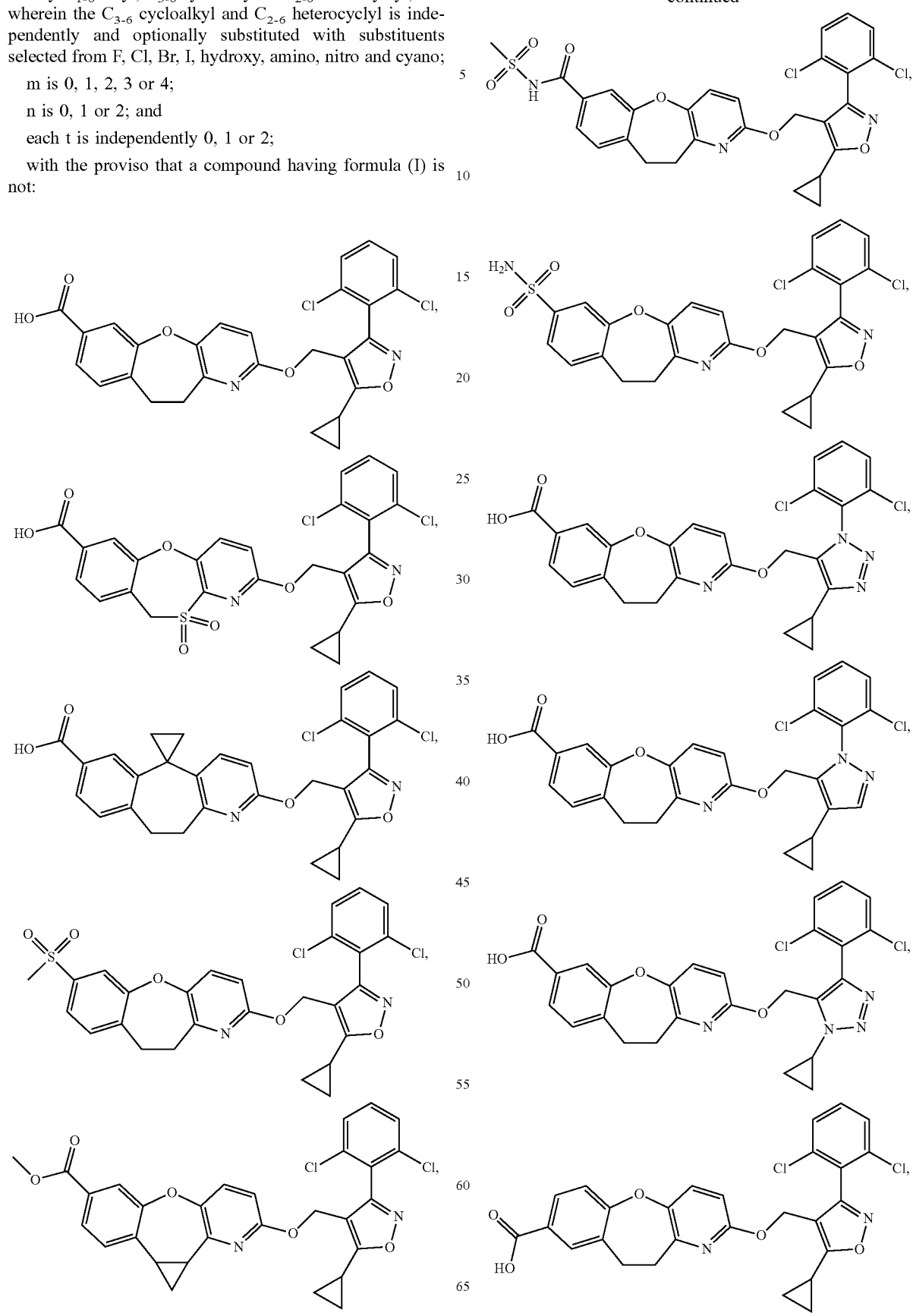

-continued

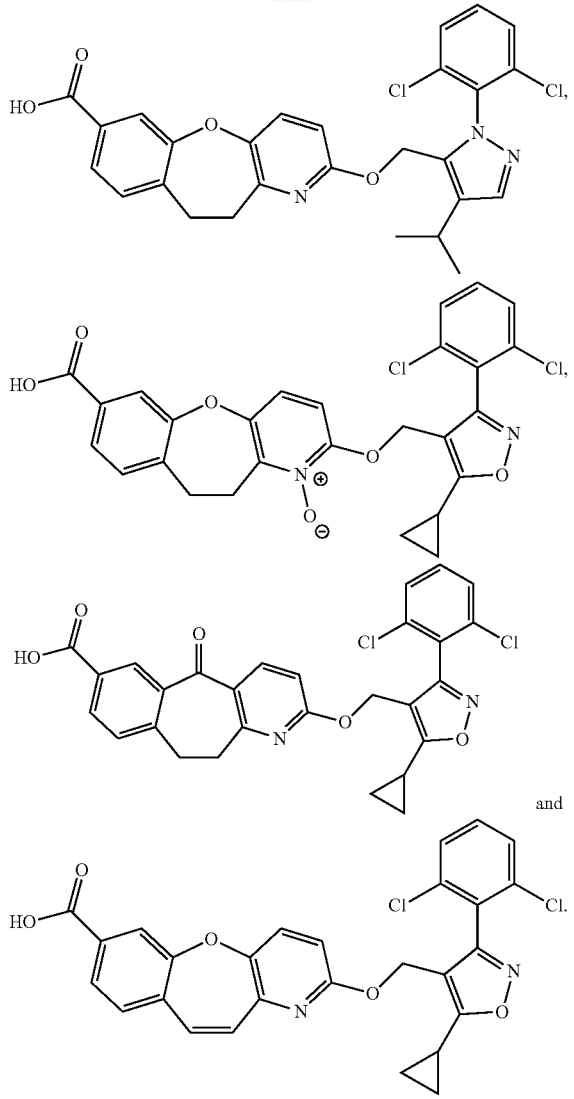

and

In some embodiments, each $R^x$ is independently hydrogen, deuterium, $C_{1-6}$ alkyl, $C_{1-6}$ aminoalkyl, $C_{1-6}$ haloalkyl, $C_{3-6}$ cycloalkyl, $C_{2-6}$ heterocyclyl, phenyl, halo-substituted phenyl or benzyl.

In other embodiments, each $R^x$ is independently hydrogen, deuterium, methyl, ethyl, isopropyl, aminomethyl, difluoromethyl, trifluoromethyl, cyclopropyl, cyclohexyl, tetrahydropyranyl, piperidinyl, phenyl, halo-substituted phenyl or benzyl.

In some embodiments, each $R^y$ and $R^z$ is independently hydrogen, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{2-6}$ alkenyl, $C_{2-6}$ alkynyl, $C_{3-6}$ cycloalkyl, $C_{2-6}$ heterocyclyl, phenyl, halo-substituted phenyl or benzyl; or $R^y$ and $R^z$ together with the same carbon atom to which they are attached, independently and optionally form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl.

In other embodiments, each $R^y$ and $R^z$ is independently hydrogen, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{2-4}$ alkenyl, $C_{2-4}$ alkynyl, $C_{3-6}$ cycloalkyl, $C_{2-6}$ heterocyclyl, phenyl, halo-substituted phenyl or benzyl; or $R^y$ and $R^z$ together with the same carbon atom to which they are attached, independently and optionally form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl.

In other embodiments, each $R^y$ and $R^z$ is independently hydrogen, deuterium, F, Cl, Br, I, hydroxy, amino, nitro, cyano, methyl, ethyl, n-propyl, isopropyl, difluoromethyl, trifluoromethyl, 2,2-difluoroethyl, 2,2,2-trifluoroethyl, hydroxymethyl, 2-hydroxyethyl, aminomethyl, methoxy, ethoxy, isopropoxy, t-butoxy, methylamino, dimethylamino, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, halo-substituted phenyl or benzyl; or $R^y$ and $R^z$, together with the same carbon atom to which they are attached, independently and optionally form cyclopropane, cyclobutane, cyclopentane, cyclohexane, azetidine, tetrahydrofuran, pyrrolidine, piperidine, piperazine, tetrahydropyran, morpholine or thiomorpholine, and wherein the cyclopropane, cyclobutane, cyclopentane, cyclohexane, azetidine, tetrahydrofuran, pyrrolidine, piperidine, piperazine, tetrahydropyran, morpholine and thiomorpholine is independently and optionally substituted with substituents selected from F, Cl, Br, I, hydroxy, amino, nitro, cyano, methyl, ethyl, isopropyl and trifluoromethyl.

In some embodiments, each of $R^h$ and $R^k$ is independently methyl, ethyl, isopropyl or trifluoromethyl; or $R^h$ and $R^k$ together with the carbon atoms to which they are attached, form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl.

In other embodiments, each of $R^h$ and $R^k$ is independently methyl, ethyl, isopropyl or trifluoromethyl; or $R^h$ and $R^k$ together with the carbon atoms to which they are attached, form cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinylene or thiomorpholinylene, and wherein the cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinylene and thiomorpholinylene is independently and optionally substituted with substituents selected from F, Cl, Br, I, hydroxy, amino, nitro, cyano, methyl, ethyl, isopropyl and trifluoromethyl.

In some embodiments, each $R^1$ is independently hydrogen, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy, $C_{1-6}$ alkoxy-$C_{1-3}$ alkyl, $C_{2-6}$ alkenyl, $C_{2-6}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, $-L^1-C(=O)OR^8$, $-L^1-S(=O)_tR^9$, $-O-L^2-C(=O)OR$, $-O-L^2-S(=O)_tR^9$, $-C(=O)NR^{10}R^{11}$, $-C(=O)N(R^{10})S(=O)_2R^9$, $-C(=NR^{10})NR^{10}R^{11}$, $-C(=O)N(R^{10})-L^3-S(=O)_2OR^8$, $-C(=O)N(R^{10})C(=O)OR^8$ or $-C(=O)N(R^{10})-L^3-C(=O)OR$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each $R^1$ is independently and optionally substituted with one or more $R^{12}$;

wherein, each $L^1$, $L^2$, $L^3$, t, $R^8$, $R^9$, $R^{10}$, $R^{11}$ and $R^{12}$ is as defined herein.

In other embodiments, each $R^1$ is independently hydrogen, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy, $C_{1-3}$ alkoxy-$C_{1-3}$ alkyl, $C_{2-4}$ alkenyl, $C_{2-4}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, -$L^1$-C(=O)O$R^8$, -$L^1$-S(=O)$_t R^9$, —O-$L^2$-C(=O)OR, —O-$L^2$-S(=O)$_t R^9$, —C(=O)N$R^{10}R^{11}$, —C(=O)N($R^{10}$)S(=O)$_2 R^9$, —C(=N$R^{10}$)N$R^{10}R^{11}$, —C(=O)N($R^{10}$)-$L^3$-S(=O)$_2 O R^8$, —C(=O)N($R^{10}$)C(=O)O$R^8$ or —C(=O)N($R^{10}$)-$L^3$-C(=O)O$R^8$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each said $R^1$ is independently and optionally substituted with one or more $R^{12}$;

wherein, each $L^1$, $L^2$, $L^3$, t, $R^8$, $R^9$, $R^{10}$, $R^{11}$ and $R^{12}$ is as defined herein.

In other embodiments, each $R^1$ is independently hydrogen, deuterium, F, Cl, Br, I, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxylmethyl, isopropoxylmethyl, ethenyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—$C_{1-3}$ alkyl, —C(=O)NHS(=O)$_2$—$C_{1-3}$ alkyl, —C(=O)NHS(=O)$_2$-phenyl, —C(=O)NH—$C_{1-3}$ alkylene-S(=O)$_2$OH, —C(=O)NH—$C_{1-3}$ alkylene-C(=O)OH, —S(=O)$_2$NH$_2$, —S(=O)$_2$OH, —S(=O)$_2$—$C_{1-3}$ alkyl, —C(=O)NH$_2$ or —C(=O)N(CH$_3$)$_2$; wherein each $R^1$ is independently and optionally substituted with one or more $R^{12}$;

wherein, each $R^{12}$ is as defined herein.

In some embodiments, each $R^8$ is independently hydrogen, deuterium, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl or phenyl.

In other embodiments, each $R^8$ is independently hydrogen, deuterium, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl or phenyl.

In some embodiments, each $R^9$ is independently hydrogen, deuterium, hydroxy, amino, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl, phenyl or —N$R^{10}R^{11}$;

wherein, each $R^{10}$ and $R^{11}$ is as defined herein.

In other embodiments, each $R^9$ is independently hydrogen, deuterium, hydroxy, amino, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl, phenyl or —N$R^{10}R^{11}$;

wherein, each $R^{10}$ and $R^{11}$ is as defined herein.

In some embodiments, each $R^{10}$ is independently hydrogen, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-6}$ heterocyclyl or phenyl.

In other embodiments, each $R^{10}$ is independently hydrogen, deuterium, $C_{1-3}$ alkyl, $C_{1-3}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or phenyl.

In some embodiments, each $R^{11}$ is independently hydrogen, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-6}$ heterocyclyl or phenyl.

In other embodiments, each $R^{11}$ is independently hydrogen, deuterium, $C_{1-3}$ alkyl, $C_{1-3}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or phenyl.

In some embodiments, $R^{10}$ and $R^{11}$ together with the nitrogen atom to which they are attached, independently and optionally form a $C_{2-6}$ heterocyclic ring or $C_{1-5}$ heteroaromatic ring.

In some embodiments, each $R^2$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy.

In some embodiments, each $R^3$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy.

In some embodiments, each $R^4$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy.

In some embodiments, each $R^5$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy.

In some embodiments, each $R^6$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy.

In some embodiments, each $R^7$ independently is hydrogen, deuterium, F, Cl, Br, I, hydroxy, amino, nitro, cyano, $C_{1-3}$ alkyl, $C_{1-3}$ hydroxyalkyl, $C_{1-3}$ haloalkyl, $C_{1-3}$ alkoxy, $C_{1-3}$ alkylamino, $C_{1-3}$ alkoxy-$C_{1-3}$ alkyl, $C_{3-6}$ cycloalkyl or $C_{2-6}$ heterocyclyl, and wherein the $C_{3-6}$ cycloalkyl and $C_{2-6}$ heterocyclyl is independently and optionally substituted with substituents selected from F, Cl, Br, I, hydroxy, amino, nitro and cyano.

In other embodiments, each $R^7$ is independently hydrogen, deuterium, F, Cl, Br, I, hydroxy, amino, nitro, cyano, methyl, ethyl, isopropyl, t-butyl, hydroxymethyl, 2-hydroxyisopropyl, difluoromethyl, trifluoromethyl, 2-fluoroisopropyl, methoxy, isopropoxy, t-butoxy, dimethylamino, isopropoxymethyl, t-butoxymethyl, cyclopropyl, cyclobutyl, cyclopentyl, cyclohexyl, tetrahydrofuranyl, pyrrolidinyl, piperidinyl, piperazinyl, morpholinyl or thiomorpholinyl, and wherein the cyclopropyl, cyclobutyl, cyclopentyl, cyclohexyl, tetrahydrofuranyl, pyrrolidinyl, piperidinyl, piperazinyl, morpholinyl and thiomorpholinyl is independently and optionally substituted with substituents selected from F, Cl, Br, I, hydroxy, amino, nitro and cyano.

In one aspect, provided herein is the compound having one of the following structures, or a stereoisomer, a geometric isomer, a tautomer, an N-oxide, a solvate, a hydrate, a metabolite, ester, a pharmaceutically acceptable salt or a prodrug thereof, but are not limited to:

(1)
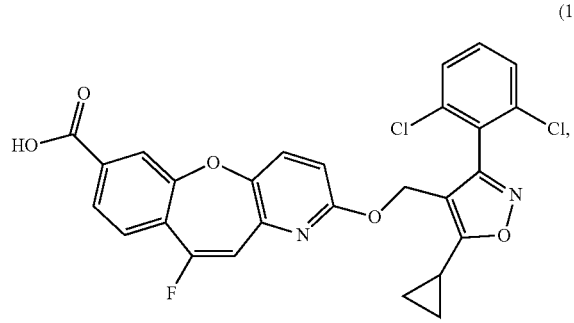
(2)
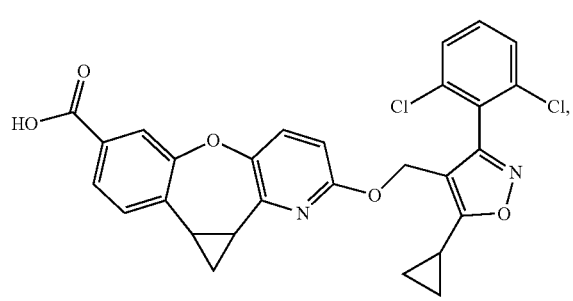
(3)
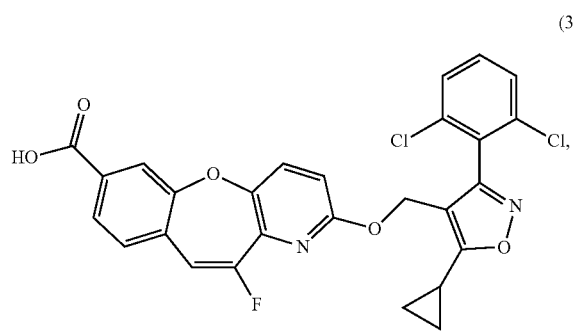
(4)
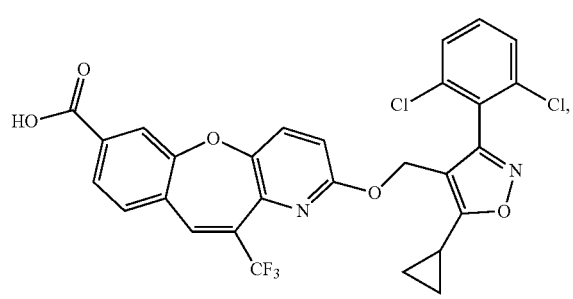
(5)
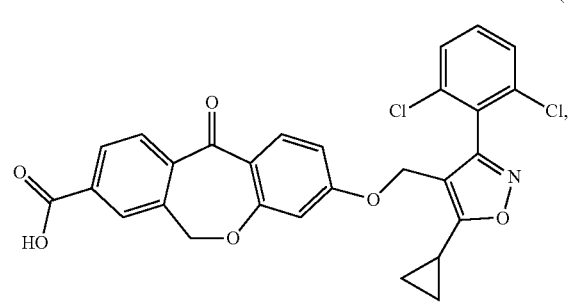
(6)
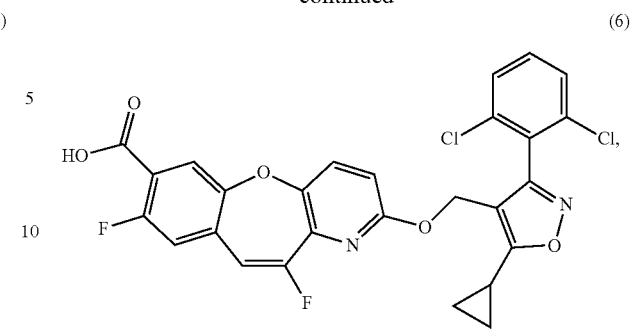
(7)
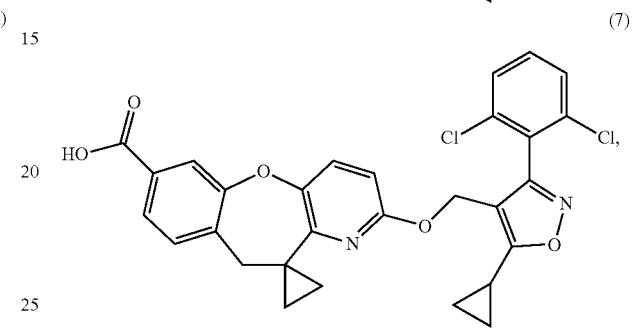
(8)
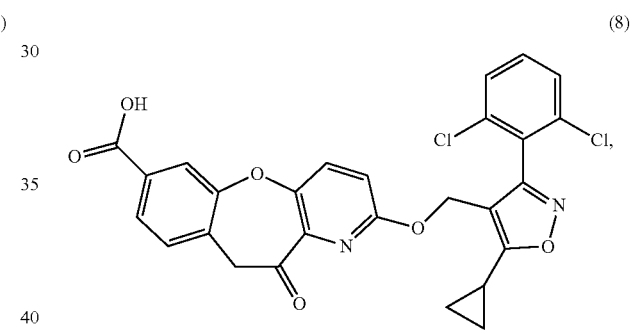
(9)
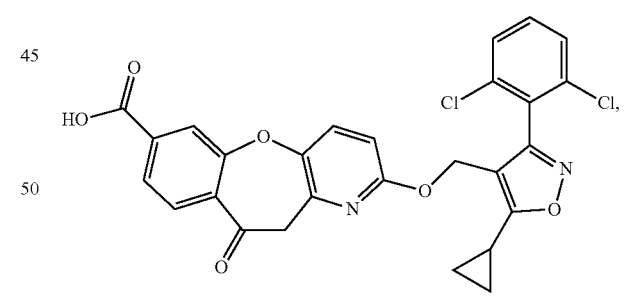
(10)
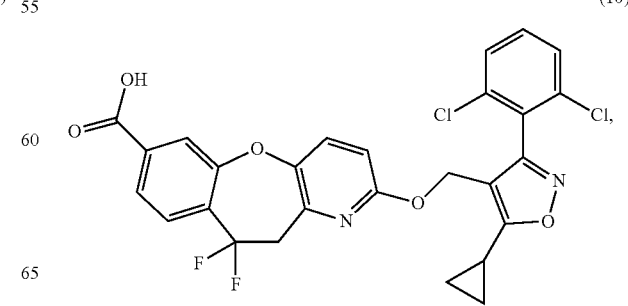

(11) 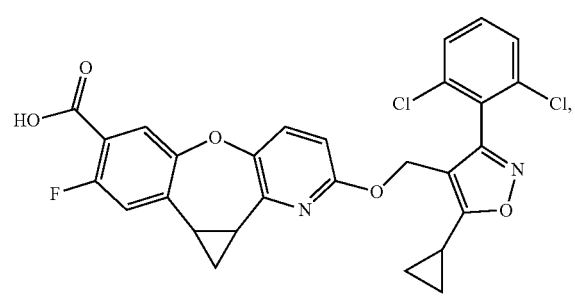
(12) 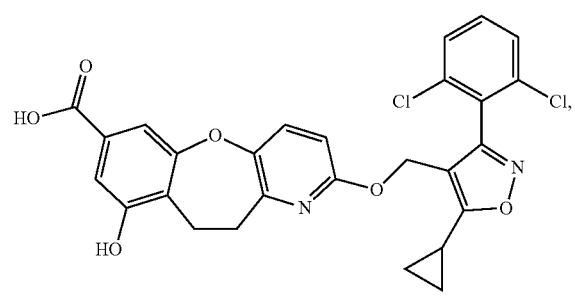
(13) 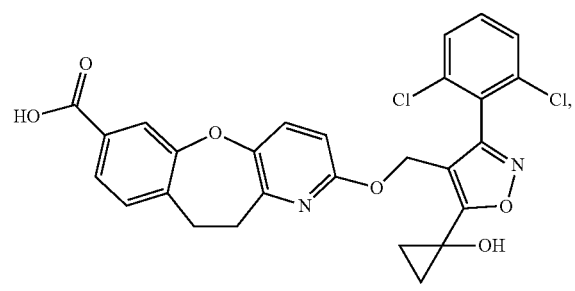
(14) 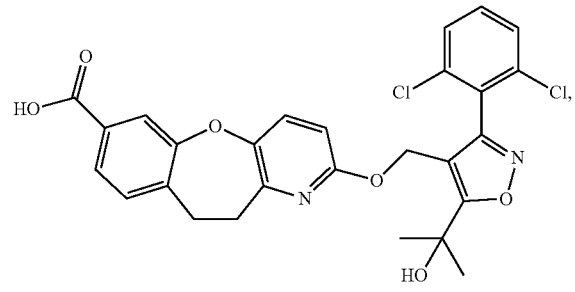
(15) 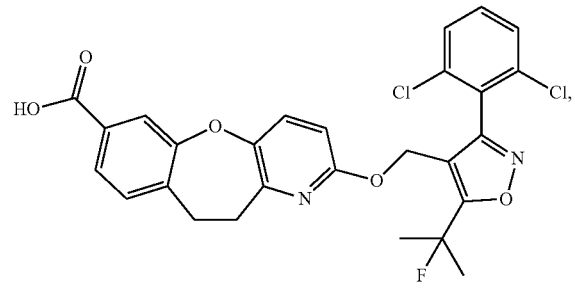
(16) 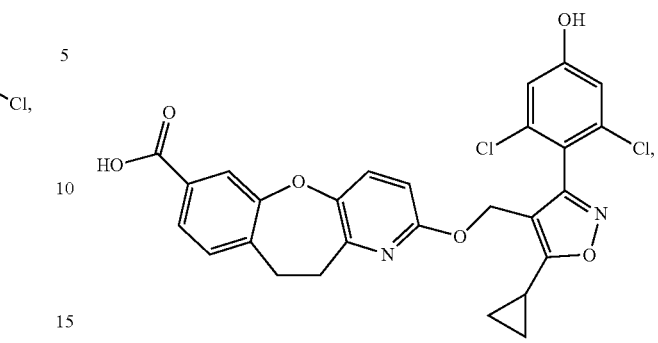
(17) 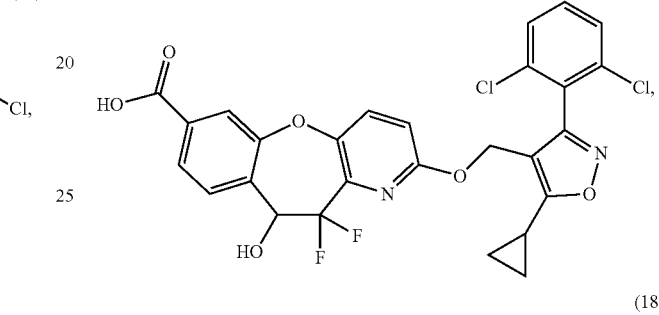
(18) 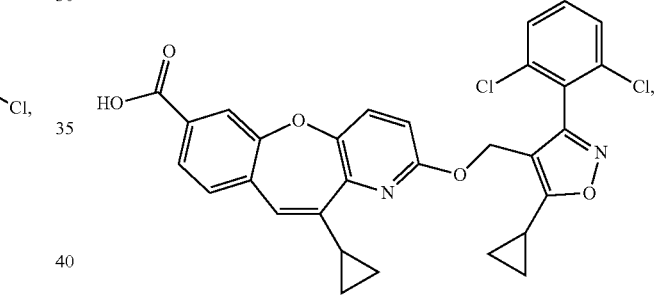
(19) 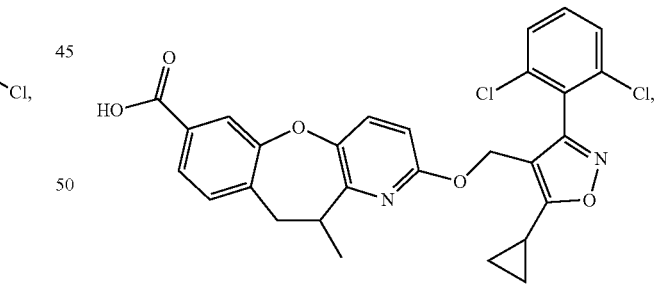
(20) 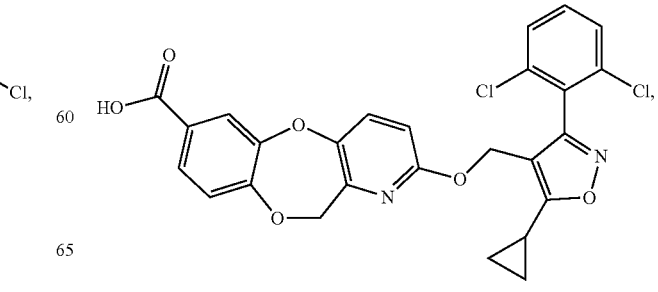

(21)
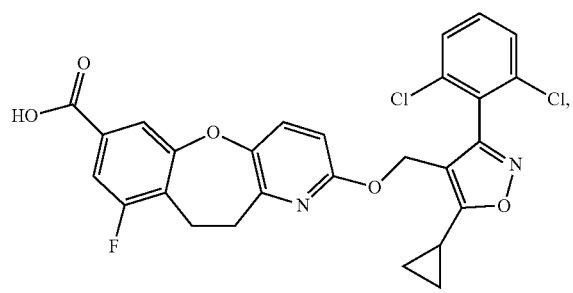
(22)
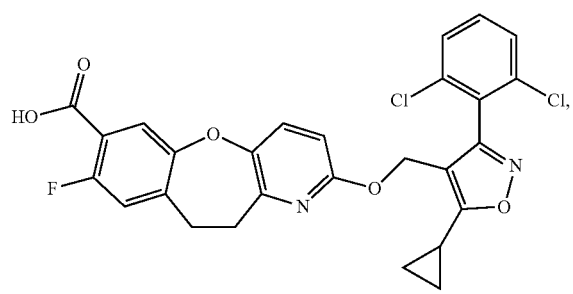
(23)
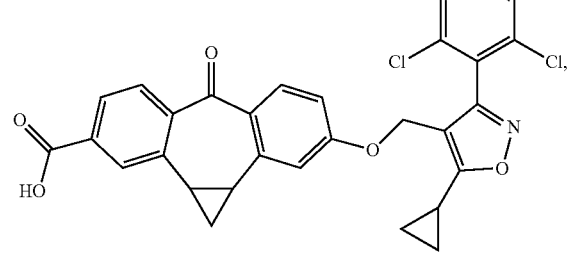
(24)
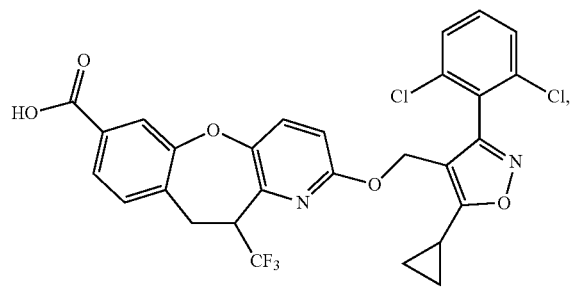
(25)
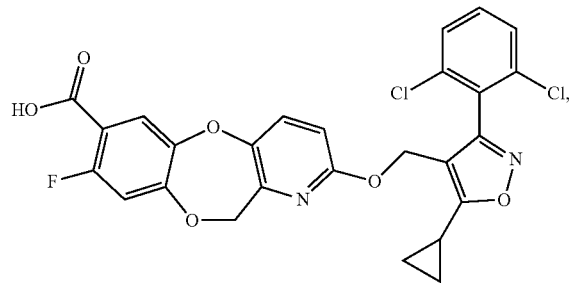
(26)
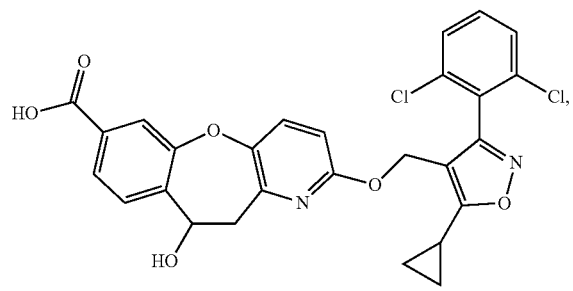
(27)
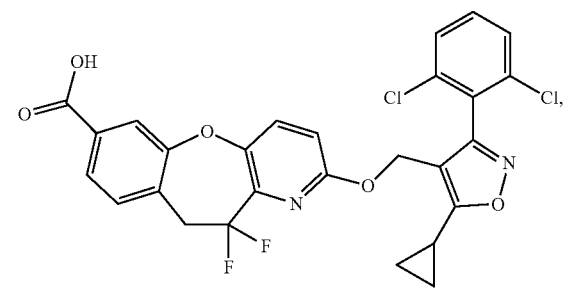
(28)
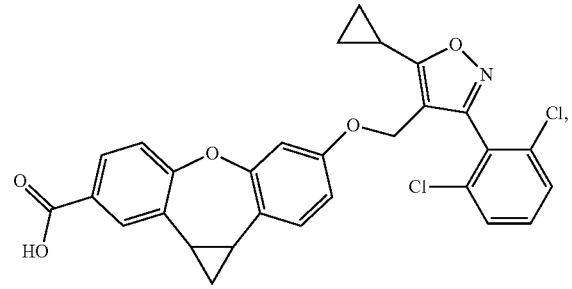
(29)
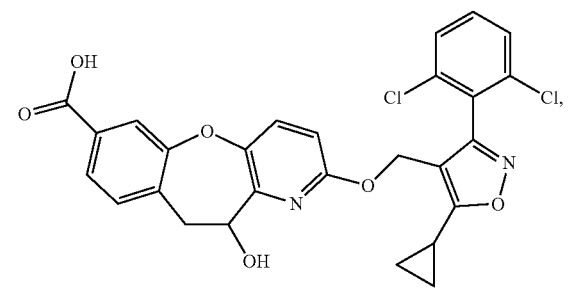
(30)
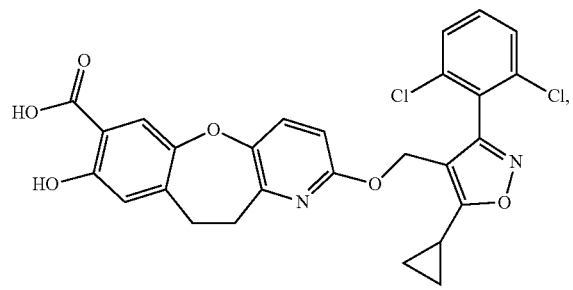

(31)
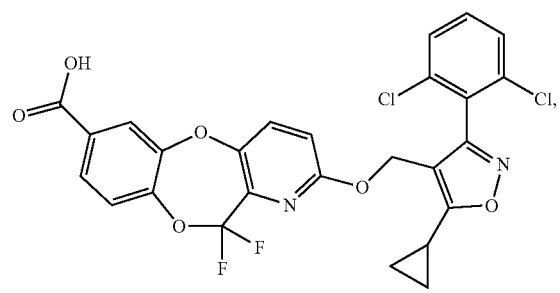
(32)
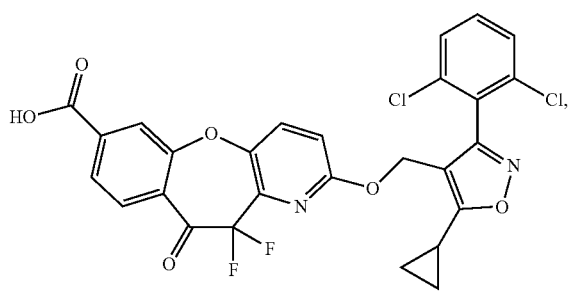
(33)
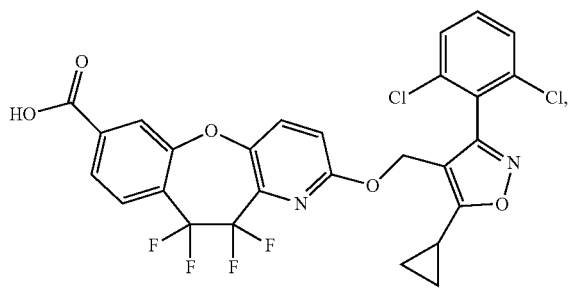
(34)
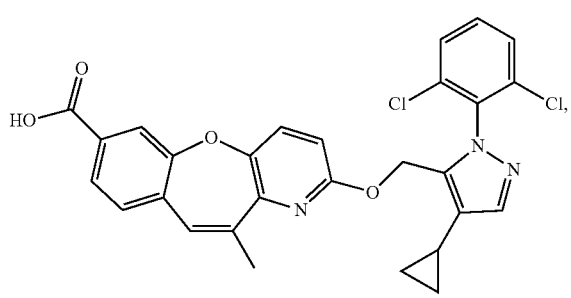
(35)
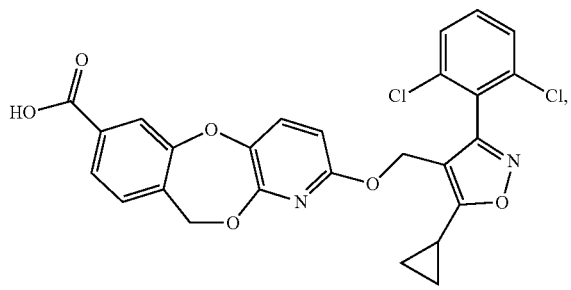
(36)
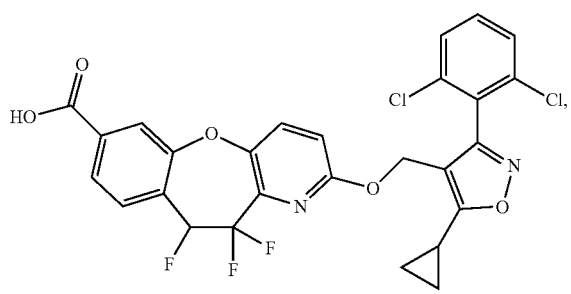
(37)
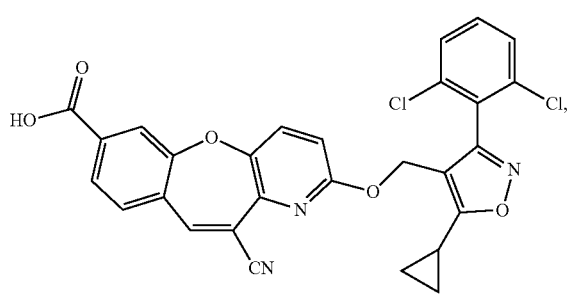
(38)
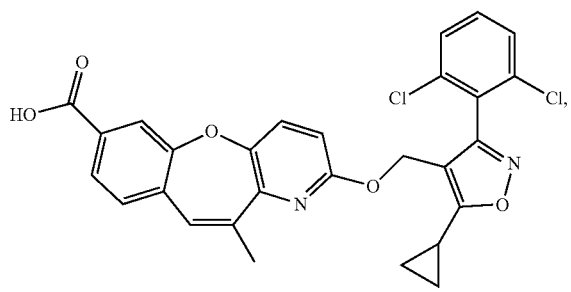
(39)
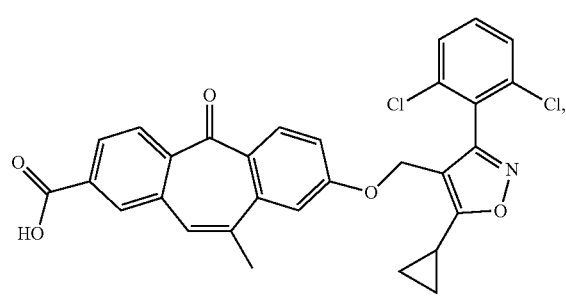
(40)
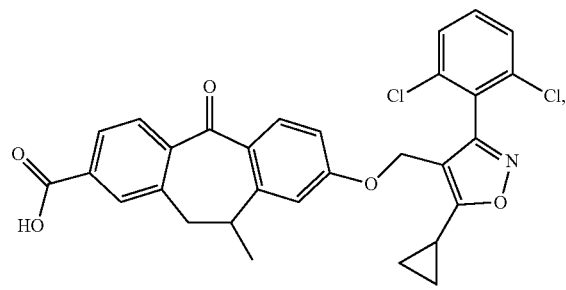

(41)
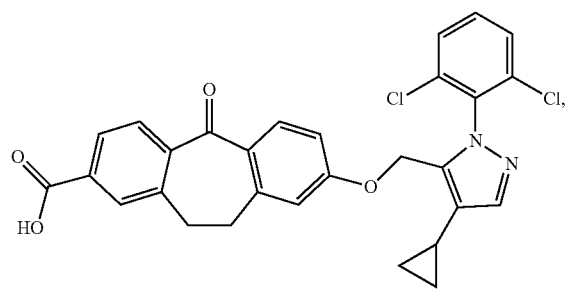
(42)
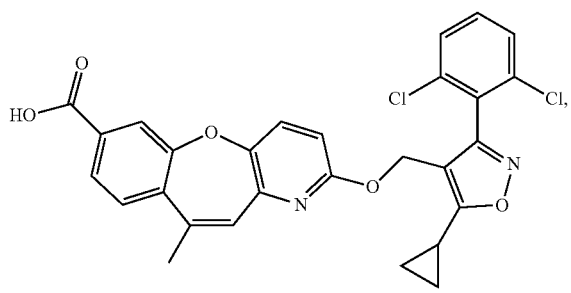
(43)
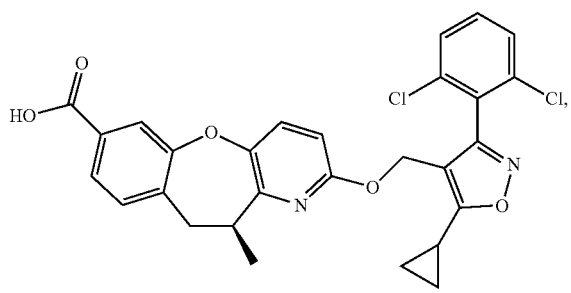
(44)
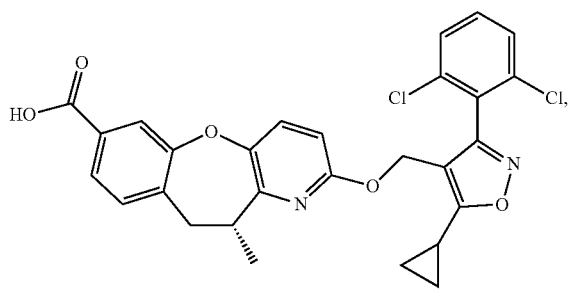
(45)
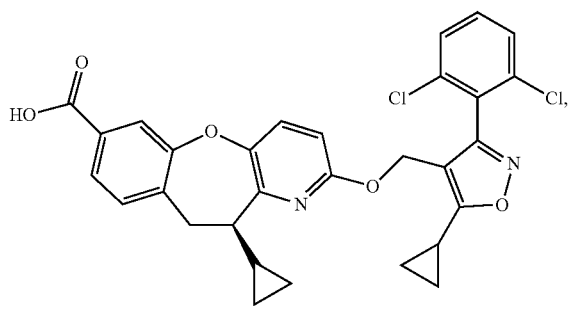
(46)
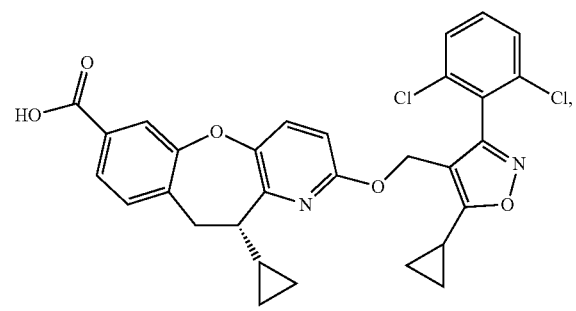
(47)
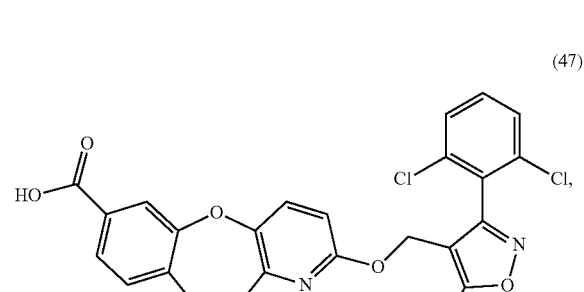
(48)
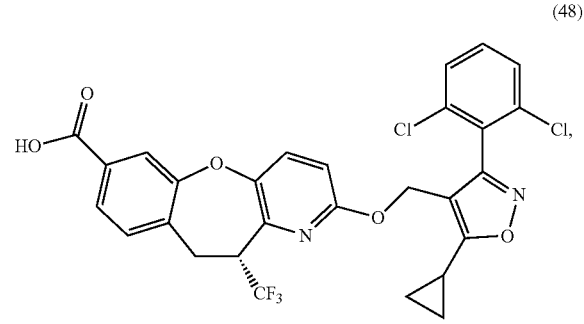
(49)
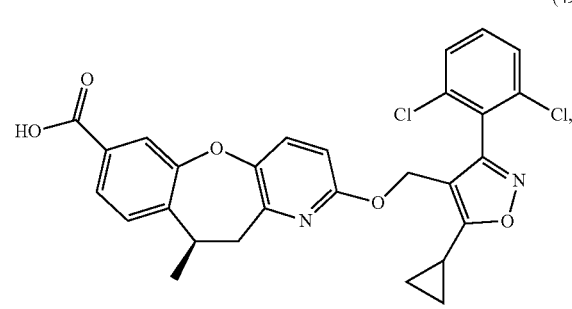
(50)
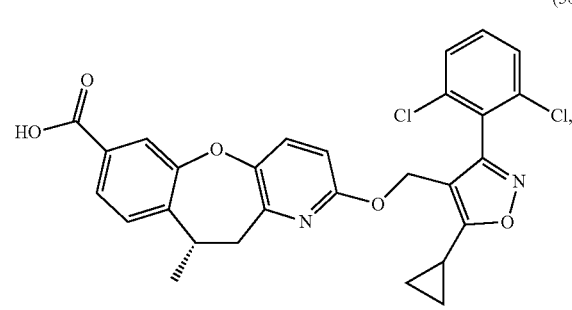

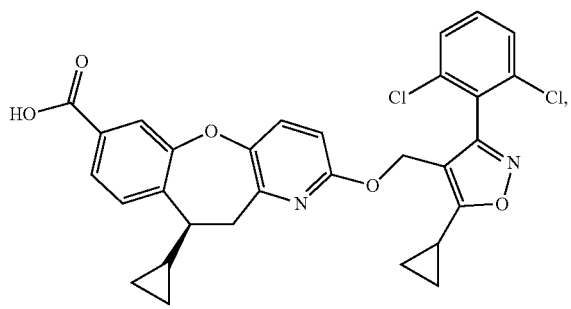
(51)

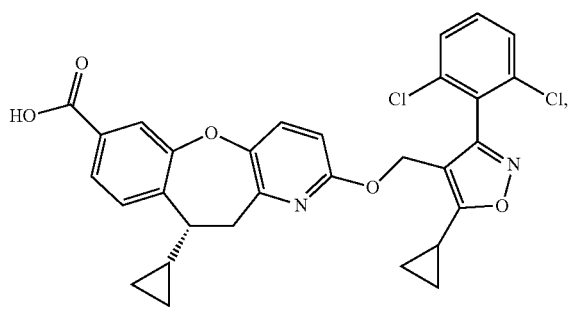
(52)

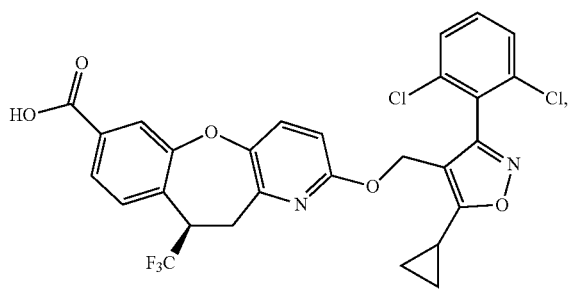
(53)

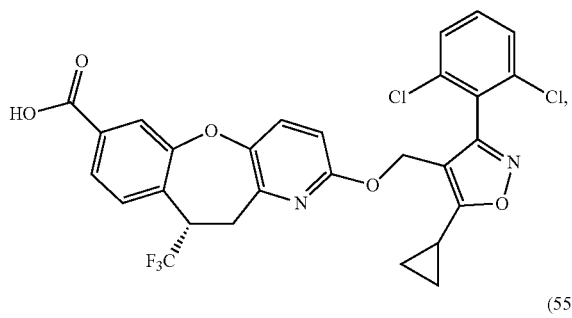
(54)

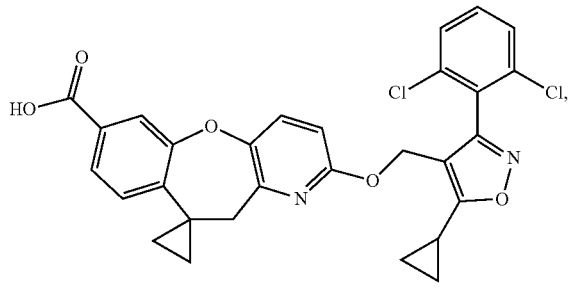
(55)

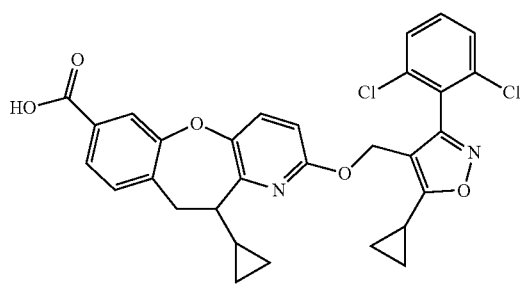
(56)

and

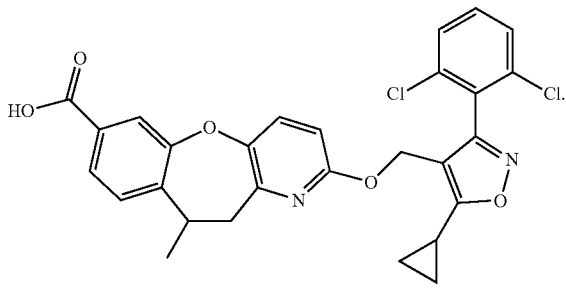
(57)

In one aspect, provided herein is a pharmaceutical composition comprising the compound described above, and the pharmaceutical composition optionally further comprise a pharmaceutically acceptable carrier, excipient, diluent, adjuvant, vehicle or a combination thereof.

In one aspect, provided herein is use of the compound described above in the manufacture of a medicament for preventing, managing, treating or lessening a disease mediated by FXR in a patient.

In some embodiments, the disease mediated by FXR is a cardiovascular and cerebrovascular disease, a disease related to dyslipidemia, metabolic syndrome, a hyperproliferative disease, fibrosis, an inflammatory disease or a hepatobiliary related disease.

In some embodiments, the cardiovascular and cerebrovascular disease is atherosclerosis, acute myocardial infarction, veno-occlusive disease, portal hypertension, pulmonary hypertension, heart failure, peripheral arterial occlusive disease (PAOD), sexual dysfunction, stroke or thrombosis.

In some embodiments, the metabolic syndrome is insulin resistance, hyperglycemia, hyperinsulinemia, elevated blood level of fatty acids or glycerol, hyperlipidemia, obesity, hypertriglyceridemia, hypercholesterolemia, X syndrome, diabetic complications, atherosclerosis, hypertension, acute anemia, neutropenia, dyslipidemia, type II diabetes, diabetic nephropathy, diabetic neuropathy, diabetic retinopathy or the merger disorders of diabetes and abnormally high body mass index (BMI).

In some embodiments, the hyperproliferative disease is hepatocellular carcinoma, colonic adenoma, polyposis, colonic adenocarcinoma, breast cancer, membrane cancer, Barrett's esophageal cancer and other forms of gastrointestinal tract disease or liver tumor.

In some embodiments, the fibrosis, inflammatory disease and hepatobiliary related disease is nonalcoholic fatty liver disease (NAFLD), nonalcoholic steatohepatitis (NASH), cholestasis, liver fibrosis, primary biliary cirrhosis (PBC), primary sclerosing cholangitis (PSC), progressive familial intrahepatic cholestasis (PFIC), cystic fibrosis, drug-induced bile duct injury, cirrhosis of the liver, hepatitis B, sebaceous disease, cirrhosis of the liver caused by alcohol, biliary obstruction, cholelithiasis, colitis, newborn yellow disease, riboflavin disease prevention or intestinal bacterial overgrowth.

In one aspect, provided herein is a method of preventing, managing, treating or lessening a disease mediated by FXR comprising administering to the patient a therapeutic effective amount of the compound or the pharmaceutical composition of the present invention.

In some embodiments, the disease mediated by FXR is a cardiovascular and cerebrovascular disease, a disease related to dyslipidemia, metabolic syndrome, a hyperproliferative disease, fibrosis, an inflammatory disease or a disease related to liver and gallbladder.

In some embodiments, the cardiovascular and cerebrovascular disease is atherosclerosis, acute myocardial infarction, veno-occlusive disease, portal hypertension, pulmonary hypertension, heart failure, peripheral arterial occlusive disease (PAOD), sexual dysfunction, stroke or thrombosis.

In some embodiments, the metabolic syndrome is insulin resistance, hyperglycemia, hyperinsulinemia, elevated blood level of fatty acids or glycerol, hyperlipidemia, obesity, hypertriglyceridemia, hypercholesterolemia, X syndrome, diabetic complications, atherosclerosis, hypertension, acute anemia, neutropenia, dyslipidemia, type II diabetes, diabetic nephropathy, diabetic neuropathy, diabetic retinopathy or the merger disorders of diabetes and abnormally high BMI.

In some embodiments, the hyperproliferative disease is hepatocellular carcinoma, adenomatous, polyposis, colon cancer, breast cancer, membrane cancer, Barrett's esophageal cancer and other forms of gastrointestinal tract disease or liver tumor.

In some embodiments, inflammatory disease and disease related to liver and gallbladder is nonalcoholic fatty liver disease (NAFLD), nonalcoholic steatohepatitis (NASH), cholestasis, liver fibrosis, primary biliary cirrhosis (PBC), primary sclerosing cholangitis (PSC), progressive familial intrahepatic cholestasis (PFIC), cystic fibrosis, drug-induced bile duct injury, gallstones, cirrhosis of liver, hepatitis B, sebaceous disease, cirrhosis of the liver caused by alcohol, biliary obstruction, cholelithiasis, colitis, newborn yellow disease, riboflavin disease prevention or intestinal bacterial overgrowth.

In one aspect, provided herein is the compound or the pharmaceutical composition of the present invention for use in preventing, managing, treating or lessening a disease mediated by FXR in a patient.

In some embodiments, the disease mediated by FXR is a cardiovascular and cerebrovascular disease, a disease related to dyslipidemia, metabolic syndrome, a hyperproliferative disease, fibrosis, an inflammatory disease or a disease related to liver and gallbladder.

In some embodiments, the cardiovascular and cerebrovascular disease is atherosclerosis, acute myocardial infarction, veno-occlusive disease, portal hypertension, pulmonary hypertension, heart failure, peripheral arterial occlusive disease (PAOD), sexual dysfunction, stroke or thrombosis.

In some embodiments, the metabolic syndrome is insulin resistance, hyperglycemia, hyperinsulinemia, elevated blood level of fatty acids or glycerol, hyperlipidemia, obesity, hypertriglyceridemia, hypercholesterolemia, X syndrome, diabetic complications, atherosclerosis, hypertension, acute anemia, neutropenia, dyslipidemia, type II diabetes, diabetic nephropathy, diabetic neuropathy, diabetic retinopathy or the merger disorders of diabetes and abnormally high BMI.

In some embodiments, the hyperproliferative disease is hepatocellular carcinoma, adenomatous, polyposis, colon cancer, breast cancer, membrane cancer, Barrett's esophageal cancer and other forms of gastrointestinal tract disease or liver tumor;

In some embodiments, inflammatory disease and disease related to liver and gallbladder is nonalcoholic fatty liver disease (NAFLD), nonalcoholic steatohepatitis (NASH), cholestasis, liver fibrosis, primary biliary cirrhosis (PBC), primary sclerosing cholangitis (PSC), progressive familial intrahepatic cholestasis (PFIC), cystic fibrosis, drug-induced bile duct injury, gallstones, cirrhosis of liver, hepatitis B, sebaceous disease, cirrhosis of the liver caused by alcohol, biliary obstruction, cholelithiasis, colitis, newborn yellow disease, riboflavin disease prevention or intestinal bacterial overgrowth.

In one aspect, provided herein is a method of preventing, managing, treating or lessening a disease mediated by FXR comprising administering a therapeutic effective amount of the compound or the pharmaceutical composition of the present invention to the patient.

In one aspect, provided herein is a method of preventing, managing, treating or lessening a disease mediated by FXR comprising administering a pharmaceutically acceptable effective dosage of the compounds of the present invention to the patient.

In other aspect, provided herein is a method of preparing, separating or purifying the compound of Formula (I).

Pharmaceutical Compositions, Preparations, Administration, and Uses of the Compounds and Pharmaceutical Compositions In other aspect, the characteristics of the pharmaceutical composition of the present invention include compound of formula (I), compound listed in the present invention, or one or more compounds of examples 1-19, and a pharmaceutically acceptable carrier, adjuvant or vehicle. The effective amount of the compound in the composition of the present invention is capable of treating or lessening disease mediated by FXR in the patients.

It will also be appreciated that the compounds disclosed herein can exist in free form, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable composition disclosed herein further comprises a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. As described in the following references: In Remington: The Science and Practice of Pharmacy, 21st ed., 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, both of which are herein incorporated by reference in their entireties, and discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

The compound of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycol, oils, alcohols, fragrances, preservative, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations, such as, for example, powders, hard capsules and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dose will be obtained. The active compounds can also be administered intranasally as, for example, liquid drops or spray.

The tablets, pills, capsules and the like may also contain a binder (such as gum tragacanth, acacia, corn starch or gelatin); excipients (such as dicalcium phosphate); a disintegrant agent (such as corn starch, potato starch, alginic acid); a lubricant (such as magnesium stearate); and a sweetening agent (such as sucrose, lactose or saccharin). When a dosage unit form is a capsule, it may contain, in addition to materials of the above type, a liquid carrier (such as a fatty oil).

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl or propylparaben as preservatives, a dye and a flavoring (such as cherry or orange flavor).

Ophthalmic formulations, eye ointments, powders, solutions and the like, are also contemplated as being within the scope of this invention.

The compounds of the present invention may also be administered parenterally. Solutions or suspensions of these active compounds can be prepared suitably mixed with a surfactant (e.g., hydroxyl-propylcellulose) in water. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation. In all cases, the form must be sterile and must be fluid to the extent easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols and the like. Preferably compounds of the present invention are administered orally.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

When treating or preventing of conditions mediated by FXR for which compounds of the present invention are indicated, generally satisfactory results are obtained when the compounds of the present invention are administered at a daily dose of from about 0.1 milligrams to about 100 milligrams per kilogram of animal body weight, preferably given as a single daily dose or in divided doses two to six times a day, or in sustained release form. For most large mammals, the total daily dose is from about 1.0 milligrams to about 1000 milligrams, preferably from about 1.0 milligrams to about 50 milligrams. In the case of a 70 kg human, the total daily dose will generally from about 7.0 milligrams to about 350 milligrams. This dosage regimen may be adjusted to provide the optimal therapeutic response.

The present invention relates to compounds, compositions, or a pharmaceutically acceptable salt or hydrate thereof for effective use in preventing, managing, treating or alleviating a disease mediated by the FXR, particularly effective in the treatment of non-alcoholic fatty liver (NAFLD), nonalcoholic steatohepatitis (NASH), obesity, hypertriglyceridemia, atherosclerosis, chronic intrahepatic cholestasis, primary biliary cirrhosis (PBC), primary sclerosing cholangitis (PSC), progressive familial intrahepatic cholestasis (PFIC), drug-induced bile duct injury, gallstones, cirrhosis, hepatitis B, steatosis, cirrhosis of the liver caused by alcohol, cystic fibrosis, biliary obstruction, gallstone disease, liver fibrosis, dyslipidemia, atherosclerosis, type II diabetes, diabetic nephropathy, diabetic neuropathy, diabetic retinopathy, peripheral arterial occlusive disease (PAOD), colitis, newborn yellow disease, riboflavin disease prevention, vein occlusive disease, portal hypertension, metabolic syndrome, acute myocardial infarction, acute stroke, thrombosis, hypercholesterolemia, intestinal bacterial overgrowth, erectile dysfunction, gastrointestinal tumor and liver tumor.

General Synthetic Procedures

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz or 600 MHz spectrometer using $CDCl_3$, $d_6$-DMSO, $CD_3OD$ or $d_6$-acetone as solvents (reported in ppm), and using TMS (0 ppm) or chloroform (7.25 ppm) as the reference standard. For multiple peaks, the following abbreviations used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-$C_{18}$, 2.1×30 mm, 5 m column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were shown in Table 1:

TABLE 1

| The gradient condition of the mobile phase in Low-resolution mass spectrum analysis | | |
|---|---|---|
| Time (min) | A ($CH_3CN$, 0.1% HCOOH) | B ($H_2O$, 0.1% HCOOH) |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-$C_{18}$, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
$CDCl_3$ chloroform-d
DMF N,N-dimethylformamide
DMSO dimethylsulfoxide
DMSO-$d_6$ dimethyl sulfoxide-$d_6$
$CD_3OD$ methyl alcohol-$d_4$
MeOH methanol
THF tetrahydrofuran
DCM difluoromethane
EtOAc, EA ethyl acetate
PE petroleum ether
Pd/C, Pd—C Palladium on activated carbon
g gramme
mg milligramme
$H_2O$ water
M mole/liter
mol mole
mmol millimole
mL milliliter
μL microliter
MPa million Pascal
rt room temperature Typical synthetic procedures for preparing the compounds of the present invention disclosed are shown in the following synthetic schemes. Unless otherwise specified, $R^1$, T, X, Y, Z, $R^a$, $R^b$, $R^c$, $R^y$, $R^z$, m and n are as defined herein.

Schemes

Scheme 1

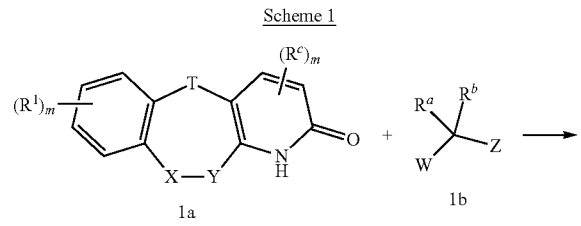

-continued

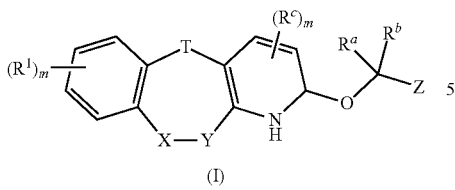

(I)

W is a leaving group, including, but are not limited to, halogen, methyl sulfonyloxy, p-methyl phenylsulfonyloxy, and the like.

The substitution reaction of compound 1a with compound 1b can afford Compound (I) under an alkaline condition. The bases include but are not limited to potassium phosphate, and the like. The reaction can be carried out in an insert solvent. The solvents include but are not limited to N,N-dimethylformamide, and the like.

Scheme 2

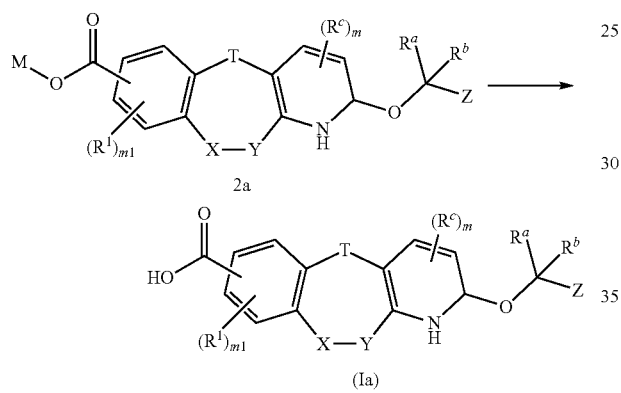

M is alkyl, m1 is 0, 1, 2 or 3.

By hydrolysis reaction, compound 2a can be converted to compound (Ia). The hydrolysis reaction can refer to "Protective Groups in Organic Synthesis".

Scheme 3

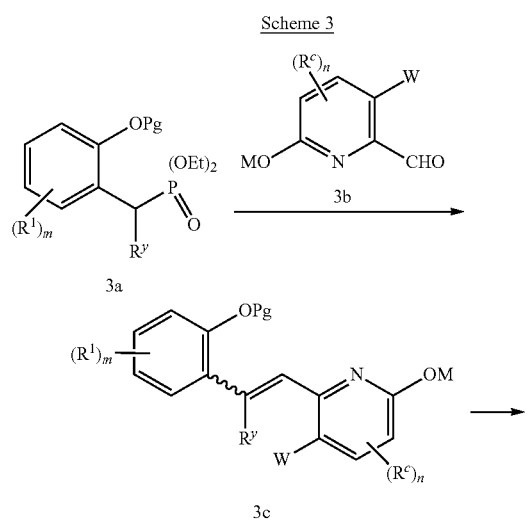

-continued

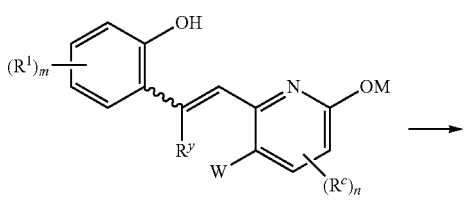

3d

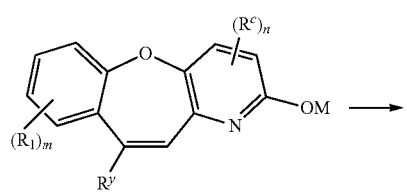

3e

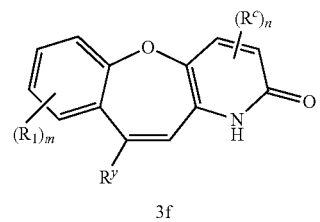

3f

M is alkyl, W is a leaving group, include but is not limited to halogen, methyl sulfonyloxy, p-methyl phenylsulfonyloxy, and the like. Pg is a protecting group defined herein.

Homer-Wadsworth-Emmons reaction between compound 3a and compound 3b can afford compound 3c. In Homer-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

The hydroxy protecting group of compound 3c can be removed to afford compound 3d. The removal of hydroxy protecting group can refer to "Protective Groups in Organic Synthesis".

By coupling reaction in the presence of a catalyst and a ligand under an alkaline condition, compound 3d can be converted to compound 3e. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound 3e can be removed to afford compound 3f. The removal of hydroxy protecting group can refer to "Protective Groups in Organic Synthesis".

Scheme 4

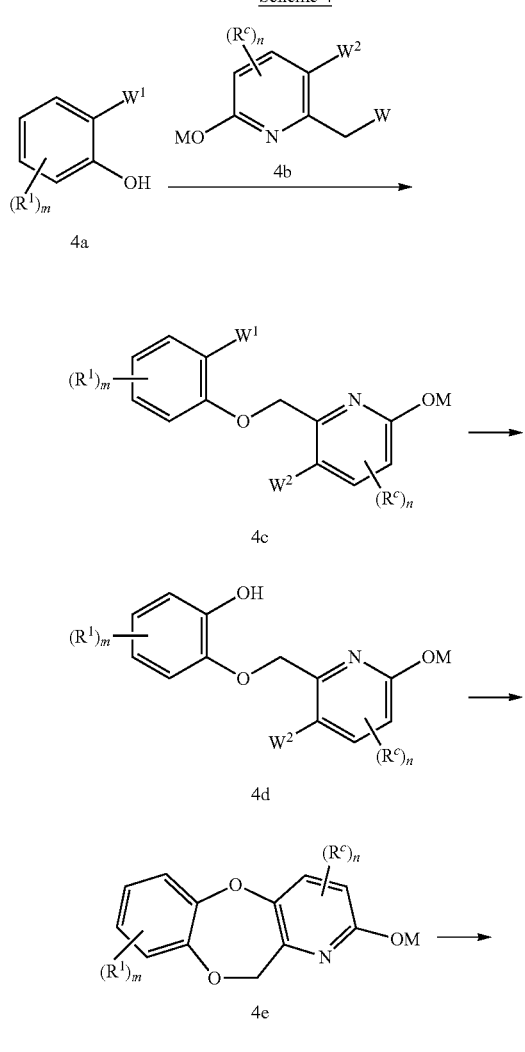

M is alkyl; each of W, W$^1$ and W$^2$ is independently a leaving group, including but not limited to halogen, methyl sulfonyloxy, p-methyl phenylsulfonyloxy, and the like.

The substitution reaction of compound 4a with compound 4b can afford Compound 4c under an alkaline condition. The bases include but are not limited to potassium phosphate, and the like. The reaction is carried out in an insert solvent. The solvents include but are not limited to N,N-dimethylformamide, and the like.

By coupling reaction in the presence of a catalyst and a ligand under an alkaline condition, compound 4c can be converted to compound 4d. The catalysts include, but are not limited to, cuprous iodide, and the like. The ligands include, but are not limited to, 1,10-phenanthroline, and the like. The bases include, but are not limited to, potassium hydroxide, and the like. The reaction can be carried out in an inert solvent. The solvents include, but are not limited to, dimethylsulfoxide, water or mixed solvent and the like.

By coupling reaction in the presence of a catalyst and a ligand under an alkaline condition, compound 4d can be converted to compound 4e. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound 4e can be removed to afford compound 4f. The removal of hydroxy protecting group can refer to "Protective Groups in Organic Synthesis".

Scheme 5

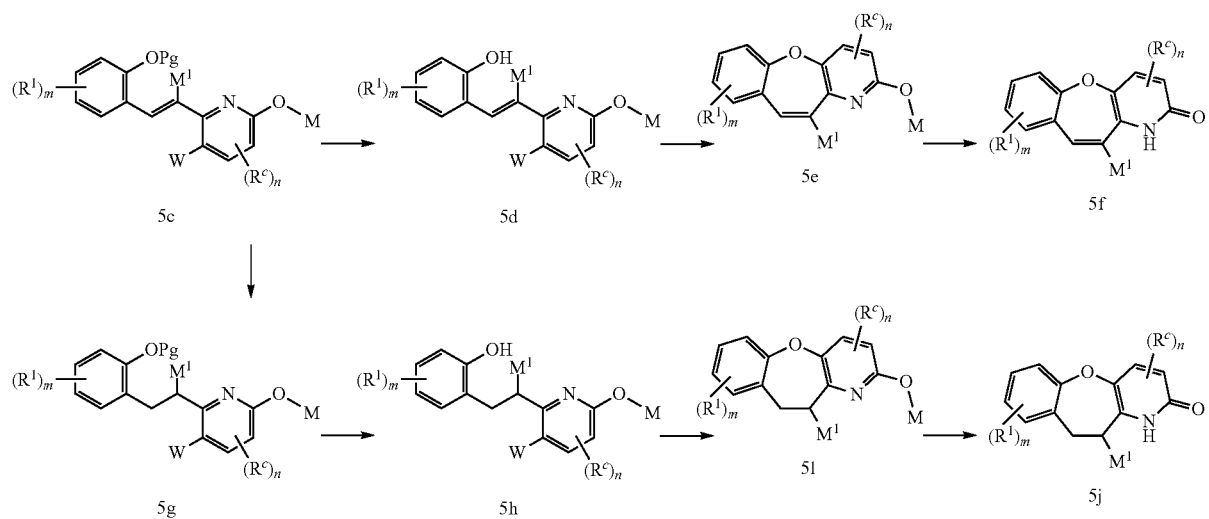

M is alkyl; W is a leaving group, including but not limited to halogen, methyl sulfonyloxy, p-methyl phenylsulfonyloxy, and the like. $M^1$ is hydrogen, alkyl, haloalkyl or cycloalkyl.

Homer-Wadsworth-Emmons reaction between compound 5a and compound 5b can afford compound 5c. In Homer-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

The hydroxy protecting group of compound 5e can be removed to afford compound 5d. The removal of hydroxy protecting group can refer to "Protective Groups in Organic Synthesis".

By coupling reaction in the presence of a catalyst and a ligand under an alkaline condition, compound 5d can be converted to compound 5e. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound 5e can be removed to afford compound 5f. The removal of hydroxy protecting group can refer to "Protective Groups in Organic Synthesis".

Compound 5c can be reduced to afford compound 5g in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

The hydroxy protecting group of compound 5g can be removed to afford compound 5h). The removal of hydroxy protecting group can refer to "Protective Groups in Organic Synthesis".

By coupling reaction in the presence of a catalyst and a ligand under an alkaline condition, compound 5h can be converted to compound 5i. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound 5i can be removed to afford compound 5j. The removal of hydroxy protecting group can refer to "Protective Groups in Organic Synthesis".

The cyclization reaction of compound 5e with a methylating agent can afford compound 5k. The methylating agents include, but are not limited to, trimethyl iodide sulfoxide, and the like. The reaction can be carried out in an inert solvent. The solvents include, but are not limited to, dimethyl sulfoxide, and the like.

Compound 5k can be converted to compound 5l by removing hydroxy protecting groups, and the removal of hydroxy protecting groups can refer to "Protective Groups in Organic Synthesis".

Scheme 6

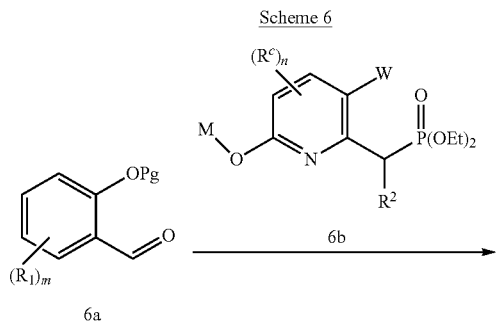

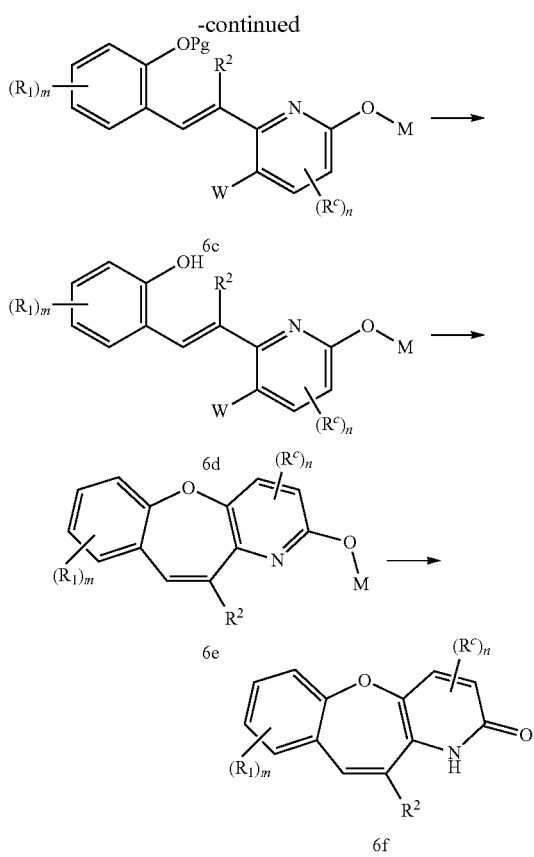

M is alkyl; Pg is a protecting group defined herein; W is a leaving group, including but not limited to halogen, methyl sulfonyloxy, p-methyl phenylsulfonyloxy, and the like.

Homer-Wadsworth-Emmons reaction between compound 6a and compound 6b can afford compound 6c. In Homer-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

Compound 6c can be converted to compound 6d by removing hydroxy protecting groups, and the removal of hydroxy protecting groups can refer to "Protective Groups in Organic Synthesis".

By coupling reaction in the presence of a catalyst and a ligand under an alkaline condition, compound 6d can be converted to compound 6e. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound 6e can be converted to compound 6f by removing hydroxy protecting groups, and the removal of hydroxy protecting groups can refer to "Protective Groups in Organic Synthesis".

Scheme 7

-continued

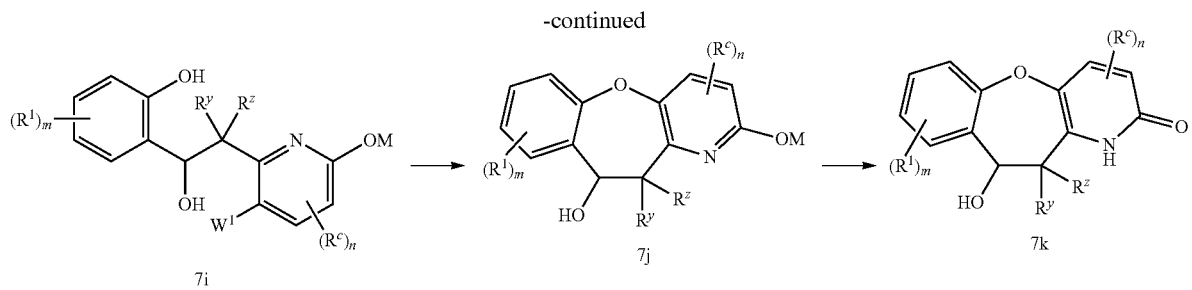

M is alkyl; Pg is a protecting group defined herein; $W^1$ is a leaving group, including but not limited to halogen, methyl sulfonyloxy, p-methyl phenylsulfonyloxy, and the like.

The reaction of compound 7a with compound 7b can afford Compound 7c under an alkaline condition. The bases include but are not limited to, sodium bis(trimethylsilyl) amide, and the like. The reaction is carried out in an insert solvent. The solvents include but are not limited to tetrahydrofuran, and the like.

The substitution reaction of compound 7c with haloalkanes or halogenating agents can afford Compound 7d under an alkaline condition. The haloalkanes include but are not limited to 1,2-dibromoethane. The halogenating agents include but are not limited to N-fluorobenzenesulfonimide. The bases include but are not limited to sodium hydroxide, sodium bis(trimethylsilyl)amide, and the like. The reaction is carried out in an insert solvent. The solvents include but are not limited to toluene, tetrahydrofuran, and the like.

Compound 7d can be converted to compound 7e by removing hydroxy protecting groups, and the removal of hydroxy protecting groups can refer to "Protective Groups in Organic Synthesis".

The reaction of compound 7e with methylchloroformate can afford intermediate active ester under an alkaline condition. Then the active ester can be further reduced to obtain compound 7f. The bases include but are not limited to triethylamine, and the like. The reducing agents include but are not limited to sodium borohydride, and the like. The reaction is carried out in an insert solvent. The solvents include but are not limited to tetrahydrofuran, and the like.

By coupling reaction in the presence of a catalyst and a ligand under an alkaline condition, compound 7f can be converted to compound 7g. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound 7g can be converted to compound 7h by removing hydroxy protecting groups, and the removal of hydroxy protecting groups can refer to "Protective Groups in Organic Synthesis".

Compound 7i can be obtained by a reaction of compound 7e with a reducing agent. The reducing agent includes, but is not limited to sodium borohydride, and the like. The reaction can be carried out in an inert solvent. The solvents include, but are not limited to, tetrahydrofuran, and the like.

By coupling reaction in the presence of a catalyst and a ligand under an alkaline condition, compound 7i can be converted to compound 7j. The catalysts include, but are not limited to, cuprous iodide, and the like. The ligands include, but are not limited to, N,N-dimethylglycine, and the like.

The bases include, but are not limited to, cesium carbonate, and the like. The reaction can be carried out in an inert solvent. The solvents include, but are not limited to, 1,4-dioxane, and the like.

Compound 7j can be converted to compound 7k by removing hydroxy protecting groups, and the removal of hydroxy protecting groups can refer to "Protective Groups in Organic Synthesis".

Scheme 8

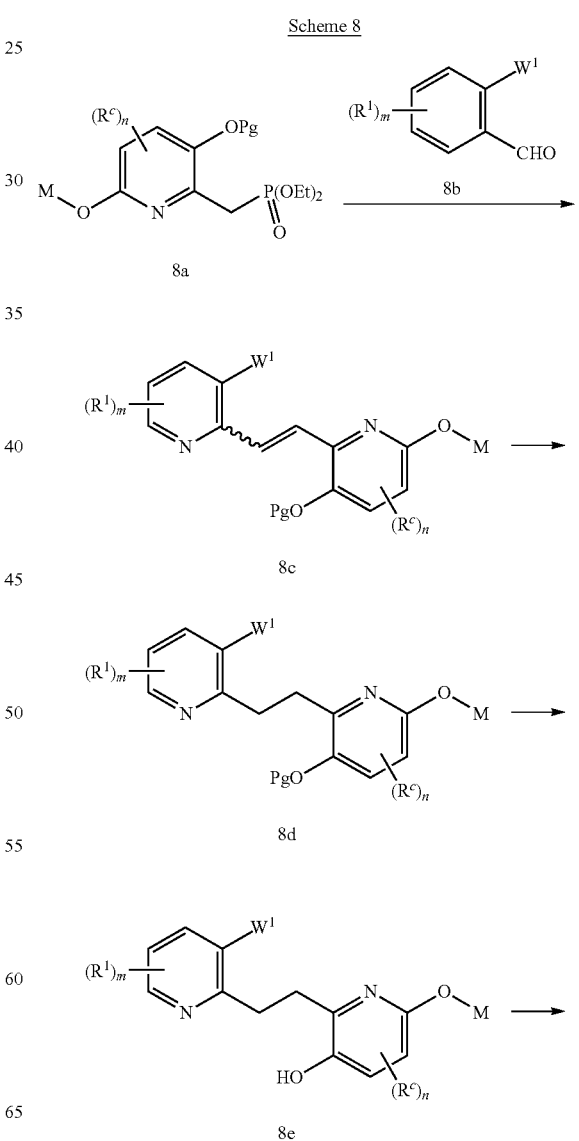

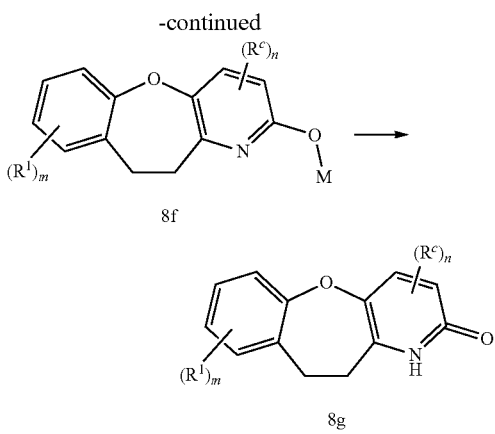

M is alkyl; Pg is a protecting group defined herein; W¹ is a leaving group, including but not limited to halogen, methyl sulfonyloxy, p-methyl phenylsulfonyloxy, and the like.

Horner-Wadsworth-Emmons reaction between compound 8a and compound 8b can afford compound 8c. In Horner-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

Compound 8c can be reduced to afford compound 8d in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

Compound 8d can be converted to compound 8e by removing hydroxy protecting groups, and the removal of hydroxy protecting groups can refer to "Protective Groups in Organic Synthesis".

By coupling reaction in the presence of a catalyst and a ligand under an alkaline condition, compound 8e can be converted to compound 8f. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound 8f can be converted to compound 8g by removing hydroxy protecting groups, and the removal of hydroxy protecting groups can refer to "Protective Groups in Organic Synthesis".

Scheme 9

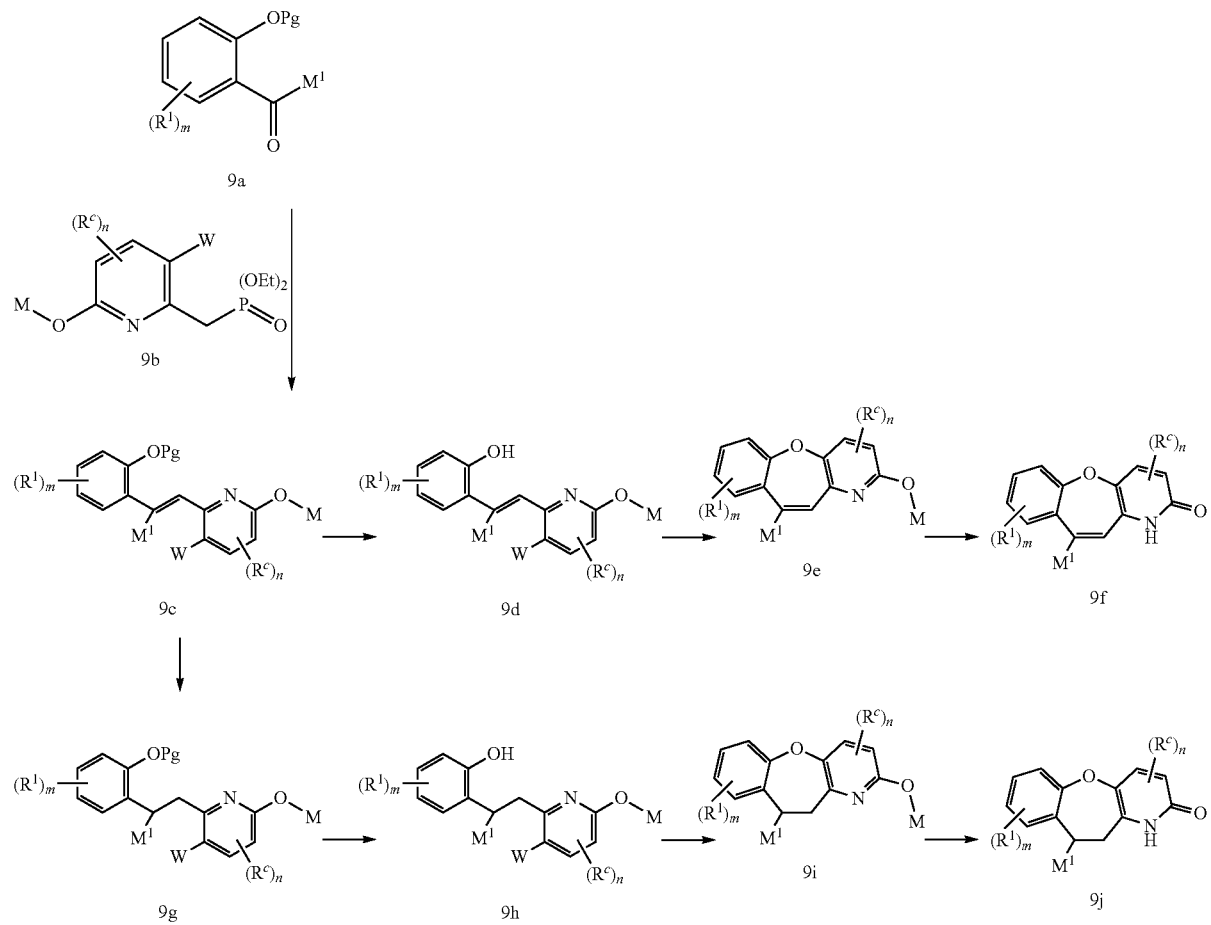

M is alkyl; W is a leaving group, including but not limited to halogen, methyl sulfonyloxy, p-methyl phenylsulfonyloxy, and the like. $M^1$ is hydrogen, alkyl, haloalkyl or cycloalkyl.

Horner-Wadsworth-Emmons reaction between compound 9a and compound 9b can afford compound 9c. In Horner-Wadsworth-Emmons reaction, the reaction starting materials can be reacted in the presence of a base (e.g., sodium hydride, potassium t-butoxide, etc.) in a solvent. The reaction can be preferably carried out in an inert solvent. The solvents include, but are not limited to, tetrahydrofuran, and the like.

Compound 9c can be converted to compound 9d by removing hydroxy protecting groups, and the removal of hydroxy protecting groups can refer to "Protective Groups in Organic Synthesis".

By coupling reaction in the presence of a catalyst and a ligand under an alkaline condition, compound 9d can be converted to compound 9e. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

Compound 9e can be converted to compound 9f by removing hydroxy protecting groups, and the removal of hydroxy protecting groups can refer to "Protective Groups in Organic Synthesis".

Compound 9c can be reduced to afford compound 9g in the presence of a reducing agent under an alkaline condition. The reducing agents include, but are not limited to, p-methyl benzenesulfonohydrazide, and the like. The bases include, but are not limited to, sodium acetate, and the like. The reaction can be carried out in an inert solvent. The solvents include, but are not limited to, tetrahydrofuran, water or a mixed solvent, and the like.

The hydroxy protecting group of compound 9 can be removed to afford compound 9h). The removal of hydroxy protecting group can refer to "Protective Groups in Organic Synthesis".

By coupling reaction in the presence of a catalyst and a ligand under an alkaline condition, compound 9h can be converted to compound 9i. The catalysts include, but are not limited to, cuprous iodide, and the like. The ligands include, but are not limited to, N,N-dimethylglycine, and the like. The bases include, but are not limited to, cesium carbonate, and the like. The reaction can be carried out in an inert solvent. The solvents include, but are not limited to, 1,4-dioxane, and the like.

The hydroxy protecting group of compound 9i can be removed to afford compound 9j. The removal of hydroxy protecting group can refer to "Protective Groups in Organic Synthesis".

The following examples disclosed herein are presented to further describe the invention. However, these examples should not be used to limit the scope of the invention.

DESCRIPTION OF THE PREFERRED EMBODIMENTS

Examples

Example 1: 2-((5-cyclopropyl-3-(2,6-dichlorophenyl)isoxazol-4-yl)methoxy)-10-fluorobenzo oxepino [3,2-b]pyridine-7-carboxylic acid

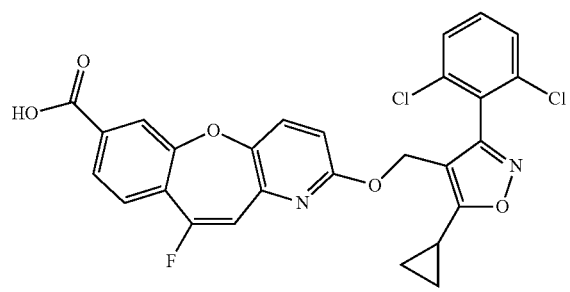 [SMILES: O=C(O)c1ccc2c(c1)Oc1ccc(OCc3c(-c4c(Cl)cccc4Cl)noc3C3CC3)nc1C=C2F]

Step 1: methyl 3-acetoxy-4-methylbenzoate

To a mixture of methyl 3-hydroxy-4-methylbenzoate (4.3 g, 26 mmol) and pyridine (3.5 mL, 43 mmol) in dichloromethane (50 mL) was added acetic anhydride (4.0 mL, 43 mmol) under an ice bath. Water (50 mL) was added to quench the reaction after the reaction mixture was stirred for 5 h at rt. The resulting mixture was extracted with dichloromethane (50 mL×2). The combined organic layers were washed with hydrochloric acid (1 M), dried over anhydrous sodium sulfate, filtered and concentrated under reduced pressure. The residue was purified by column chromatography eluted with PE/EA (v/v=10/1) to give the title compound as colourless oil (5.3 g, 98%).

Step 2: methyl 3-acetoxy-4-(bromomethyl)benzoate

To a mixture of methyl 3-acetoxy-4-methylbenzoate (5.3 g, 25.5 mmol) and N-bromosuccinimide (4.6 g, 25.7 mmol) in tetrachloromethane (100 mL) was added azodiisobutyronitrile (210 mg, 1.3 mmol). Then the mixture was heated to reflux for 5 h. The reaction mixture was cooled to rt and concentrated under reduced pressure. The residue was purified by column chromatography eluted with PE/EA (v/v=20/1) to give the title compound as colourless oil (5.7 g, 77%).

Step 3: methyl 3-acetoxy-4-((diethoxyphosphoryl)methyl)benzoate

A mixture of methyl 3-acetoxy-4-(bromomethyl)benzoate (5.6 g, 20 mmol) in triethyl phosphite (10 mL) was heated at 150° C. and stirred overnight. Then the reaction mixture was cooled to rt and concentrated to remove triethyl phosphite. The residue was purified by column chromatography eluted with dichloromethane/methanol (v/v=10/1) to give the title compound as colourless oil (6.7 g, 100%).

Step 4: methyl 4-((diethoxyphosphoryl)methyl)-3-hydroxybenzoate

To a mixture of methyl 3-acetoxy-4-((diethoxyphosphoryl)methyl)benzoate (6.5 g, 19 mmol) in methanol (100 mL) was added aqueous potassium carbonate (30 mL, 30 mmol, 1.0 M). Then the reaction mixture was stirred for 1 h at rt and concentrated to remove most of methanol. The residue was diluted with water (20 mL), extracted with ethyl acetate (50 mL×2). The combined organic layers were combined, washed with saturated brine (10 mL), dried over anhydrous sodium sulfate, filtered and concentrated. The residue was purified by column chromatography on a silica gel eluted with PE/EA (v/v=2/1) to give the title compound as a white solid (5.2 g, 91%).

MS (ESI, pos. ion) m/z: 303.2 [M+H]$^+$.

Step 5: methyl 4-((diethoxyphosphoryl)methyl)-3-(methoxymethoxy)benzoate

To a mixture of methyl 4-((diethoxyphosphoryl)methyl)-3-hydroxybenzoate (5.2 g, 17 mmol) and diisopropylethylamine (6.0 mL, 34 mmol) in dichloromethane (60 mL) was added chloromethyl methyl ether (2.3 mL, 30 mmol) under an ice bath. The reaction mixture was stirred at rt overnight. The reaction was quenched with water (50 mL), extracted with dichloromethane (50 mL×2), washed with saturated brine (10 mL), dried over anhydrous sodium sulfate, filtered and concentrated in vacuo. The residue was purified by column chromatography eluted with PE/EA (v/v=4/1) to give the title compound as colourless oil (3.8 g, 64%).

MS (ESI, pos. ion) m/z: 347.2 [M+H]$^+$.

Step 6: methyl 4-((diethoxyphosphoryl)fluoromethyl)-3-(methoxymethoxy)benzoate

To a mixture of methyl 4-((diethoxyphosphoryl)methyl)-3-(methoxymethoxy)benzoate (3.0 g, 8.7 mmol) in anhydrous THF (15 mL) was added a solution of sodium bis(trimethylsilyl)amide in anhydrous THF (6.5 mL, 13 mmol, 2 mol/L) at −78° C. The reaction mixture was stirred at this temperature for 1 h. Then a solution of N-fluorobenzenesulfonimide (1.0 g, 4.6 mmol) in anhydrous THF (10 mL) was added. The reaction mixture was stirred for another 1 h at this temperature and then heated to −30° C. and stirred overnight. The reaction mixture was quenched with hydrochloric acid (0.01 M, 15 mL), extracted with dichloromethane (80 mL×2), washed with saturated brine (20 mL), dried over anhydrous sodium sulfate, filtered and concentrated. The residue was purified by column chromatography on a silica gel eluted with PE/EA (v/v=2/1) to give the title compound as yellow oil (1.86 g, 59%).

MS (ESI, pos. ion) m/z: 365.1 [M+H]$^+$.

Step 7: methyl 4-(2-(3-bromo-6-methoxypyridin-2-yl)-1-fluorovinyl)-3-(methoxymethoxy)benzoate To a mixture of methyl 4-((diethoxyphosphoryl)fluoromethyl)-3-(methoxymethoxy)benzoate (1.86 g, 5.0 mmol) in DMF (30 mL) was added sodium hydride (0.26 g, 6.6 mmol, 60%) under an ice bath. The reaction mixture was stirred for 0.5 h and then 3-bromo-6-methoxypicolinaldehyde (0.95 g, 4.4 mmol) was added (See the synthetic method described in *Organic and Biomolecular Chemistry*, 2003, (1)16, 2865-2876). The reaction mixture was then warmed to rt and stirred for 0.5 h, quenched with saturated aqueous ammonium chloride (10 mL), extracted with EA (20 mL×2). The combined organic layers were washed with saturated brine (20 mL), dried over anhydrous sodium sulfate, filtered and concentrated in vacuo. The residue was purified by column chromatography eluted with PE/EA (v/v=10/1) to give the title compound as yellow oil (900 mg, 48%).

MS (ESI, pos. ion) m/z: 426.0 [M+H]$^+$;

Step 8: methyl 4-(2-(3-bromo-6-methoxypyridin-2-yl)-1-fluorovinyl)-3-hydroxybenzoate To a mixture of methyl 4-(2-(3-bromo-6-methoxypyridin-2-yl)-1-fluorovinyl)-3-(methoxymethoxy)benzoate (770 mg, 1.8 mmol) in THF (20 mL) was added hydrochloric acid (3 mL, 18 mmol, 6 M). The reaction mixture was stirred at 50° C. for 5 h, then cooled to rt and diluted with water (20 mL). The resulting mixture was adjusted to alkalinity with solid potassium carbonate. The mixture was extracted with EA (30 mL×2), washed with saturated brine (10 mL), dried over anhydrous sodium sulfate, filtered and concentrated in vacuo. The residue was purified by column chromatography eluted with PE/EA (v/v, 5/1) to give the title compound as light yellow oil (605 mg, 88%).

MS (ESI, pos. ion) m/z: 382.2 [M+H]$^+$.

Step 9: methyl 10-fluoro-2-methoxybenzo[6,7]oxepino[3,2-b]pyridine-7-carboxylate A mixture of cuprous iodide (120 mg, 0.63 mmol), N,N-dimethylglycine (330 mg, 3.2 mmol), cesium carbonate (1.02 g, 3.2 mmol) and methyl 4-(2-(3-bromo-6-methoxypyridin-2-yl)-1-fluorovinyl)-3-hydroxybenzoate (605 mg, 1.6 mmol) in 1,4-dioxane (8 mL) was heated to reflux overnight under nitrogen atmosphere. The reaction mixture was cooled to rt, filtered, concentrated in vacuo to obtain the residue which was purified by column chromatography eluted with PE/EA (v/v=8/1) to give the title compound as a yellow solid (200 mg, 42%).

MS (ESI, pos. ion) m/z: 302.2 [M+H]$^+$.

Step 10: methyl 10-fluoro-2-oxo-1,2-dihydrobenzo[6,7]oxepino[3,2-b]pyridine-7-carboxylate To a mixture of methyl 10-fluoro-2-methoxybenzo[6,7]oxepino[3,2-b]pyridine-7-carboxylate (250 mg, 0.84 mmol) and sodium iodide (390 mg, 3.2 mmol) in acetonitrile (5 mL) was added trimethylchlorosilane (0.25 mL, 3.0 mmol) at rt. The reaction mixture was stirred at 85° C. for 3 h, followed by addition of saturated aqueous sodium thiosulfate (50 mL) to quench the reaction. The mixture was extracted with EA (50 mL×2), and the combined organic layers were washed with saturated brine (30 mL), dried over anhydrous sodium sulfate, filtered and concentrated in vacuo. The residue was purified by column chromatography on a silica gel eluted with dichloromethane/methanol (v/v=30/1) to give the title compound as yellow oil (120 mg, 50%).

MS (ESI, pos. ion) m/z: 288.2 [M+H]$^+$.

Step 11: methyl 2-((5-cyclopropyl-3-(2,6-dichlorophenyl)isoxazol-4-yl)methoxy)-10-fluorobenzo[6,7]oxepino[3,2-b]pyridine-7-carboxylate A mixture of methyl 10-fluoro-2-oxo-1,2-dihydrobenzo[6,7]oxepino[3,2-b]pyridine-7-carboxylate (120 mg, 0.4 mmol), 4-(chloromethyl)-5-cyclopropyl-3-(2,6-dichlorophenyl) isoxazole (170 mg, 0.54 mmol) and potassium phosphate (180 mg, 0.8 mmol) in DMF (8 mL) was stirred at 60° C. overnight, cooled to rt, diluted with water (30 mL). The mixture was extracted with EA (40 mL×2), and the combined organic layers were washed with saturated brine (20 mL), dried over anhydrous sodium sulfate, filtered and concentrated in vacuo. The residue was purified by column chromatography eluted with PE/EA (v/v=8/1) to give the title compound as yellow oil (180 mg, 78%).

MS (ESI, pos. ion) m/z: 553.1 [M+H]⁺.

Step 12: 2-((5-cyclopropyl-3-(2,6-dichlorophenyl)isoxazol-4-yl)methoxy)-10-fluorobenzo[6,7]oxepino[3,2-b]pyridine-7-carboxylic acid To a mixture of methyl 2-((5-cyclopropyl-3-(2,6-dichlorophenyl)isoxazol-4-yl) methoxy)-10-fluorobenzo[6,7]oxepino[3,2-b]pyridine-7-carboxylate (180 mg, 0.33 mmol) in a mixed solvent of THF (8 mL) and water (8 mL) was added sodium hydroxide (100 mg, 2.5 mmol). The reaction mixture was stirred at rt overnight, concentrated to remove most of the solvent. The residue was diluted with water (10 mL), adjusted to acidity with hydrochloric acid (2 M, 8 mL), and the mixture was extracted with EA (30 mL×2). The combined organic layer were washed with saturated brine (10 mL), dried over anhydrous sodium sulfate, filtered and concentrated. The residue was purified by column chromatography eluted with dichloromethane/methanol (v/v=10/1) to give the title compound as a yellow solid (130 mg, 74%).

MS (ESI, pos. ion) m/z: 539.0 [M+H]⁺;
¹H NMR (400 MHz, DMSO-d₆) δ 13.4 (s, 1H), 7.89-7.37 (m, 2H), 7.75-7.68 (m, 2H), 7.52 (d, J=8.2 Hz, 2H), 7.45-7.37 (m, 1H), 6.65 (d, J=8.8 Hz, 1H), 6.59 (d, J=18.0 Hz, 1H), 5.18 (s, 2H), 2.54-2.46 (m, 1H), 1.21-1.16 (m, 2H), 1.13-1.10 (m, 2H).

Example 2: 2-((5-cyclopropyl-3-(2,6-dichlorophenyl)isoxazol-4-yl)methoxy)-11H-benzo[2,3][1,4]dioxepino[6,5-b]pyridine-7-carboxylic acid

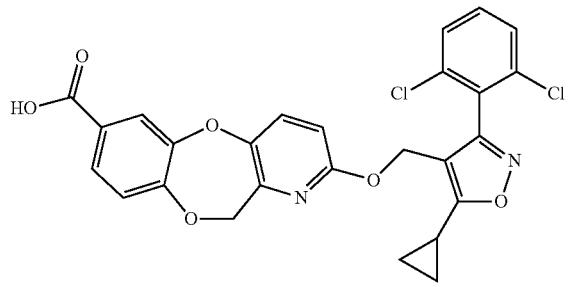 [SMILES: O=C(O)c1ccc2c(c1)Oc1ccc(OCc3c(-c4c(Cl)cccc4Cl)noc3C3CC3)nc1CO2]

Step 1:
3-bromo-2-(bromomethyl)-6-methoxypyridine

To a mixture of (3-bromo-6-methoxypyridin-2-yl)methanol (1.9 g, 8.7 mmol) in dichloromethane (100 mL) was added N-bromosuccinimide (1.8 g, 10 mmol) and triphenylphosphine (2.6 g, 10 mmol) under an ice bath condition and nitrogen atmosphere. The reaction mixture was stirred at rt for 3 h and then concentrated in vacuo, the residue was purified by column chromatography on a silica gel eluted with PE/EA (v/v=30/1) to give the title compound as light yellow liquid (1.4 g, 57%).

Step 2: methyl 4-((3-bromo-6-methoxypyridin-2-yl)methoxy)-3-iodobenzoate

A mixture of 3-bromo-2-(bromomethyl)-6-methoxypyridine (1.4 g, 5.0 mmol), methyl 3-iodo-4-hydroxybenzoate (1.52 g, 5.5 mmol), potassium phosphate (1.6 mg, 7.5 mmol) in DMF (10 mL) was stirred at 60° C. for 3 h. Then the reaction mixture was cooled to rt, diluted with water (40 mL), extracted with EA (80 mL×2). The combined organic layers were washed with saturated brine (20 mL), dried over anhydrous sodium sulfate, filtered and concentrated. The residue was purified by column chromatography eluted with PE/EA (v/v=20/1) to give the title compound as a white solid (2.2 g, 92%).

MS (ESI, pos. ion) m/z: 477.9 [M+H]⁺.

Step 3: 4-((3-bromo-6-methoxypyridin-2-yl)methoxy)-3-hydroxybenzoic acid

A mixture of methyl 4-((3-bromo-6-methoxypyridin-2-yl)methoxy)-3-iodobenzoate (478 mg, 1.0 mmol), cuprous iodide (19 mg, 0.1 mmol), 1,10-phenanthroline (36 mg, 0.2 mmol) and potassium hydroxide (337 mg, 6.0 mmol) in a mixed solvent of DMSO (0.4 mL) and water (0.4 mL) was heated to 100° C. and stirred for 24 h under nitrogen atmosphere. The reaction mixture was cooled to rt and diluted with water (5 mL), adjusted to acidity with hydrochloric acid (1 M, 10 mL). The resulting mixture was extracted with EA (30 mL×2). The combined organic layers were washed with saturated brine (10 mL), dried over anhydrous sodium sulfate, filtered and concentrated in vacuo. The residue was purified by column chromatography eluted with PE/EA (v/v=1/1) to give the title compound as a yellow solid (230 mg, 65%).

MS (ESI, pos. ion) m/z: 354.0 [M+H]⁺.

Step 4: methyl 4-((3-bromo-6-methoxypyridin-2-yl)methoxy)-3-hydroxybenzoate

A mixture of 4-((3-bromo-6-methoxypyridin-2-yl)methoxy)-3-hydroxybenzoic acid (230 mg, 0.65 mmol) in methanol (100 mL) was treated with 2 drops of concentrated sulfuric acid. The mixture was heated to reflux and stirred overnight. The reaction mixture was cooled to rt and concentrated in vacuo. The residue was purified by column chromatography on a silica gel eluted with PE/EA (v/v=10/1) to give the title compound as a light yellow semisolid (150 mg, 63%).

Step 5: methyl 2-methoxy-11H-benzo[2,3][1,4]dioxepino[6,5-b]pyridine-7-carboxylate A mixture of methyl 4-((3-bromo-6-methoxypyridin-2-yl)methoxy)-3-hydroxybenzoate (150 mg, 0.4 mmol), cuprous iodide (30 mg, 0.16 mmol), N,N-dimethylglycine (17 mg, 0.16 mmol) and cesium carbonate (270 mg, 0.8 mmol) in anhydrous 1,4-dioxane (5 mL) was heated to reflux and stirred overnight under nitrogen atmosphere. The reaction mixture was cooled to rt, filtered and concentrated in vacuo. The residue was purified by column chromatography eluted with PE/EA (v/v=5/1) to give the title compound as a white solid (57 mg, 49%).

Step 6: methyl 2-oxo-2,11-dihydro-1H-benzo[2,3][1,4]dioxepino[6,5-b]pyridine-7-carboxylate To a mixture of methyl 2-methoxy-11H-benzo[2,3][1,4]dioxepino[6,5-b]pyridine-7-carboxylate (57 mg, 0.2 mmol)

and sodium iodide (100 mg, 0.66 mmol) in acetonitrile (5 mL) was added trimethylchlorosilane (0.1 mL, 1.0 mmol) at rt. Then the mixture was heated to 85° C. and stirred for 3 h, cooled to rt, quenched with saturated aqueous sodium thiosulfate (50 mL). The resulting mixture was extracted with EA (50 mL×2). The combined organic layers were washed with saturated brine (30 mL), dried over anhydrous sodium sulfate, filtered and concentrated. The residue was purified by column chromatography eluted with dichloromethane/methanol (v/v=30/1) to give the title compound as a light yellow solid (54 mg, 100%).

MS (ESI, neg. ion) m/z: 272.0 [M−H]⁻.

Step 7: methyl 2-((5-cyclopropyl-3-(2,6-dichlorophenyl)isoxazol-4-yl)methoxy)-11H-benzo[2,3][1,4]dioxepino[6,5-b]pyridine-7-carboxylate A mixture of methyl 2-oxo-2,11-dihydro-1H-benzo[2,3][1,4]dioxepino[6,5-b]pyridine-7-carboxylate (55 mg, 0.2 mmol), 4-(chloromethyl)-5-cyclopropyl-3-(2,6-dichlorophenyl)isoxazole (100 mg, 0.3 mmol) (See the synthetic method of compound A6e in WO2011020615) and potassium phosphate (100 mg, 0.5 mmol) in DMF (5 mL) was heated to 60° C. and stirred for 3 h. The mixture was cooled to rt, diluted with water (40 mL), extracted with EA (80 mL×2). The combined organic layers were washed with saturated brine (20 mL), dried over anhydrous sodium sulfate, filtered and concentrated in vacuo. The residue was purified by column chromatography on a silica gel eluted with PE/EA (v/v=20/1) to give the title compound as light yellow oil (90 mg, 80%).

MS (ESI, pos. ion) m/z: 539.0 [M+H]⁺.

Step 8: 2-((5-cyclopropyl-3-(2,6-dichlorophenyl)isoxazol-4-yl)methoxy)-11H-benzo[2,3][1,4]dioxepino[6,5-b]pyridine-7-carboxylic acid To a mixture of methyl 2-((5-cyclopropyl-3-(2,6-dichlorophenyl)isoxazol-4-yl)methoxy)-11H-benzo[2,3][1,4]dioxepino[6,5-b]pyridine-7-carboxylate (90 mg, 0.17 mmol) in a mixed solvent of THF (2 mL) and water (1.75 mL) was added sodium hydroxide (70 mg, 1.75 mmol). The reaction mixture was heated to 60° C. and stirred overnight. Then the mixture was concentrated to remove most of the solvent, diluted with water (20 mL). The mixture was adjusted to acidity with hydrochloric acid (1 M, 5 mL), and the resulting mixture was extracted with EA (30 mL×2). The combined organic layers were washed with saturated brine (10 mL), dried over anhydrous sodium sulfate, filtered and concentrated in vacuo to give the title compound as a light yellow solid (60 mg, 70%).

MS (ESI, neg. ion) m/z: 523.0 [M−H]⁻;

¹H NMR (400 MHz, CDCl₃) δ 7.92 (d, J=1.7 Hz, 1H), 7.75 (dd, J=8.5, 1.8 Hz, 1H), 7.50-7.35 (m, 3H), 7.34-7.29 (m, 1H), 7.03 (d, J=8.5 Hz, 1H), 6.60 (d, J=8.8 Hz, 1H), 5.24 (s, 2H), 5.19 (s, 2H), 2.40-2.28 (m, 1H), 1.32-1.29 (m, 2H), 1.21-1.15 (n, 2H).

Example 3: 3-((5-cyclopropyl-3-(2,6-dichlorophenyl)isoxazol-4-yl)methoxy)-1a,10b-dihydro-1H-benzo[6,7]cyclopropa[4,5]oxepino[3,2-b]pyridine-8-carboxylic acid

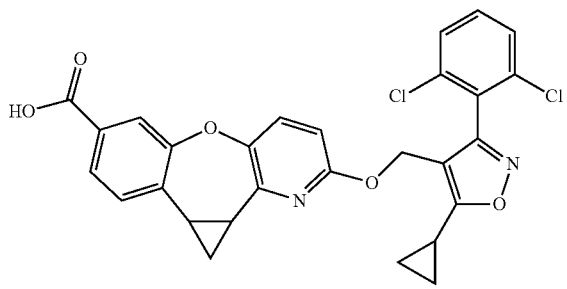 [SMILES: O=C(O)c1ccc2c(c1)Oc1ccc(OCc3c(-c4c(Cl)cccc4Cl)noc3C3CC3)nc1C1CC21]

To a mixture of methyl 3-((5-cyclopropyl-3-(2,6-dichlorophenyl)isoxazol-4-yl)methoxy)-1a,10b-dihydro-1H-benzo[6,7]cyclopropa[4,5]oxepino[3,2-b]pyridine-8-carboxylate (12 mg, 0.02 mmol) and potassium fluoride (50 mg, 0.86 mmol) in N-methyl-2-pyrrolidone (2 mL) was added thiophenol (100 mg, 0.91 mmol). Then the reaction mixture was heated to 200° C. and stirred for 10 mins. The mixture was cooled to rt and diluted with water (20 mL), extracted with EA (50 mL×2). The combined organic layers were dried over with anhydrous sodium sulfate, filtered and concentrated. The residue was purified by column chromatography eluted with dichloromethane/methanol (v/v=10/1) to give the title compound as a white solid (5.6 mg, 48%).

MS (ESI, pos. ion) m/z: 535.4 [M+H]⁺;

¹H NMR (400 MHz, CDCl₃) δ 7.81 (d, J=7.9 Hz, 1H), 7.77 (s, 1H), 7.43 (d, J=7.9 Hz, 1H), 7.39-7.29 (m, 3H), 7.18 (t, J=8.1 Hz, 1H), 6.39 (d, J=8.6 Hz, 1H), 5.20 (d, J=1.7 Hz, 2H), 3.41 (t, J=7.0 Hz, 1H), 3.02 (t, J=7.0 Hz, 1H), 2.36-2.29 (m, 1H), 1.69-1.61 (m, 1H), 1.55-1.48 (m, 1H), 1.28-1.25 (m, 2H), 1.17-1.13 (m, 2H).

Example 4: 2-((5-cyclopropyl-3-(2,6-dichlorophenyl)isoxazol-4-yl)methoxy)-9-fluoro-10,11-dihydrobenzo[6,7]oxepino[3,2-b]pyridine-7-carboxylic acid

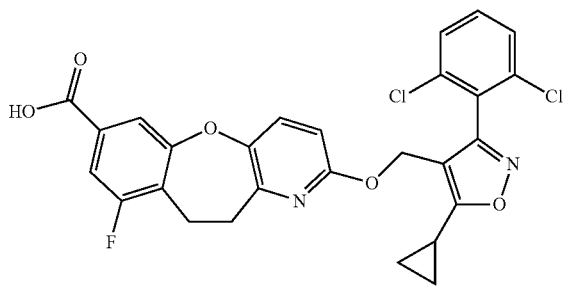 [SMILES: O=C(O)c1cc(F)c2c(c1)Oc1ccc(OCc3c(-c4c(Cl)cccc4Cl)noc3C3CC3)nc1CC2]

Step 1: 4-bromo-2-fluoro-6-hydroxybenzaldehyde

To a mixture of 4-bromo-2,6-difluorobenzaldehyde (2.0 g, 9.0 mmol) in DMF (10 mL) was added dropwise slowly a solution of potassium hydroxide (1.0 g, 18.0 mmol,) in water (15 mL). The reaction mixture was heated to 60° C., stirred for 2 h and then cooled to rt, diluted with water (20 mL). The mixture was adjusted to acidity with hydrochloric acid (2 M, 15 mL) and the resulting mixture was extracted with EA (50 mL×2). The combined organic layers were washed with saturated brine (10 mL), dried over with anhydrous sodium sulfate, filtered and concentrated in vacuo. The residue was purified by column chromatography eluted with PE/EA (v/v=20/1) to give the title compound as yellow oil (1.5 g, 76%).

MS (ESI, neg. ion) m/z: 217.0 [M–H]⁻.

Step 2: 4-bromo-2-fluoro-6-(methoxymethoxy)benzaldehyde

To a mixture of 4-bromo-2-fluoro-6-hydroxybenzaldehyde (7.5 g, 34 mmol) and diisopropylethylamine (11.0 mL, 66 mmol) in dichloromethane (100 mL) was added dropwise chloromethyl methyl ether (4.1 mL, 51 mmol) under an ice bath condition. Then the reaction mixture was stirred at rt overnight. The mixture was quenched with water (200 mL), extracted with dichloromethane (50 mL×2). The combined organic layers were washed with saturated brine (10 mL), dried over anhydrous sodium sulfate, filtered and concentrated in vacuo. The residue was purified by column chromatography on a silica gel eluted with PE/EA (v/v=20/1) to give the title compound as a yellow solid (4.3 g, 48%).

$^1$H NMR (400 MHz, CDCl$_3$) δ 10.39 (s, 1H), 7.24 (s, 1H), 7.01 (dd, J=9.9, 1.0 Hz, 1H), 5.31 (s, 2H), 3.54 (s, 3H).

Step 3: 3-bromo-2-(4-bromo-2-fluoro-6-(methoxymethoxy)styryl)-6-methoxypyridine To a mixture of diethyl ((3-bromo-6-methoxypyridin-2-yl)methyl)phosphonate (2.5 g, 7.4 mmol) in THF (40 mL) was added sodium hydride (0.29 g, 7.3 mmol, 60%) under an ice bath condition. The mixture was stirred for 0.5 h at this temperature, followed by addition of a solution of 4-bromo-2-fluoro-6-(methoxymethoxy) benzaldehyde (1.5 g, 5.7 mmol) in THF (20 mL). Then the reaction mixture was warmed to rt and stirred for further 5 h. The reaction was quenched with saturated aqueous ammonium chloride (50 mL). The resulting mixture was extracted with EA (60 mL×2). The combined organic layers were washed with saturated brine (20 mL), dried over anhydrous sodium sulfate, filtered and concentrated in vacuo. The residue was purified by column chromatography eluted with PE/EA (v/v=10/1) to give the title compound as a white solid (1.5 g, 60%).

Step 4: 3-bromo-2-(4-bromo-2-fluoro-6-(methoxymethoxy)phenethyl)-6-methoxypyridine A mixture of 3-bromo-2-(4-bromo-2-fluoro-6-(methoxymethoxy)styryl)-6-methoxypyridine (1.25 g, 2.8 mmol), sodium acetate (1.38 g, 16.8 mmol) and p-toluenesulfonyl hydrazide (3.12 g, 16.8 mmol) in a mixed solvent of THF (40 mL) and water (20 mL) was heated to reflux for 7 h. Then the reaction mixture was cooled to rt, diluted with water (200 mL), extracted with EA (100 mL×2). The combined organic layers were washed with saturated brine (20 mL), dried over anhydrous sodium sulfate, filtered and concentrated in vacuo. The residue was purified by column chromatography on a silica gel eluted with PE/EA (v/v=20/1) to give the title compound as a solid (1.2 g, 96%).

MS (ESI, pos. ion) m/z: 447.9 [M+H]⁺.

Step 5: 5-bromo-2-(2-(3-bromo-6-methoxypyridin-2-yl)ethyl)-3-fluorophenol

To a mixture of 3-bromo-2-(4-bromo-2-fluoro-6-(methoxymethoxy)phenethyl)-6-methoxypyridine (1.5 g, 3.3 mmol) in THF (30 mL) was added hydrochloric acid (6 mL, 36 mmol). Then the mixture was stirred at 50° C. overnight, then cooled to rt, diluted with water (20 mL) and adjusted to alkalinity with potassium carbonate. The resulting mixture was extracted with EA (30 mL×2). The combined organic layers were washed with saturated brine (10 mL), dried over anhydrous sodium sulfate, filtered and concentrated in vacuo. The residue was purified by column chromatography eluted with PE/EA (v/v=20/1) to give the title compound as a white solid (1.2 g, 89%).

Step 6: 7-bromo-9-fluoro-2-methoxy-10,11-dihydrobenzo[6,7]oxepino[3,2-b]pyridine A mixture of cuprous iodide (94 mg, 0.50 mmol), N,N-dimethylglycine (120 mg, 1.16 mmol), cesium carbonate (1.3 g, 4.0 mmol) and 5-bromo-2-(2-(3-bromo-6-methoxypyridin-2-yl)ethyl)-3-fluorophenol (800 mg, 2.0 mmol) in 1,4-dioxane (40 mL) was heated to reflux overnight under nitrogen atmosphere. The mixture was cooled to rt, filtered and concentrated in vacuo. The residue was purified by column chromatography eluted with PE/EA (v/v, 15/1) to give the title compound as a white solid (400 mg, 60%).

$^1$H NMR (400 MHz, CDCl$_3$) δ 7.37 (d, J=8.7 Hz, 1H), 7.16 (s, 1H), 7.02 (dd, J=8.7, 1.7 Hz, 1H), 6.56 (d, J=8.7 Hz, 1H), 3.90 (s, 3H), 3.25-3.18 (m, 2H), 3.12-3.06 (m, 2H).

Step 7: methyl 9-fluoro-2-methoxy-10,11-dihydrobenzo[6,7]oxepino[3,2-b]pyridine-7-carboxylate A mixture of 7-bromo-9-fluoro-2-methoxy-10,11-dihydrobenzo[6,7]oxepino[3,2-b]pyridine (0.5 g, 1.5 mmol), triethylamine (0.4 mL, 3.0 mmol) and 1,1'-bis(diphenylphosphino)ferrocene]palladium(II) chloride (10 mg, 0.015 mmol) in methanol (30 mL) was stirred at 100° C. in an autoclave under carbon monoxide atmosphere (3.0 Mpa) for 2 days. Then the reaction mixture was cooled to rt and concentrated in vacuo to remove the solvent. The residue was purified by column chromatography eluted with PE/EA (v/v=30/1) to give the title compound as a white solid (300 mg, 60%).

Step 8: methyl 9-fluoro-2-oxo-1,2,10,11-tetrahydrobenzo[6,7]oxepino[3,2-b]pyridine-7-carboxylate To a mixture of methyl 9-fluoro-2-methoxy-10,11-dihydrobenzo[6,7]oxepino[3,2-b]pyridine-7-carboxylate (310 mg, 1.0 mmol) and sodium iodide (460 mg, 3.1 mmol) in acetonitrile (9 mL) was added trimethylchlorosilane (0.27 mL, 3.1 mmol) at rt. Then the reaction mixture was heated to 85° C. and stirred for 1.5 h, then cooled to rt and quenched with saturated aqueous sodium thiosulfate (50 mL). The resulting mixture was extracted with EA (50 mL×2), washed with saturated brine (30 mL), dried over anhydrous sodium sulfate, filtered and concentrated in vacuo. The residue was purified by column chromatography eluted with dichloromethane/methanol (v/v=15/1) to give the title compound as a yellow solid (290 mg, 98%).

MS (ESI, pos. ion) m/z: 290.0 [M+H]⁺.

Step 9: methyl 2-((5-cyclopropyl-3-(2,6-dichlorophenyl)isoxazol-4-yl)methoxy)-9-fluoro-10,11-dihydrobenzo[6,7]oxepino[3,2-b]pyridine-7-carboxylate A mixture of methyl 9-fluoro-2-oxo-1,2,10,11-tetrahydrobenzo[6,7]oxepino[3,2-b]pyridine-7-carboxylate (310 mg, 1.1 mmol), 4-(chloromethyl)-5-cyclopropyl-3-(2,6-dichlorophenyl) isoxazole (420 mg, 1.4 mmol) and potassium phosphate (450 mg, 2.1 mmol) in DMF (20 mL) was stirred at 50° C. for 4 h. Then the reaction mixture was cooled to rt and diluted with water (30 mL). The resulting mixture was extracted with EA (40 mL×2). The combined organic layers were washed with saturated brine (20 mL), dried over anhydrous sodium sulfate, filtered and concentrated. The residue was purified by column chromatography on a silica gel eluted with PE/EA (v/v=4/1) to give the title compound as yellow oil (290 mg, 49%).

Step 10: 2-((5-cyclopropyl-3-(2,6-dichlorophenyl)isoxazol-4-yl)methoxy)-9-fluoro-10,11-dihydrobenzo[6,7]oxepino[3,2-b]pyridine-7-carboxylic acid To a mixture of methyl 2-((5-cyclopropyl-3-(2,6-dichlorophenyl)isoxazol-4-yl)methoxy)-9-fluoro-10,11-dihydrobenzo[6,7]oxepino[3,2-b]pyridine-7-carboxylate (290 mg, 0.52 mmol) in a mixed solvent of THF (9 mL) and water (9 mL) was added sodium hydroxide (72 mg, 1.8 mmol). Then the reaction mixture was stirred at 60° C. overnight. The reaction mixture was cooled to rt, concentrated to remove most of the solvent under reduced pressure. The residue was diluted with water (10 mL), adjusted to acidity with hydrochloric acid (2 M, 2 mL). The resulting mixture was extracted with EA (30 mL×2). The combined organic layers were washed with saturated brine (10 mL), dried over anhydrous sodium sulfate, filtered and concentrated in vacuo. The residue was purified by column chromatography eluted with PE/EA (v/v, 1/1) to give the title compound as a light yellow solid (270 mg, 96%).

MS (ESI, pos. ion) m/z: 541.0 [M+H]$^+$;
$^1$H NMR (400 MHz, CDCl$_3$) δ 7.70 (s, 1H), 7.57 (d, J=9.2 Hz, 1H), 7.41-7.34 (m, 3H), 7.28-7.25 (m, 1H), 6.44 (d, J=8.7 Hz, 1H), 5.16 (s, 2H), 3.24-3.10 (m, 4H), 2.31-2.27 (m, 1H), 1.32-1.29 (m, 2H), 1.20-1.12 (m, 2H).

Example 5:2-((5-cyclopropyl-3-(2,6-dichlorophenyl)isoxazol-4-yl)methoxy)-11-fluorobenzo oxepino[3,2-b]pyridine-7-carboxylic acid

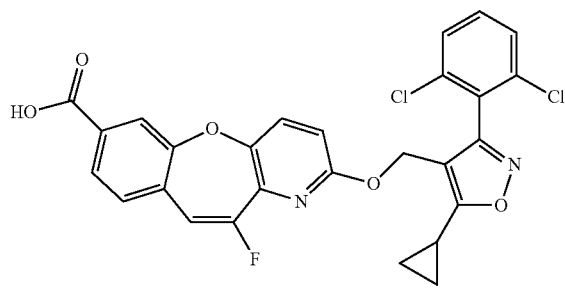 [SMILES: O=C(O)c1ccc2c(c1)Oc1ccc(OCc3c(-c4c(Cl)cccc4Cl)noc3C3CC3)nc1C(F)=C2]

Step 1: 4-bromo-2-(methoxymethoxy)benzaldehyde

Using 4-bromo-2-hydroxybenzaldehyde (15.0 g, 74.6 mmol) as a starting material, the title compound was prepared according to the procedure described in step 5 of example 1 as a white solid (6.0 g, 98%).

Step 2: methyl 4-formyl-3-(methoxymethoxy)benzoate

Using 4-bromo-2-(methoxymethoxy)benzaldehyde (2.9 g, 11.8 mmol) as a starting material, the title compound was prepared according to the procedure described in step 7 of example 4 as a white solid (2.6 g, 98%).

Step 3: 3-bromo-2-(bromomethyl)-6-methoxypyridine

Using 3-bromo-6-methoxy-2-methylpyridine (20.0 g, 99 mmol) as a starting material, the title compound was prepared according to the procedure described in step 2 of example 1 as colourless oil (26.5 g, 95%).

Step 4: diethyl ((3-bromo-6-methoxypyridin-2-yl)methyl)phosphonate

Using 3-bromo-2-(bromomethyl)-6-methoxypyridine (26.5 g, 94 mmol) as a starting material, the title compound was prepared according to the procedure described in step 3 of example 1 as light yellow oil (20.7 g, 65%).

MS (ESI, pos. ion) m/z: 338.0 [M+H]$^+$.

Step 5: diethyl ((3-bromo-6-methoxypyridin-2-yl)fluoromethyl)phosphonate

Using diethyl ((3-bromo-6-methoxypyridin-2-yl)methyl)phosphonate (3.0 g, 8.9 mmol) as a starting material, the title compound was prepared according to the procedure described in step 6 of example 1 as light yellow oil (2.8 g, 87%).

MS (ESI, pos. ion) m/z: 356.3 [M+H]$^+$.

Step 6: methyl 4-(2-(3-bromo-6-methoxypyridin-2-yl)-2-fluorovinyl)-3-(methoxymethoxy)benzoate Using diethyl ((3-bromo-6-methoxypyridin-2-yl)fluoromethyl)phosphonate (2.0 g, 5.8 mmol) and methyl 4-formyl-3-(methoxymethoxy)benzoate (1.0 g, 4.5 mmol) as a starting material, the title compound was prepared according to the procedure described in step 7 of example 1 as yellow oil (1.26 g, 66%).

Step 7: methyl 4-(2-(3-bromo-6-methoxypyridin-2-yl)-2-fluorovinyl)-3-hydroxybenzoate Using methyl 4-(2-(3-bromo-6-methoxypyridin-2-yl)-2-fluorovinyl)-3-(methoxymethoxy) benzoate (1.26 g, 3.0 mmol) as a starting material, the title compound was prepared according to the procedure described in step 8 of example 1 as a yellow solid (1.0 g, 88%).

MS (ESI, pos. ion) m/z: 382.0 [M+H]$^+$.

Step 8: methyl 11-fluoro-2-methoxybenzo[6,7]oxepino[3,2-b]pyridine-7-carboxylate Using methyl 4-(2-(3-bromo-6-methoxypyridin-2-yl)-2-fluorovinyl)-3-hydroxybenzoate (0.89 g, 2.3 mmol) as a starting material, the title compound was prepared according to the procedure described in step 9 of example 1 as a yellow solid (0.31 g, 44%).

MS (ESI, pos. ion) m/z: 302.1 [M+H]$^+$;

Step 9: methyl 11-fluoro-2-oxo-1,2-dihydrobenzo[6,7]oxepino[3,2-b]pyridine-7-carboxylate Using methyl 11-fluoro-2-methoxybenzo[6,7]oxepino[3,2-b]pyridine-7-carboxylate (310 mg, 1.0 mmol) as a starting material, the title compound was prepared according to the procedure described in step 10 of example 1 as a grey solid (200 mg, 68%).

MS (ESI, pos. ion) m/z: 288.1 [M+H]+.

Step 10: methyl 2-((5-cyclopropyl-3-(2,6-dichlorophenyl)isoxazol-4-yl)methoxy)-11-fluorobenzo[6,7]oxepino[3,2-b]pyridine-7-carboxylate Using methyl 11-fluoro-2-oxo-1,2-dihydrobenzo[6,7]oxepino[3,2-b]pyridine-7-carboxylate (200 mg, 0.7 mmol) and 4-(chloromethyl)-5-cyclopropyl-3-(2,6-dichlorophenyl)isoxazole (280 mg, 0.9 mmol) as a starting material, the title compound was prepared according to the procedure described in step 11 of example 1 as a grey solid (260 mg, 67%).

Step 11: 2-((5-cyclopropyl-3-(2,6-dichlorophenyl)isoxazol-4-yl)methoxy)-11-fluorobenzo[6,7]oxepino[3,2-b]pyridine-7-carboxylic acid Using methyl 2-((5-cyclopropyl-3-(2,6-dichlorophenyl)isoxazol-4-yl)methoxy)-11-fluorobenzo[6,7]oxepino[3,2-b]pyridine-7-carboxylate (260 mg, 0.47 mmol) as a starting material, the title compound was prepared according to the procedure described in step 12 of example 1 as a grey solid (190 mg, 74%).

MS (ESI, pos. ion) m/z: 539.0 [M+H]+;

$^1$H NMR (400 MHz, CDCl$_3$) δ 7.92-7.89 (m, 2H), 7.45 (d, J=8.7 Hz, 1H), 7.37-7.35 (m, 2H), 7.33-7.21 (m, 2H), 6.80-6.65 (m, 2H), 5.24 (s, 2H), 2.48-2.42 (m, 1H), 1.36-1.30 (m, 2H), 1.18-1.13 (m, 2H).

Example 6: 2-((5-cyclopropyl-3-(2,6-dichlorophenyl)isoxazol-4-yl)methoxy)-8-fluoro-10,11-dihydrobenzo[6,7]oxepino[3,2-b]pyridine-7-carboxylic acid

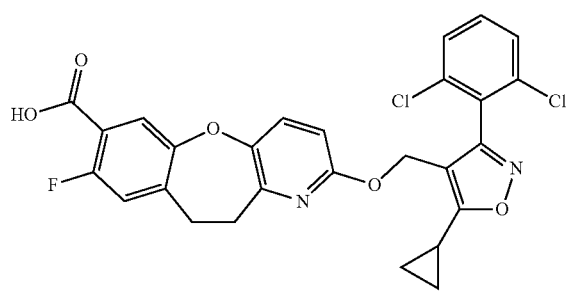 [SMILES: O=C(O)c1cc2c(cc1F)CCc1nc(OCc3c(-c4c(Cl)cccc4Cl)noc3C3CC3)ccc1O2]

Using 4-bromo-5-fluoro-2-hydroxybenzaldehyde as a starting material, the title compound was prepared according to the procedure described in example 4 as a yellow solid (320 mg).

MS (ESI, pos. ion) m/z: 541.0 [M+H]+;

$^1$H NMR (400 MHz, CDCl$_3$) δ 7.77 (d, J=6.3 Hz, 1H), 7.40-7.33 (m, 3H), 7.28-7.25 (m, 1H), 7.04 (d, J=10.5 Hz, 1H), 6.42 (d, J=8.7 Hz, 1H), 5.12 (s, 2H), 3.22-3.06 (m, 4H), 2.37-2.28 (m, 1H), 1.31-1.27 (m, 2H), 1.18-1.11 (m, 2H).

Example 7: 2-((5-cyclopropyl-3-(2,6-dichlorophenyl)isoxazol-4-yl)methoxy)-11-(trifluoromethyl)benzo[6,7]oxepino[3,2-b]pyridine-7-carboxylic acid

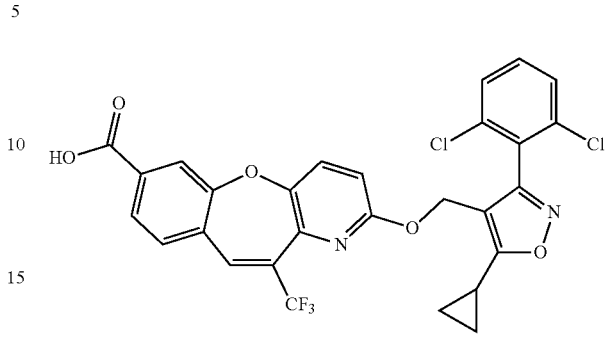

Step 1: 1-(3-bromo-6-methoxypyridin-2-yl)-2,2,2-trifluoroethanol

To a mixture of 3-bromo-6-methoxypicolinaldehyde (5.0 g, 23 mmol) in THF (10 mL) were added trimethyl(trifluoromethyl)silane (5.2 mL, 35 mmol) and a solution of tetrabutylammonium fluoride in THF (1.2 mL, 1.2 mmol, 1 mol/L). Then the reaction mixture was stirred at rt overnight. The mixture was concentrated in vacuo to remove most of the solvent. The residue was diluted with water (50 mL) and the resulting mixture was extracted with EA (50 mL×2). The combined organic layers were washed with saturated brine (30 mL), dried over anhydrous sodium sulfate, filtered and concentrated in vacuo. The residue was purified by column chromatography eluted with PE/EA (v/v=30/1) to give the title compound as a light yellow solid (4.1 g, 62%).

Step 2: 1-(3-bromo-6-methoxypyridin-2-yl)-2,2,2-trifluoroethanone

To a mixture of 1-(3-bromo-6-methoxypyridin-2-yl)-2,2,2-trifluoroethanol (500 mg, 1.75 mmol) in anhydrous dichloromethane (4.5 mL) were added 2,6-lutidine (0.46 mL, 3.9 mmol) and 4-acetamido-2,2,6,6-tetramethyl-1-oxopiperidinium tetrafluoroborate (1.31 g, 4.37 mmol) at rt. The reaction mixture was stirred overnight, then concentrated under reduced pressure. The residue was diluted with ethyl ether (50 mL) followed by stirring for further 0.5 h, filtered to remove the insoluble substance. The filtrate was concentrated in vacuo. The residue was purified by column chromatography eluted with PE to give the title compound as yellow oil (360 mg, 73%).

Step 3: methyl 4-(2-(3-bromo-6-methoxypyridin-2-yl)-3,3,3-trifluoroprop-1-en-1-yl)-3-(methoxymethoxy)benzoate Using 1-(3-bromo-6-methoxypyridin-2-yl)-2,2,2-trifluoroethanone (2.0 g, 7.0 mmol) and methyl 4-((diethoxyphosphoryl)methyl)-3-(methoxymethoxy)benzoate (2.8 g, 8.1 mmol) as a starting material, the title compound was prepared according to the procedure described in step 7 of example 1 as yellow oil (1.1 g, 33%).

MS (ESI, pos. ion) m/z: 476.4 [M+H]+.

Step 4: methyl 4-(2-(3-bromo-6-methoxypyridin-2-yl)-3,3,3-trifluoroprop-1-en-1-yl)-3-hydroxybenzoate Using methyl 4-(2-(3-bromo-6-methoxypyridin-2-yl)-3,3,3-trifluoroprop-1-en-1-yl)-3-(methoxymethoxy)benz oate (1.1 g, 2.3 mmol) as a starting material, the title compound was prepared according to the procedure described in step 8 of example 1 as yellow oil (0.96 g, 96%).

MS (ESI, pos. ion) m/z: 431.9 [M+H]+.

Step 5: methyl 2-methoxy-11-(trifluoromethyl) benzo[6,7]oxepino[3,2-b]pyridine-7-carboxylate Using methyl 4-(2-(3-bromo-6-methoxypyridin-2-yl)-3,3,3-trifluoroprop-1-en-1-yl)-3-hydroxybenzoate (960 mg, 2.2 mmol) as a starting material, the title compound was prepared according to the procedure described in step 9 of example 1 as a yellow solid (530 mg, 68%).

MS (ESI, pos. ion) m/z: 352.3 [M+H]+.

Step 6: methyl 2-oxo-11-(trifluoromethyl)-1,2-dihydrobenzo[6,7]oxepino[3,2-b]pyridine-7-carboxylate Using methyl 2-methoxy-11-(trifluoromethyl)benzo[6,7]oxepino[3,2-b]pyridine-7-carboxylate (250 mg, 0.72 mmol) as a starting material, the title compound was prepared according to the procedure described in step 10 of example 1 as a yellow solid (220 mg, 92%).

MS (ESI, pos. ion) m/z: 338.0 [M+H]+.

Step 7: methyl 2-((5-cyclopropyl-3-(2,6-dichlorophenyl)isoxazol-4-yl)methoxy)-11-(trifluoromethyl) benzo[6,7]oxepino[3,2-b]pyridine-7-carboxylate Using methyl 2-oxo-11-(trifluoromethyl)-1,2-dihydrobenzo[6,7]oxepino[3,2-b]pyridine-7-carboxylate (220 mg, 0.65 mmol) and 4-(chloromethyl)-5-cyclopropyl-3-(2,6-dichlorophenyl) isoxazole (280 mg, 0.9 mmol) as a starting material, the title compound was prepared according to the procedure described in step 11 of example 1 as a yellow solid (368 mg, 93%).

MS (ESI, pos. ion) m/z: 603.0 [M+H]+.

Step 8: 2-((5-cyclopropyl-3-(2,6-dichlorophenyl) isoxazol-4-yl)methoxy)-11-(trifluoromethyl) benzo [6,7]oxepino[3,2-b]pyridine-7-carboxylic acid Using methyl 2-((5-cyclopropyl-3-(2,6-dichlorophenyl) isoxazol-4-yl)methoxy)-11-(trifluoromethyl)benzo[6,7]oxepino[3,2-b]pyridine-7-carboxylate (368 mg, 0.61 mmol) as a starting material, the title compound was prepared according to the procedure described in step 12 of example 1 as a yellow solid (240 mg, 95%).

MS (ESI, pos. ion) m/z: 589.4 [M+H]+;
1H NMR (400 MHz, DMSO-d6) δ 13.42 (s, 1H), 7.89-7.86 (m, 3H), 7.83-7.77 (m, 2H), 7.31 (d, J=8.1 Hz, 2H), 7.10 (t, J=8.1 Hz, 1H), 6.76 (d, J=8.8 Hz, 1H), 5.25 (s, 2H), 2.46-2.37 (m, 1H), 1.17-1.11 (m, 4H).

Example 8: 2-((5-cyclopropyl-3-(2,6-dichlorophenyl)isoxazol-4-yl)methoxy)-11-(trifluoromethyl)-10,11-dihydrobenzo[6,7]oxepino[3,2-b]pyridine-7-carboxylic acid

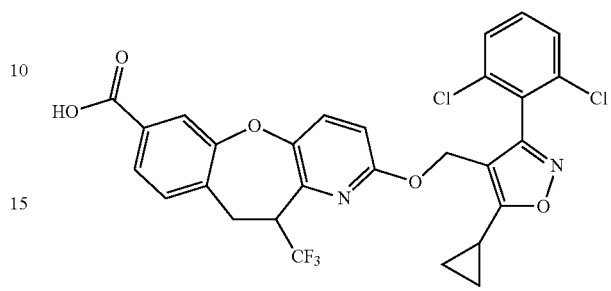

Step 1: methyl 2-methoxy-11-(trifluoromethyl)-10,11-dihydrobenzo[6,7]oxepino[3,2-b]pyridine-7-carboxylate To a mixture of methyl 2-methoxy-11-(trifluoromethyl) benzo[6,7]oxepino[3,2-b]pyridine-7-carboxylate (120 mg, 0.34 mmol) in EA (12 mL) was added 10% Pd/C (56 mg) under hydrogen atmosphere and stirred at rt overnight. The mixture was filtered and concentrated in vacuo. The residue was purified by column chromatography eluted with PE/EA (v/v=10/1) to give the title compound as colourless oil (116 mg, 96%).

MS (ESI, pos. ion) m/z: 354.0 [M+H]+.

Step 2: methyl 2-oxo-11-(trifluoromethyl)-1,2,10,11-tetrahydrobenzo[6,7]oxepino[3,2-b]pyridine-7-carboxylate Using methyl 2-methoxy-11-(trifluoromethyl)-10,11-dihydrobenzo[6,7]oxepino[3,2-b]pyridine-7-carboxylate (116 mg, 0.33 mmol) as a starting material, the title compound was prepared according to the procedure described in step 10 of example 1 as a yellow solid (110 mg, 99%).

MS (ESI, pos. ion) m/z: 340.0 [M+H]+.

Step 3: methyl 2-((5-cyclopropyl-3-(2,6-dichlorophenyl)isoxazol-4-yl)methoxy)-11-(trifluoromethyl)-10,11-dihydrobenzo[6,7]oxepino[3,2-b]pyridine-7-carboxylate Using methyl 2-oxo-11-(trifluoromethyl)-1,2,10,11-tetrahydrobenzo[6,7]oxepino[3,2-b]pyridine-7-carboxylate (90 mg, 0.26 mmol) and 4-(chloromethyl)-5-cyclopropyl-3-(2,6-dichlorophenyl)isoxazole (110 mg, 0.36 mmol) as a starting material, the title compound was prepared according to the procedure described in step 11 of example 1 as colourless oil (110 mg, 69%).

MS (ESI, pos. ion) m/z: 605.0 [M+H]+.

Step 4: 2-((5-cyclopropyl-3-(2,6-dichlorophenyl) isoxazol-4-yl)methoxy)-11-(trifluoromethyl)-10,11-dihydrobenzo[6,7]oxepino[3,2-b]pyridine-7-carboxylic acid Using methyl 2-((5-cyclopropyl-3-(2,6-dichlorophenyl) isoxazol-4-yl)methoxy)-11-(trifluoromethyl)-10,11-dihydrobenzo[6,7]oxepino[3,2-b]pyridine-7-carboxylate (110 mg, 0.18 mmol) as a starting material, the title compound was prepared according to the procedure described in step 12 of example 1 as a white solid (78 mg, 73%).

MS (ESI, pos. ion) m/z: 591.0 [M+H]+;

$^1$H NMR (600 MHz, DMSO-$d_6$) δ 13.15 (s, 1H), 7.74-7.69 (m, 3H), 7.55 (d, J=8.1 Hz, 1H), 7.50 (d, J=7.8 Hz, 1H), 7.46 (d, J=8.0 Hz, 1H), 7.38 (t, J=8.1 Hz, 1H), 6.63 (d, J=8.8 Hz, 1H), 5.28 (d, J=13.0 Hz, 1H), 5.06 (d, J=13.0 Hz, 1H), 4.15-4.09 (m, 1H), 3.51-3.48 (m, 1H), 3.30-3.27 (m, 1H), 2.45-2.41 (m, 1H), 1.18-1.12 (m, 4H).

Example 9: 2-((5-cyclopropyl-3-(2,6-dichlorophenyl)isoxazol-4-yl)methoxy)-10H-spiro[benzo[6,7]oxepino[3,2-b]pyridine-11,1'-cyclopropane]-7-carboxylic acid

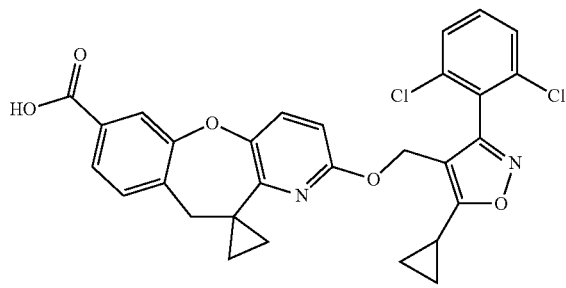 [SMILES: O=C(O)c1ccc2c(c1)Oc1ccc(OCc3c(-c4c(Cl)cccc4Cl)noc3C3CC3)nc1C1(CC1)C2]

Step 1: methyl 4-bromo-2-(methoxymethoxy)benzoate

To a mixture of methyl 4-bromo-2-hydroxybenzoate (10 g, 43 mmol) and diisopropylethylamine (11.0 mL, 65 mmol) in dichloromethane (100 mL) was added dropwise chloromethyl methyl ether (4.9 mL, 65 mmol) under an ice bath condition. Then the reaction mixture was warmed to rt and stirred overnight. The reaction was quenched with water (200 mL), and the resulting mixture was extracted with dichloromethane (150 mL×2). The combined organic layers were washed with saturated brine (10 mL), dried over anhydrous sodium sulfate, filtered and concentrated in vacuo. The residue was purified by column chromatography eluted with PE/EA (v/v=20/1) to give the title compound as colourless oil (10 g, 84%).

Step 2: 1-(4-bromo-2-(methoxymethoxy)phenyl)-2-(3-bromo-6-methoxypyridin-2-yl)ethanone To a mixture of methyl 4-bromo-2-(methoxymethoxy)benzoate (11 g, 40.0 mmol) and 3-bromo-6-methoxy-2-methyl-pyridine (8.08 g, 40.0 mmol) in THF (100 mL) was added dropwise a solution of sodium bis(trimethylsilyl)amide in THF (40 mL, 80 mmol, 2.0 M) under an ice bath condition and nitrogen atmosphere. The reaction mixture was warmed to rt and stirred for 3 h. The reaction was quenched with saturated aqueous ammonium chloride (50 mL), then the resulting mixture was diluted with water (100 mL) and extracted with EA (150 mL×2). The combined organic layers were washed with saturated brine (20 mL), dried over anhydrous sodium sulfate, filtered and concentrated. The residue was purified by column chromatography on a silica gel eluted with PE/EA (v/v=20/1) to give the title compound as a yellow solid (11 g, 62%).

Step 3: (4-bromo-2-(methoxymethoxy)phenyl)(1-(3-bromo-6-methoxypyridin-2-yl) cyclopropyl)methanone Under nitrogen atmosphere, to a mixture of 1-(4-bromo-2-(methoxymethoxy)phenyl)-2-(3-bromo-6-methoxypyridin-2-yl)ethanone (2.0 g, 4.5 mmol) in toluene (60 mL) was added tetrabutylammonium hydrogen sulfate (0.15 g, 0.45 mmol) and a solution of sodium hydroxide (6.24 g, 156 mmol) in water (6 mL) at rt. The reaction mixture was stirred at rt for 10 mins, followed by addition of 1,2-dibromoethane (1.0 mL, 11.7 mmol) and then the mixture was stirred at rt overnight. The reaction mixture was diluted with water (50 mL) and extracted with EA (60 mL×2). The combined organic layers were washed with saturated brine (20 mL), dried over anhydrous sodium sulfate, filtered and concentrated in vacuo. The residue was purified by column chromatography eluted with PE/EA (v/v=30/1) to give the title compound as yellow oil (1.9 g, 90%).

$^1$H NMR (400 MHz, CDCl$_3$) δ 7.52 (d, J=8.6 Hz, 1H), 7.33-7.25 (m, 2H), 6.98 (d, J=8.2 Hz, 1H), 6.48 (d, J=8.6 Hz, 1H), 5.13 (s, 2H), 3.94 (s, 3H), 3.49 (s, 3H), 1.92-1.87 (m, 2H), 1.65-1.61 (m, 2H).

Step 4: (4-bromo-2-hydroxyphenyl)(1-(3-bromo-6-methoxypyridin-2-yl)cyclopropyl) methanone To a mixture of (4-bromo-2-(methoxymethoxy)phenyl)(1-(3-bromo-6-methoxypyridin-2-yl)cyclopropyl)methanone (2.24 g, 4.8 mmol) in THF (30 mL) was added hydrochloric acid (8 mL, 48 mmol, 6 M). The reaction mixture was heated to 50° C. and stirred for 3 h. The reaction mixture was cooled to rt, diluted with water (20 mL), and adjusted to alkalinity with potassium carbonate. The resulting mixture was extracted with EA (30 mL×2). The combined organic layers were washed with saturated brine (10 mL), dried over anhydrous sodium sulfate, filtered and the filtrate was concentrated in vacuo. The residue was purified by column chromatography eluted with PE/EA (v/v=20/1) to give the title compound as yellow oil (1.56 g, 77%).

Step 5: 5-bromo-2-(1-(3-bromo-6-methoxypyridin-2-yl)cyclopropanecarbonyl)phenyl methyl carbonate To a solution of (4-bromo-2-hydroxyphenyl)(1-(3-bromo-6-methoxypyridin-2-yl) cyclopropyl)methanone (1.56 g, 3.7 mmol) in anhydrous THF (40 mL) was added dropwise triethylamine (0.77 mL, 5.5 mmol) and chloromethyl formate (0.33 mL, 4.2 mmol) under an ice bath condition and nitrogen atmosphere. The reaction mixture was stirred for 1.5 h under the ice bath condition. The mixture was filtered to give a light yellow solution of the title compound (1.7 g, 96%) in THF and used in next step directly without concentration.

Step 6: 5-bromo-2-((1-(3-bromo-6-methoxypyridin-2-yl)cyclopropyl)methyl)phenol

To a sodium borohydride (0.552 g, 14.6 mmol) in water (20 mL) was added a solution of 5-bromo-2-(1-(3-bromo-6-methoxypyridin-2-yl)cyclopropanecarbonyl)phenyl methyl carbonate (1.7 g, 3.7 mmol) in THF (40 mL) under an ice bath. The reaction mixture was stirred at rt overnight, diluted with water (100 mL) and extracted with EA (100 mL×2). The combined organic layers were washed with saturated brine (20 mL), dried over anhydrous sodium sulfate, filtered and concentrated in vacuo. The residue was purified by column chromatography eluted with PE/EA (v/v=20/1) to give the title compound as yellow oil (1.3 g, 86%).

MS (ESI, pos. ion) m/z: 411.9 [M+H]$^+$.

Step 7: 7-bromo-2-methoxy-10H-spiro[benzo[6,7]oxepino[3,2-b]pyridine-11,1'-cyclopropane]

A mixture of cuprous iodide (28 mg, 0.15 mmol), N,N-dimethylglycine (30 mg, 0.30 mmol), cesium carbonate (470 mg, 1.4 mmol) and 5-bromo-2-((1-(3-bromo-6-methoxypyridin-2-yl) cyclopropyl)methyl)phenol (300 mg, 0.70 mmol) in 1,4-dioxane (20 mL) was heated to reflux and stirred for 2.5 h under nitrogen atmosphere. The reaction mixture was cooled to rt, filtered and the filtrate was concentrated under reduced pressure. The residue was purified by column chromatography eluted with PE/EA (v/v=20/1) to give the title compound as colourless oil (92 mg, 40%).

MS (ESI, pos. ion) m/z: 332.0 [M+H]$^+$.

Step 8: methyl 2-methoxy-10H-spiro[benzo[6,7]oxepino[3,2-b]pyridine-11,1'-cyclopropane]-7-carboxylate A mixture of 7-bromo-2-methoxy-10H-spiro[benzo[6,7]oxepino[3,2-b]pyridine-11,1'-cyclopropane] (0.44 g, 1.3 mmol), triethylamine (0.4 mL, 3.0 mmol) and [1,1'-bis(diphenylphosphino)ferrocene]dichloropalladium (10 mg, 0.015 mmol) in methanol (30 mL) was heated to 100° C. and stirred for 2 days in an autoclave under carbon monoxide (3.0 MPa). The reaction mixture was cooled to rt, concentrated to remove the solvent under reduced pressure. The residue was purified by column chromatography eluted with PE/EA (v/v=30/1) to give the title compound as a white solid (280 mg, 68%).

$^1$H NMR (400 MHz, CDCl$_3$) δ 7.86-7.80 (m, 2H), 7.41 (d, J=8.6 Hz, 1H), 7.25 (d, J=7.7 Hz, 1H), 6.45 (d, J=8.6 Hz, 1H), 3.92 (s, 3H), 3.78 (s, 3H), 3.10 (s, 2H), 1.43-1.40 (m, 2H), 0.86-0.82 (m, 2H).

Step 9: methyl 2-oxo-2,10-dihydro-1H-spiro[benzo[6,7]oxepino[3,2-b]pyridine-11,1'-cyclopropane]-7-carboxylate To a mixture of methyl 2-methoxy-10H-spiro[benzo[6,7]oxepino[3,2-b]pyridine-11,1'-cyclopropane]-7-carboxylate (280 mg, 0.9 mmol) and sodium iodide (270 mg, 1.8 mmol) in acetonitrile (9 mL) was added trimethyl chlorosilane (0.15 mL, 1.7 mmol) at rt. The reaction mixture was heated to 85° C. and stirred for 3 h, and then cooled to rt, quenched with saturated aqueous sodium thiosulfate (50 mL). The resulting mixture was extracted with EA (50 mL×2). The combined organic layers were washed with saturated brine (30 mL), dried over sodium sulfate, filtered, and the filtrate was concentrated in vacuo. The residue was purified by column chromatography eluted with dichloromethane/methanol (v/v=15/1) to give the title compound as a yellow solid (230 mg, 82%).

Step 10: methyl 2-((5-cyclopropyl-3-(2,6-dichlorophenyl)isoxazol-4-yl)methoxy)-10H-spiro[benzo[6,7]oxepino[3,2-b]pyridine-11,1'-cyclopropane]-7-carboxylate A mixture of 4-(chloromethyl)-5-cyclopropyl-3-(2,6-dichlorophenyl)isoxazole (350 mg, 1.2 mmol), methyl 2-oxo-2,10-dihydro-1H-spiro[benzo[6,7]oxepino[3,2-b]pyridine-11,1'-cyclopropane]-7-carboxylate (230 mg, 0.77 mmol) and potassium phosphate (330 mg, 1.6 mmol) in DMF (10 mL) was heated to 50° C. and stirred for 4 h. The mixture was then cooled to rt, diluted with water (10 mL) and extracted with EA (20 mL×2). The combined organic layers were washed with saturated brine (20 mL), dried over anhydrous sodium sulfate, filtered, and the filtrate was concentrated in vacuo. The residue was purified by column chromatography eluted with PE/EA (v/v=7/1) to give the title compound as a white solid (230 mg, 53%).

$^1$H NMR (400 MHz, CDCl$_3$) δ 7.85-7.79 (m, 2H), 7.36-7.30 (m, 3H), 7.26-7.17 (m, 2H), 6.28 (d, J=8.6 Hz, 1H), 5.01 (s, 2H), 3.92 (s, 3H), 3.06 (s, 2H), 2.17-2.09 (m, 1H), 1.31-1.28 (m, 4H), 1.17-1.10 (m, 2H), 0.83-0.78 (m, 2H).

Step 11: 2-((5-cyclopropyl-3-(2,6-dichlorophenyl)isoxazol-4-yl)methoxy)-10H-spiro[benzo[6,7]oxepino[3,2-b]pyridine-11,1'-cyclopropane]-7-carboxylic acid To a mixture of methyl 2-((5-cyclopropyl-3-(2,6-dichlorophenyl)isoxazol-4-yl) methoxy)-10H-spiro[benzo[6,7]oxepino[3,2-b]pyridine-11,1'-cyclopropane]-7-carboxylate (230 mg, 0.41 mmol) in a mixed solvent of THF (12 mL) and water (12 mL) was added sodium hydroxide (163 mg, 4.0 mmol). The reaction mixture was heated to 80° C. and stirred for 3 h. Then the mixture was cooled to rt, concentrated to remove most of the solvent under reduced pressure. The residue was diluted with water (10 mL), adjusted to acidity with hydrochloric acid (3 mL, 2 M) and extracted with EA (20 mL×2). The combined organic layers were washed with saturated brine (10 mL), dried over with anhydrous sodium sulfate, filtered and concentrated under reduced pressure to give the title compound as a white solid (190 mg, 85%).

MS (ESI, pos. ion) m/z: 549.0 [M+H]$^+$;
$^1$H NMR (600 MHz, CDCl$_3$) δ 7.91-7.87 (m, 2H), 7.37-7.31 (m, 3H), 7.27 (s, 1H), 7.24-7.19 (m, 1H), 6.29 (d, J=8.6 Hz, 1H), 5.02 (s, 2H), 3.09 (s, 2H), 2.16-2.11 (m, 1H), 1.33-1.30 (m, 2H), 1.30-1.27 (m, 2H), 1.16-1.11 (m, 2H), 0.84-0.81 (m, 2H).

Example 10: 2-((5-cyclopropyl-3-(2,6-dichlorophenyl)isoxazol-4-yl)methoxy)-11,11-difluoro-10,11-dihydrobenzo[6,7]oxepino[3,2-b]pyridine-7-carboxylic acid

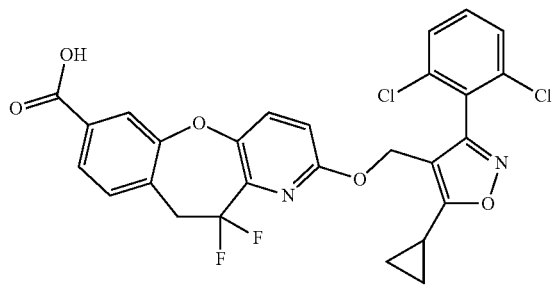 [SMILES: O=C(O)c1ccc2c(c1)Oc1ccc(OCc3c(-c4c(Cl)cccc4Cl)noc3C3CC3)nc1C(F)(F)C2]

Step 1: 1-(4-bromo-2-(methoxymethoxy)phenyl)-2-(3-bromo-6-methoxypyridin-2-yl)-2-fluoroethanone To a mixture of 1-(4-bromo-2-(methoxymethoxy)phenyl)-2-(3-bromo-6-methoxypyridin-2-yl)ethanone (3.00 g, 6.7 mmol) in DMF (40 mL) was added 1-chloromethyl-4-fluoro-1,4-diazoniabicyclo[2.2.2]octane bis(tetrafluoroborate) (4.50 g, 12.7 mmol) at rt. The reaction mixture was stirred at rt for 4 h and then diluted with water (200 mL). The resulting mixture was extracted with EA (150 mL×3). The combined organic layers were washed with saturated brine (20 mL), dried over with anhydrous sodium sulfate, filtered and the filtrate was concentrated in vacuo. The residue was purified by column chromatography eluted with PE/EA (v/v=10/1) to give the title compound as a white solid (2.91 g, 93%).

Step 2: 1-(4-bromo-2-(methoxymethoxy)phenyl)-2-(3-bromo-6-methoxypyridin-2-yl)-2,2-difluoroethanone To a mixture of 1-(4-bromo-2-(methoxymethoxy)phenyl)-2-(3-bromo-6-methoxypyridin-2-yl)-2-fluoroethanone (2.91 g, 6.3 mmol) in THF (60 mL) was added dropwise a solution of sodium bis(trimethylsilyl)amide in THF (9.4 mmol, 4.7 mL, 2.0 mol/L) at −78° C. under nitrogen atmosphere. The reaction mixture was stirred at this temperature for 30 mins, followed by addition of a solution of N-fluorobenzenesulfonimide (3.96 g, 12.6 mmol) in THF (20 mL). The mixture was stirred at this temperature for another 1 h and warmed to rt and stirred for 30 mins. The reaction mixture was quenched with saturated aqueous ammonium chloride (40 mL) and extracted with EA (30 mL×2). The combined organic layers were washed with saturated brine (20 mL), dried over anhydrous sodium sulfate, filtered and concentrated in vacuo. The residue was purified by column chromatography eluted with PE/EA (v/v=20/1) to give the title compound as yellow oil (2.6 g, 86%).

MS (ESI, pos. ion) m/z: 479.8 [M+H]$^+$;

Step 3: 1-(4-bromo-2-hydroxyphenyl)-2-(3-bromo-6-methoxypyridin-2-yl)-2,2-difluoroethanone Using 1-(4-bromo-2-(methoxymethoxy)phenyl)-2-(3-bromo-6-methoxypyridin-2-yl)-2,2-difluoroethanone (2.6 g, 5.4 mmol) as a starting material, the title compound was prepared according to the procedure described in step 4 of example 9 as yellow oil (2.1 g, 89%).

MS (ESI, neg. ion) m/z: 433.8 [M−H]$^-$.

Step 4: 5-bromo-2-(2-(3-bromo-6-methoxypyridin-2-yl)-2,2-difluoroacetyl)phenyl methyl carbonate Using 1-(4-bromo-2-hydroxyphenyl)-2-(3-bromo-6-methoxypyridin-2-yl)-2,2-difluoroethanone (2.3 g, 5.3 mmol) as a starting material, the title compound was prepared according to the procedure described in step 5 of example 9 as yellow oil (2.5 g, 95%).

Step 5: 5-bromo-2-(2-(3-bromo-6-methoxypyridin-2-yl)-2,2-difluoroethyl)phenol Using 5-bromo-2-(2-(3-bromo-6-methoxypyridin-2-yl)-2,2-difluoroacetyl)phenyl methyl carbonate (2.5 g, 5.0 mmol) as a starting material, the title compound was prepared according to the procedure described in step 6 of example 9 as yellow oil (0.3 g, 10%).

MS (ESI, neg. ion) m/z: 419.8 [M−H]$^-$.

Step 6: 7-bromo-11,11-difluoro-2-methoxy-10,11-dihydrobenzo[6,7]oxepino[3,2-b]pyridine Using 5-bromo-2-(2-(3-bromo-6-methoxypyridin-2-yl)-2,2-difluoroethyl)phenol) (1.3 g, 3.1 mmol) as a starting material, the title compound was prepared according to the procedure described in step 7 of example 9 as a white solid (0.25 g, 24%).

MS (ESI, pos. ion) m/z: 342.0 [M+H]$^+$;

Step 7: methyl 11,11-difluoro-2-methoxy-10,11-dihydrobenzo[6,7]oxepino[3,2-b]pyridine-7-carboxylate Using 7-bromo-11,11-difluoro-2-methoxy-10,11-dihydrobenzo[6,7]oxepino[3,2-b]pyridine (250 mg, 0.73 mmol) as a starting material, the title compound was prepared according to the procedure described in step 8 of example 9 as a yellow solid (40 mg, 20%).

$^1$H NMR (400 MHz, CDCl$_3$) δ 7.90 (d, J=7.9 Hz, 2H), 7.59 (d, J=8.9 Hz, 1H), 7.48 (d, J=7.6 Hz, 1H), 6.85 (d, J=8.8 Hz, 1H), 3.97 (s, 3H), 3.94 (s, 3H), 3.73 (t, J=14.0 Hz, 2H).

Step 8: methyl 11,11-difluoro-2-oxo-1,2,10,11-tetrahydrobenzo[6,7]oxepino[3,2-b]pyridine-7-carboxylate Using methyl 11,11-difluoro-2-methoxy-10,11-dihydrobenzo[6,7]oxepino[3,2-b]pyridine-7-carboxylate (70 mg, 0.22 mmol) as a starting material, the title compound was prepared according to the procedure described in step 9 of example 9 as a white solid (50 mg, 75%).

Step 9: methyl 2-((5-cyclopropyl-3-(2,6-dichlorophenyl)isoxazol-4-yl)methoxy)-11,11-difluoro-10,11-dihydrobenzo[6,7]oxepino[3,2-b]pyridine-7-carboxylate Using methyl 11,11-difluoro-2-oxo-1,2,10,11-tetrahydrobenzo[6,7]oxepino[3,2-b]pyridine-7-carboxylate (40 mg, 0.13 mmol) and 4-(chloromethyl)-5-cyclopropyl-3-(2,6-dichlorophenyl) isoxazole (59 mg, 0.2 mmol) as a starting material, the title compound was prepared according to the procedure described in step 10 of example 9 as colourless oil (57 mg, 76%).

Step 10: 2-((5-cyclopropyl-3-(2,6-dichlorophenyl)isoxazol-4-yl)methoxy)-11,11-difluoro-10,11-dihydrobenzo[6,7]oxepino[3,2-b]pyridine-7-carboxylic acid Using methyl 2-((5-cyclopropyl-3-(2,6-dichlorophenyl)isoxazol-4-yl)methoxy)-11,11-difluoro-10,11-dihydrobenzo[6,7]oxepino[3,2-b]pyridine-7-carboxylate (50 mg, 0.087 mmol) as a starting material, the title compound was prepared according to the procedure described in step 11 of example 9 as a light yellow solid (40 mg, 82%).

MS (ESI, pos. ion) m/z: 559.0 [M+H]$^+$;

$^1$H NMR (400 MHz, CDCl$_3$) δ 8.00-7.89 (m, 2H), 7.53 (dd, J=19.1, 8.3 Hz, 2H), 7.38 (d, J=8.0 Hz, 2H), 7.27-7.24 (m, 1H), 6.71 (d, J=8.8 Hz, 1H), 5.23 (s, 2H), 3.72 (t, J=13.9 Hz, 2H), 2.45-2.38 (m, 1H), 1.25-1.22 (m, 2H), 1.16-1.10 (m, 2H).

Example 11: 2-((5-cyclopropyl-3-(2,6-dichlorophenyl)isoxazol-4-yl)methoxy)-8-hydroxy-10,11-dihydrobenzo[6,7]oxepino[3,2-b]pyridine-7-carboxylic acid

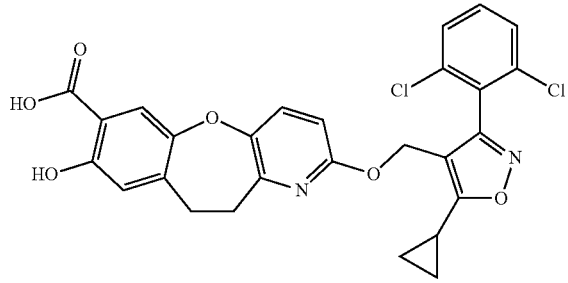 [SMILES: O=C(O)c1cc2c(cc1O)CCc1nc(OCc3c(-c4c(Cl)cccc4Cl)noc3C3CC3)ccc1O2]

Step 1: 6-methoxy-2-methyl-3-(4,4,5,5-tetramethyl-1,3,2-dioxaborolan-2-yl)pyridine A mixture of 3-bromo-6-methoxy-2-methylpyridine (10 g, 49.5 mmol), bis(pinacolato)diboron (16.3 g, 64.4 mmol), potassium acetate (14.6 g, 148.5 mmol) and [1,1'-bis(diphenylphosphino)ferrocene]dichloropalladium(II) (1.8 g, 2.5 mmol) in DMF (100 mL) was heated to 80° C. and stirred for 2.5 h under nitrogen atmosphere. Then the reaction mixture was cooled to rt and diluted with water (700 mL), extracted with EA (300 mL×2). The combined organic layers were washed with saturated brine (20 mL), dried over anhydrous sodium sulfate, filtered and the filtrate was concentrated in vacuo. The residue was purified by column chromatography on a silica gel eluted with PE/EA (v/v=40/1) to give the title compound as colourless oil (11 g, 89%).
$^1$H NMR (400 MHz, CDCl$_3$) δ 7.92 (d, J=8.2 Hz, 1H), 6.53 (d, J=8.2 Hz, 1H), 3.95 (s, 3H), 2.67 (s, 3H), 1.35 (s, 12H).

Step 2: 6-methoxy-2-methylpyridin-3-ol

To a mixture of 6-methoxy-2-methyl-3-(4,4,5,5-tetramethyl-1,3,2-dioxaborolan-2-yl)pyridine (12 g, 48.17 mmol) in THF (50 mL) was added aqueous sodium hydroxide (80 mL, 120 mmol, 1.5 M) and 30% hydrogen peroxide (16 mL, 144 mmol) under an ice bath condition. The reaction mixture was stirred at rt for 3 h, then diluted with water (20 mL) and extracted with EA (100 mL×2). The combined organic layers were washed with saturated brine (20 mL), dried over anhydrous sodium sulfate, filtered and the filtrate was concentrated under reduced pressure. The residue was purified by column chromatography eluted with PE/EA (v/v=10/1) to give the title compound as a white solid (2.3 g, 34%).
MS (ESI, pos. ion) m/z: 140.0 [M+H]$^+$.

Step 3: 3-((tert-butyldiphenylsilyl)oxy)-6-methoxy-2-methylpyridine

To a mixture of 6-methoxy-2-methylpyridin-3-ol (6.0 g, 43 mmol) in DMF (70 mL) were added imidazole (7.3 g, 108 mmol) and t-butyldiphenylchlorosilane (17 mL, 65 mmol) under an ice bath condition. The reaction mixture was stirred at rt for 3 h, then diluted with water (200 mL). The resulting mixture was extracted with EA (100 mL×2). The combined organic layers were washed with saturated brine (20 mL), dried over anhydrous sodium sulfate, filtered and the filtrate was concentrated under reduced pressure. The residue was purified by column chromatography eluted with PE/EA (v/v=20/1) to give the title compound as a white solid (15 g, 92%).
MS (ESI, pos. ion) m/z: 378.1 [M+H]$^+$.

Step 4: 2-(bromomethyl)-3-((tert-butyldiphenylsilyl)oxy)-6-methoxypyridine

Using 3-((tert-butyldiphenylsilyl)oxy)-6-methoxy-2-methylpyridine (15 g, 40 mmol) as a starting material, the title compound was prepared according to the procedure described in step 2 of example 1 as a white solid (17 g, 94%).
MS (ESI, pos. ion) m/z: 456.0 [M+H]$^+$.

Step 5: diethyl ((3-((tert-butyldiphenylsilyl)oxy)-6-methoxypyridin-2-yl)methyl)phosphonate Using 2-(bromomethyl)-3-((tert-butyldiphenylsilyl)oxy)-6-methoxypyridine (6.0 g, 13 mmol) as a starting material, the title compound was prepared according to the procedure described in step 3 of example 1 as colourless oil (5.8 g, 86%).

Step 6: 5-bromo-2-hydroxy-4-methylbenzoic acid

To a mixture of 2-hydroxy-4-methylbenzoic acid (24.5 g, 161 mmol) in methanol (300 mL) was added dropwise a solution of bromine (28 g, 180 mmol) in methanol (50 mL) at −20° C. and the reaction mixture was stirred for 0.5 h, then warmed to rt and stirred for another 1 h. The reaction was quenched with saturated aqueous sodium sulfite (100 mL). The reaction mixture was concentrated to remove methanol and the residue was diluted with water (50 mL). The mixture was filtered and the filtrate was dried to give a red-brown solid (33 g, 89%).
MS (ESI, pos. ion) m/z: 231.1 [M+H]$^+$.

Step 7: methyl 5-bromo-2-hydroxy-4-methylbenzoate

To a solution of 5-bromo-2-hydroxy-4-methylbenzoic acid (33 g, 143 mmol) in methanol (120 mL) was added concentrated sulfuric acid (3 mL, 58 mmol) under an ice bath. The mixture was heated to 75° C. and stirred overnight. The reaction mixture was cooled to rt and concentrated under reduced pressure to remove the solvent. The residue was diluted with water (500 mL), dried to give the title compound as a light yellow solid (33 g, 94%).

Step 8: methyl 2-acetoxy-5-bromo-4-methylbenzoate

Using methyl 5-bromo-2-hydroxy-4-methylbenzoate (10 g, 41 mmol) as a starting material, the title compound was prepared according to the procedure described in step 1 of example 1 as a white solid (9.5 g, 81%).
$^1$H NMR (600 MHz, CDCl$_3$) δ 8.19 (s, 1H), 7.01 (s, 1H), 3.88 (s, 3H), 2.44 (s, 3H), 2.36 (s, 3H).

Step 9: methyl 2-acetoxy-5-bromo-4-(dibromomethyl)benzoate

Under nitrogen atmosphere, to a mixture of methyl 2-acetoxy-5-bromo-4-methylbenzoate (8.0 g, 28 mmol) in tetrachloromethane (150 mL) were added N-bromosuccinimide (11.0 g, 62 mmol) and benzoyl peroxide (0.7 g, 2.8 mmol). Then the reaction mixture was heated to 80° C. and stirred overnight. The reaction was cooled to rt and quenched with saturated aqueous sodium bicarbonate (80 mL). The reaction mixture was extracted with EA (100 mL×2). The combined organic layers were washed with saturated brine (20 mL), dried over anhydrous sodium sulfate, filtered and the filtrate was concentrated under reduced pressure. The residue was purified by column chromatography eluted with PE/EA (v/v=10/1) to give the title compound as a light yellow solid (12.0 g, 97%).

$^1$H NMR (400 MHz, CDCl$_3$) δ 8.18 (s, 1H), 7.78 (s, 1H), 6.99 (s, 1H), 3.91 (s, 3H), 2.39 (s, 3H).

Step 10: methyl 2-acetoxy-5-bromo-4-formylbenzoate

To a mixture of methyl 2-acetoxy-5-bromo-4-(dibromomethyl)benzoate (12 g, 27 mmol) in acetonitrile (80 mL) was added a solution of silver nitrate (11.0 g, 66 mmol) in water (30 mL). The mixture was heated to 90° C. and stirred for 2 h, then cooled to rt and stirred overnight. The reaction mixture was diluted with water (200 mL) and extracted with EA (100 mL×2). The combined organic layers were washed with saturated brine (20 mL), dried over anhydrous sodium sulfate, filtered, and the filtrate was concentrated under reduced pressure. The residue was purified by column chromatography eluted with PE/EA (v/v=20/1) to give the title compound as a yellow solid (7.8 g, 96%).

MS (ESI, pos. ion) m/z: 300.9 [M+H]$^+$.

Step 11: methyl 5-bromo-4-formyl-2-hydroxybenzoate

Using methyl 2-acetoxy-5-bromo-4-formylbenzoate (8.0 g, 27 mmol) as a starting material, the title compound was prepared according to the procedure described in step 4 of example 1 as a light yellow solid (6.8 g, 98%).

Step 12: methyl 5-bromo-4-formyl-2-(methoxymethoxy)benzoate

Using methyl 5-bromo-4-formyl-2-hydroxybenzoate (6.8 g, 26 mmol) as a starting material, the title compound was prepared according to the procedure described in step 5 of example 1 as yellow oil (6.7 g, 84%).

Step 13: methyl 5-bromo-4-(2-(3-((tert-butyldiphenylsilyl)oxy)-6-methoxypyridin-2-yl)vinyl)-2-(methoxymethoxy)benzoate Using methyl 5-bromo-4-formyl-2-(methoxymethoxy) benzoate (2.8 g, 9.2 mmol) and diethyl ((3-((tert-butyldiphenylsilyl)oxy)-6-methoxypyridin-2-yl)methyl)phosphonate (5.9 g, 11 mmol) as a starting material, the title compound was prepared according to the procedure described in step 7 of example 1 as a yellow solid (4.4 g, 71%).

Step 14: methyl 5-bromo-4-(2-(3-((tert-butyldiphenylsilyl)oxy)-6-methoxypyridin-2-yl)ethyl)-2-(methoxymethoxy)benzoate Using methyl 5-bromo-4-(2-(3-((tert-butyldiphenylsilyl) oxy)-6-methoxypyridin-2-yl)vinyl)-2-(methoxymethoxy) benzoate (4.4 g, 6.6 mmol) as a starting material, the title compound was prepared according to the procedure described in step 4 of example 4 as yellow oil (3.3 g, 75%).

Step 15: methyl 5-bromo-4-(2-(3-hydroxy-6-methoxypyridin-2-yl)ethyl)-2-(methoxymethoxy) benzoate To a mixture of methyl 5-bromo-4-(2-(3-((tert-butyldiphenylsilyl)oxy)-6-methoxypyridin-2-yl)ethyl)-2-(methoxymethoxy)benzoate (3.3 g, 5.0 mmol) in THF (80 mL) was added a solution of tetrabutylammonium fluoride in THF (10 mL, 10 mmol, 1 mol/L) at rt. The reaction mixture was stirred at rt overnight, and then diluted with water (80 mL), extracted with EA (100 mL×2). The combined organic layers were washed with saturated brine (20 mL), dried over anhydrous sodium sulfate, filtered, and the filtrate was concentrated under reduced pressure. The residue was purified by column chromatography eluted with PE/EA (v/v=10/1) to give the title compound as a yellow solid (1.9 g, 90%).

Step 16: methyl 2-methoxy-8-(methoxymethoxy)-10,11-dihydrobenzo[6,7]oxepino[3,2-b]pyridine-7-carboxylate Using methyl 5-bromo-4-(2-(3-hydroxy-6-methoxypyridin-2-yl)ethyl)-2-(methoxymethoxy) benzoate (300 mg, 0.7 mmol) as a starting material, the title compound was prepared according to the procedure described in step 9 of example 1 as yellow oil (120 mg, 50%).

MS (ESI, pos. ion) m/z: 346.0 [M+H]$^+$.

Step 17: methyl 8-hydroxy-2-oxo-1,2,10,11-tetrahydrobenzo[6,7]oxepino[3,2-b]pyridine-7-carboxylate Using methyl 2-methoxy-8-(methoxymethoxy)-10,11-dihydrobenzo[6,7]oxepino[3,2-b]pyridine-7-carboxylate (1.0 g, 2.9 mmol) as a starting material, the title compound was prepared according to the procedure described in step 10 of example 1 as yellow oil (720 mg, 87%).

Step 18: methyl 2-((5-cyclopropyl-3-(2,6-dichlorophenyl)isoxazol-4-yl)methoxy)-8-hydroxy-10,11-dihydrobenzo[6,7]oxepino[3,2-b]pyridine-7-carboxylate Using methyl 8-hydroxy-2-oxo-1,2,10,11-tetrahydrobenzo[6,7]oxepino[3,2-b]pyridine-7-carboxylate (400 mg, 1.4 mmol) and 4-(chloromethyl)-5-cyclopropyl-3-(2,6-dichlorophenyl) isoxazole (420 mg, 1.4 mmol) as a starting material, the title compound was prepared according to the procedure described in step 11 of example 1 as colourless oil (105 mg, 14%).

$^1$H NMR (400 MHz, CDCl$_3$) δ 10.56 (s, 1H), 7.58 (s, 1H), 7.40-7.38 (m, 1H), 7.35-7.33 (m, 2H), 7.27-7.22 (m, 1H), 6.86 (s, 1H), 6.39 (d, J=8.7 Hz, 1H), 5.12 (s, 2H), 3.95 (s, 3H), 3.17-3.11 (m, 2H), 3.10-3.03 (m, 2H), 2.38-2.28 (m, 1H), 1.30-1.27 (m, 2H), 1.17-1.11 (m, 2H).

Step 19: 2-((5-cyclopropyl-3-(2,6-dichlorophenyl) isoxazol-4-yl)methoxy)-8-hydroxy-10,11-dihydrobenzo[6,7]oxepino[3,2-b]pyridine-7-carboxylic acid Using methyl 2-((5-cyclopropyl-3-(2,6-dichlorophenyl) isoxazol-4-yl)methoxy)-8-hydroxy-10,11-dihydrobenzo[6, 7]oxepino[3,2-b]pyridine-7-carboxylate (105 mg, 0.19 mmol) as a starting material, the title compound was prepared according to the procedure described in step 12 of example 1 as a white solid (50 mg, 49%).
MS (ESI, neg. ion) m/z: 536.8 [M–H]⁻;
$^1$H NMR (400 MHz, CDCl$_3$) δ 7.62 (s, 1H), 7.38-7.30 (m, 3H), 7.27-7.20 (m, 1H), 6.84 (s, 1H), 6.39 (d, J=8.5 Hz, 1H), 5.12 (s, 2H), 3.21-3.00 (m, 4H), 2.37-2.25 (m, 1H), 1.30-1.27 (m, 2H), 1.17-1.10 (m, 2H).

Example 12: 2-((5-cyclopropyl-3-(2,6-dichlorophenyl)isoxazol-4-yl)methoxy)-11,11-difluoro-10-hydroxy-10,11-dihydrobenzo[6,7]oxepino[3,2-b]pyridine-7-carboxylic acid

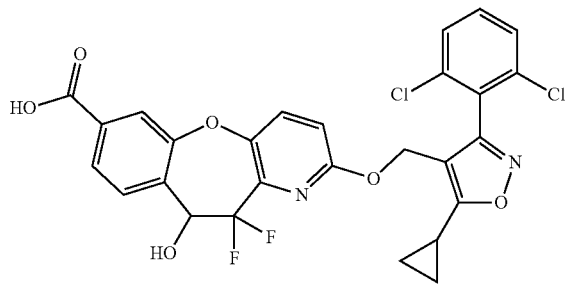 [SMILES: O=C(O)c1ccc2c(c1)Oc1ccc(OCc3c(-c4c(Cl)cccc4Cl)noc3C3CC3)nc1C(F)(F)C2O]

Step 1: 5-bromo-2-(2-(3-bromo-6-methoxypyridin-2-yl)-2,2-difluoro-1-hydroxyethyl)phenol To a mixture of 1-(4-bromo-2-hydroxyphenyl)-2-(3-bromo-6-methoxypyridin-2-yl)-2,2-difluoroethanone (0.1 g, 0.23 mmol) in ethanol (5 mL) was added sodium borohydride (0.040 g, 1.1 mmol) at rt. The reaction mixture was stirred at rt for 3 h, and then diluted with water (50 mL), extracted with EA (50 mL×3). The combined organic layers were washed with saturated brine (20 mL), dried over anhydrous sodium sulfate, filtered, and the filtrate was concentrated under reduced pressure. The residue was purified by column chromatography on a silica gel eluted with PE/EA (v/v=10/1) to give the title compound as colourless oil (0.090 g, 89%).

Step 2: 7-bromo-11,11-difluoro-2-methoxy-10,11-dihydrobenzo[6,7]oxepino[3,2-b]pyridin-10-ol Using 5-bromo-2-(2-(3-bromo-6-methoxypyridin-2-yl)-2,2-difluoro-1-hydroxyethyl)phenol (2.5 g, 5.7 mmol) as a starting material, the title compound was prepared according to the procedure described in step 7 of example 9 as a yellow solid (0.660 g, 32%).
MS (ESI, pos. ion) m/z: 358.0 [M+H]⁺.

Step 3: methyl 11,11-difluoro-10-hydroxy-2-methoxy-10,11-dihydrobenzo[6,7]oxepino[3,2-b]pyridine-7-carboxylate Using 7-bromo-11,11-difluoro-2-methoxy-10,11-dihydrobenzo[6,7]oxepino[3,2-b]pyridin-10-ol (660 mg, 1.8 mmol) as a starting material, the title compound was prepared according to the procedure described in step 8 of example 9 as a yellow solid (450 mg, 72%).
$^1$H NMR (400 MHz, CDCl$_3$) δ 7.98 (d, J=8.0 Hz, 1H), 7.90 (s, 1H), 7.79 (d, J=8.0 Hz, 1H), 7.60 (d, J=8.9 Hz, 1H), 6.88 (d, J=8.9 Hz, 1H), 5.56 (d, J=18.6 Hz, 1H), 3.98 (s, 3H), 3.95 (s, 3H), 3.05 (d, J=3.2 Hz, 1H).

Step 4: methyl 11,11-difluoro-10-hydroxy-2-oxo-1,2,10,11-tetrahydrobenzo[6,7]oxepino[3,2-b]pyridine-7-carboxylate Using methyl 11,11-difluoro-10-hydroxy-2-methoxy-10,11-dihydrobenzo[6,7]oxepino[3,2-b]pyridine-7-carboxylate (150 mg, 0.44 mmol) as a starting material, the title compound was prepared according to the procedure described in step 9 of example 9 as a white solid (120 mg, 83%).

Step 5: methyl 2-((5-cyclopropyl-3-(2,6-dichlorophenyl)isoxazol-4-yl)methoxy)-11,11-difluoro-10-hydroxy-10,11-dihydrobenzo[6,7]oxepino[3,2-b]pyridine-7-carboxylate Using methyl 11,11-difluoro-10-hydroxy-2-oxo-1,2,10,11-tetrahydrobenzo[6,7]oxepino[3,2-b]pyridine-7-carboxylate (120 mg, 0.37 mmol) and 4-(chloromethyl)-5-cyclopropyl-3-(2,6-dichlorophenyl)isoxazole (168 mg, 0.56 mmol) as a starting material, the title compound was prepared according to the procedure described in step 10 of example 9 as a white solid (160 mg, 73%).

Step 6: 2-((5-cyclopropyl-3-(2,6-dichlorophenyl)isoxazol-4-yl)methoxy)-11,11-difluoro-10-hydroxy-10,11-dihydrobenzo[6,7]oxepino[3,2-b]pyridine-7-carboxylic acid Using methyl 2-((5-cyclopropyl-3-(2,6-dichlorophenyl)isoxazol-4-yl)methoxy)-11,11-difluoro-10-hydroxy-10,11-dihydrobenzo[6,7]oxepino[3,2-b]pyridine-7-carboxylate (160 mg, 0.27 mmol) as a starting material, the title compound was prepared according to the procedure described in step 11 of example 9 as a light yellow solid (120 mg, 77%).
MS (ESI, pos. ion) m/z: 575.1 [M+H]⁺;
$^1$H NMR (400 MHz, CDCl$_3$) δ 8.03 (d, J=6.1 Hz, 1H), 7.92 (s, 1H), 7.80 (d, J=6.3 Hz, 1H), 7.55 (d, J=7.8 Hz, 1H), 7.44-7.33 (m, 2H), 7.28 (s, 1H), 6.73 (d, J=7.6 Hz, 1H), 5.54 (d, J=17.7 Hz, 1H), 5.24 (s, 2H), 3.25 (s, 1H), 2.46-2.34 (m, 1H), 1.34-1.26 (m, 2H), 1.16-1.08 (m, 2H).

Example 13: 2-((5-cyclopropyl-3-(2,6-dichlorophenyl)isoxazol-4-yl)methoxy)-11-methyl-10,11-dihydrobenzo[6,7]oxepino[3,2-b]pyridine-7-carboxylic acid

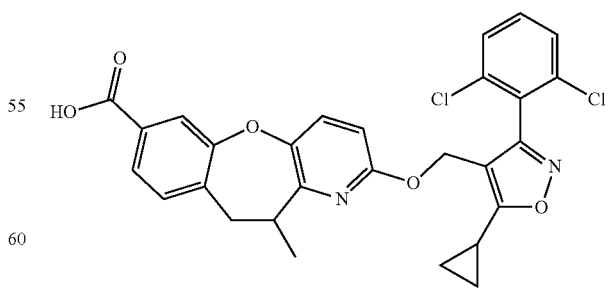

Using 1-(3-bromo-6-methoxypyridin-2-yl)ethanone as a starting material, the title compound was prepared according to the procedure described in example 8 as a white solid (80 mg).

MS (ESI, pos. ion) m/z: 537.0 [M+H]⁺;
¹H NMR (400 MHz, CDCl₃) δ 7.93-7.74 (m, 2H), 7.38-7.12 (m, 5H), 6.38 (d, J=8.6 Hz, 1H), 5.23 (d, J=12.8 Hz, 1H), 5.08 (d, J=12.8 Hz, 1H), 3.48-3.32 (m, 1H), 3.31-3.18 (m, 1H), 3.03-2.92 (m, 1H), 2.36-2.17 (m, 1H), 1.28-1.07 (m, 5H), 0.96-0.77 (m, 2H).

Example 14: 2-((5-cyclopropyl-3-(2,6-dichlorophenyl)isoxazol-4-yl)methoxy)-11-methyl benzo[6,7]oxepino[3,2-b]pyridine-7-carboxylic acid

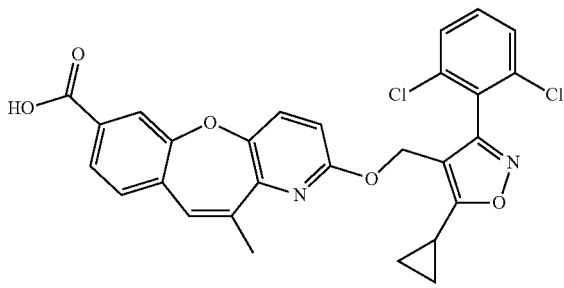 [SMILES: CC1=Cc2ccc(C(=O)O)cc2Oc2ccc(OCc3c(-c4c(Cl)cccc4Cl)noc3C3CC3)nc21]

Using 1-(3-bromo-6-methoxypyridin-2-yl)ethanone as a starting material, the title compound was prepared according to the procedure described in example 7 as a white solid (60 mg).
MS (ESI, pos. ion) m/z: 535.0 [M+H]⁺;
¹H NMR (400 MHz, CDCl₃) δ 7.97-7.79 (m, 2H), 7.38 (d, J=8.5 Hz, 1H), 7.27-7.18 (m, 3H), 7.08 (t, J=8.0 Hz, 1H), 6.84 (s, 1H), 6.57 (d, J=8.6 Hz, 1H), 5.23 (s, 2H), 2.37-2.19 (m, 4H), 1.19-1.08 (m, 2H), 0.93-0.83 (m, 2H).

Example 15: 2-((4-cyclopropyl-1-(2,6-dichlorophenyl)-1H-pyrazol-5-yl)methoxy)-11-methylbenzo[6,7]oxepino[3,2-b]pyridine-7-carboxylic acid

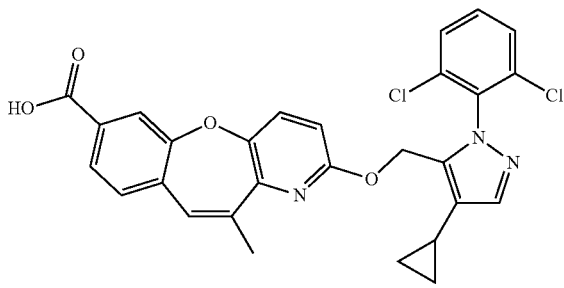 [SMILES: CC1=Cc2ccc(C(=O)O)cc2Oc2ccc(OCc3c(C4CC4)cnn3-c3c(Cl)cccc3Cl)nc21]

Step 1: methyl 2-((4-cyclopropyl-1-(2,6-dichlorophenyl)-1H-pyrazol-5-yl)methoxy)-11-methylbenzo[6,7]oxepino[3,2-b]pyridine-7-carboxylate Using methyl 11-methyl-2-oxo-1,2-dihydrobenzo[6,7]oxepino[3,2-b]pyridine-7-carboxylate (281 mg, 0.99 mmol) and 5-(chloromethyl)-4-cyclopropyl-1-(2,6-dichlorophenyl)-1H-pyrazole (200 mg, 0.66 mmol) (See synthetic method of compound Int-2-7 described in WO2016096115) as starting materials, the title compound was prepared according to the procedure described in step 10 of example 9 as a white solid (320 mg, 88%).

Step 2: 2-((4-cyclopropyl-1-(2,6-dichlorophenyl)-1H-pyrazol-5-yl)methoxy)-11-methylbenzo[6,7]oxepino[3,2-b]pyridine-7-carboxylic acid Using methyl 2-((4-cyclopropyl-1-(2,6-dichlorophenyl)-1H-pyrazol-5-yl)methoxy)-11-methylbenzo[6,7]oxepino[3,2-b]pyridine-7-carboxylate (320 mg, 0.58 mmol) as a starting material, the title compound was prepared according to the procedure described in step 11 of example 9 as a light yellow solid (130 mg, 42%).
MS (ESI, pos. ion) m/z: 534.0 [M+H]⁺;
¹H NMR (400 MHz, CDCl₃) δ 7.87 (d, J=8.1 Hz, 2H), 7.48 (s, 1H), 7.37 (d, J=8.7 Hz, 1H), 7.26-7.24 (m, 3H), 7.02 (t, J=8.1 Hz, 1H), 6.85 (s, 1H), 6.56 (d, J=8.7 Hz, 1H), 5.41 (s, 2H), 2.35 (s, 3H), 1.89-1.77 (m, 1H), 0.99-0.90 (m, 2H), 0.72-0.68 (m, 2H).

Example 16: 11-cyclopropyl-2-((5-cyclopropyl-3-(2,6-dichlorophenyl)isoxazol-4-yl)methoxy)benzo[6,7]oxepino[3,2-b]pyridine-7-carboxylic acid

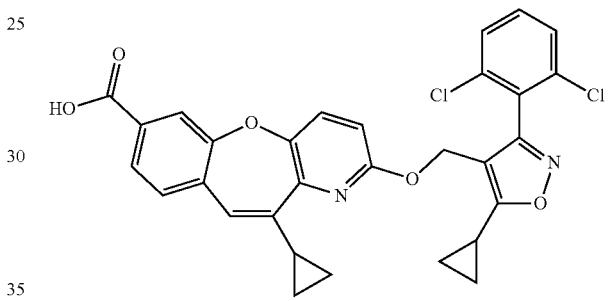

Step 1: methyl 4-(2-(3-bromo-6-methoxypyridin-2-yl)-2-cyclopropylvinyl)-3-(methoxymethoxy)benzoate Using (3-bromo-6-methoxypyridin-2-yl)(cyclopropyl)methanone (3.5 g, 13.7 mmol) and methyl 4-(diethoxyphosphorylmethyl)-3-(methoxymethoxyl) benzoate (5.68 g, 16 mmol) as starting materials, the title compound was prepared according to the procedure described in step 3 of example 7 as a yellow solid (1.8 g, 29%).

Step 2: methyl 4-(2-(3-bromo-6-methoxypyridin-2-yl)-2-cyclopropylvinyl)-3-hydroxybenzoate Using methyl 4-(2-(3-bromo-6-methoxypyridin-2-yl)-2-cyclopropylvinyl)-3-(methoxymethoxy)benzoate (1.0 g, 2.23 mmol) as a starting material, the title compound was prepared according to the procedure described in step 4 of example 7 as colourless oil (510 mg, 57%).
MS (ESI, pos. ion) m/z: 404.1 [M+H]⁺;

Step 3: methyl 11-cyclopropyl-2-methoxybenzo[6,7]oxepino[3,2-b]pyridine-7-carboxylate Using methyl 4-(2-(3-bromo-6-methoxypyridin-2-yl)-2-cyclopropylvinyl)-3-hydroxybenzoate (510 mg, 1.3 mmol) as a starting material, the title compound was prepared according to the procedure described in step 5 of example 7 as yellow oil (235 mg, 58%).

Step 4: methyl 11-cyclopropyl-2-oxo-1,2-dihydrobenzo[6,7]oxepino[3,2-b]pyridine-7-carboxylate Using methyl 11-cyclopropyl-2-methoxybenzo[6,7]oxepino[3,2-b]pyridine-7-carboxylate (240 mg, 0.73 mmol) as a starting material, the title compound was prepared according to the procedure described in step 6 of example 7 as a yellow solid (220 mg, 98%).

MS (ESI, pos. ion) m/z: 310.1 [M+H]$^+$;

Step 5: methyl 11-cyclopropyl-2-((5-cyclopropyl-3-(2,6-dichlorophenyl)isoxazol-4-yl)methoxy)benzo[6,7]oxepino[3,2-b]pyridine-7-carboxylate Using methyl 11-cyclopropyl-2-oxo-1,2-dihydrobenzo[6,7]oxepino[3,2-b]pyridine-7-carboxylate (220 mg, 0.71 mmol) and 4-(chloromethyl)-5-cyclopropyl-3-(2,6-dichlorophenyl)isooxazole (320 mg, 1.1 mmol) (See synthetic method of compound A6e described in WO2011020615) as starting materials, the title compound was prepared according to the procedure described in step 7 of example 7 as a white solid (310 mg, 76%).

Step 6: 11-cyclopropyl-2-((5-cyclopropyl-3-(2,6-dichlorophenyl)isoxazol-4-yl)methoxy)benzo[6,7]oxepino[3,2-b]pyridine-7-carboxylic acid Using methyl 11-cyclopropyl-2-((5-cyclopropyl-3-(2,6-dichlorophenyl)isoxazol-4-yl)methoxy)benzo[6,7]oxepino[3,2-b]pyridine-7-carboxylate (310 mg, 0.54 mmol) as a starting material, the title compound was prepared according to the procedure described in step 7 of example 7 as a light yellow solid (110 mg, 36%).

MS (ESI, pos. ion) m/z: 561.2 [M+H]$^+$;
$^1$H NMR (400 MHz, CDCl$_3$) δ 7.88-7.83 (m, 2H), 7.40 (d, J=8.7 Hz, 1H), 7.28-7.24 (m, 3H), 7.11 (t, J=8.1 Hz, 1H), 6.59 (d, J=8.7 Hz, 1H), 6.52 (s, 1H), 5.41 (s, 2H), 2.38-2.33 (m, 1H), 2.27-2.22 (m, 1H), 1.29-1.27 (m, 2H), 1.15-1.10 (m, 2H), 0.99-0.94 (m, 2H), 0.82-0.77 (m, 2H).

Example 17: 11-cyclopropyl-2-((5-cyclopropyl-3-(2,6-dichlorophenyl)isoxazol-4-yl)methoxy)-10,11-dihydrobenzo[6,7]oxepino[3,2-b]pyridine-7-carboxylic acid

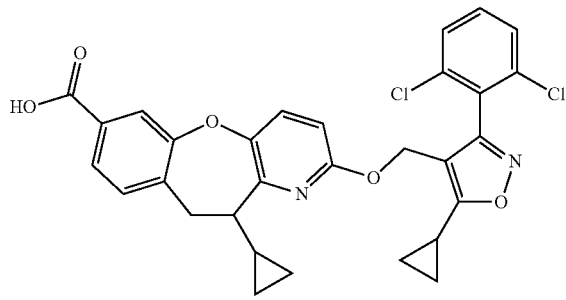 [SMILES: O=C(O)c1ccc2c(c1)Oc1ccc(OCc3c(-c4c(Cl)cccc4Cl)noc3C3CC3)nc1C(C1CC1)C2]

Step 1: methyl 11-cyclopropyl-2-((5-cyclopropyl-3-(2,6-dichlorophenyl)isoxazol-4-yl)methoxy)-10,11-dihydrobenzo[6,7]oxepino[3,2-b]pyridine-7-carboxylate Using methyl 11-cyclopropyl-2-((5-cyclopropyl-3-(2,6-dichlorophenyl)isoxazol-4-yl)methoxy)benzo[6,7]oxepino[3,2-b]pyridine-7-carboxylate (200 mg, 0.35 mmol) as a starting material, the title compound was prepared according to the procedure described in step 4 of example 4 as a white solid (120 mg, 61%).

Step 2: 11-cyclopropyl-2-((5-cyclopropyl-3-(2,6-dichlorophenyl)isoxazol-4-yl)methoxy)-10,11-dihydrobenzo[6,7]oxepino[3,2-b]pyridine-7-carboxylic acid Using methyl 11-cyclopropyl-2-((5-cyclopropyl-3-(2,6-dichlorophenyl)isoxazol-4-yl)methoxy)-10,11-dihydrobenzo[6,7]oxepino[3,2-b]pyridine-7-carboxylate (200 mg, 0.35 mmol) as a starting material, the title compound was prepared according to the procedure described in step 4 of example 4 as a white solid (40 mg, 20%).

MS (ESI, pos. ion) m/z: 563.0 [M+H]$^+$;
$^1$H NMR (400 MHz, CDCl$_3$) δ 7.93-7.78 (m, 2H), 7.42-7.31 (m, 4H), 7.27-7.19 (m, 1H), 6.44 (d, J=8.4 Hz, 1H), 5.24 (d, J=12.7 Hz, 1H), 5.07 (d, J=12.7 Hz, 1H), 3.51-3.40 (m, 1H), 3.14-3.04 (m, 1H), 2.40-2.31 (m, 1H), 2.28-2.18 (m, 1H), 1.20-1.07 (m, 3H), 0.95-0.67 (m, 3H), 0.61-0.41 (m, 3H).

Example 18: 2-((5-cyclopropyl-3-(2,6-dichlorophenyl)isoxazol-4-yl)methoxy)-10-methylbenzo[6,7]oxepino[3,2-b]pyridine-7-carboxylic acid

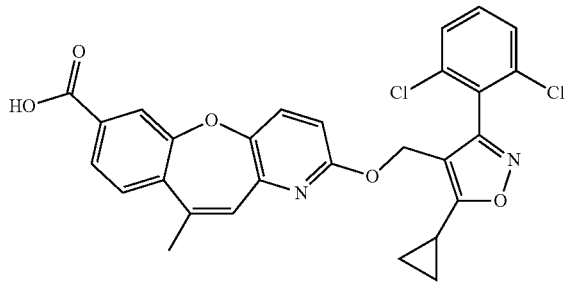 [SMILES: CC1=Cc2nc(OCc3c(-c4c(Cl)cccc4Cl)noc3C3CC3)ccc2Oc2cc(C(=O)O)ccc21]

Step 1: methyl 4-acetyl-3-(methoxymethoxy)benzoate

To a solution of methyl 4-acetyl-3-hydroxybenzoate (5.0 g, 26 mmol) and N,N-diisopropylethylamine (14 mL, 79 mmol) in DCM (80 mL) was added dropwise chloromethyl methyl ether (3 mL, 39.5 mmol) under ice bath and N$_2$ atmosphere. The mixture was then warmed to rt and stirred overnight. The reaction was quenched by adding water (100 mL) and extracted with DCM (80 mL×2). The organic phase was combined, washed with saturated saline (20 mL), dried over anhydrous Na$_2$SO$_4$, filtered and concentrated under reduced pressure. The residue was purified by a column chromatography using (PE/EA (v/v)=5/1) as eluent to give the title compound as light yellow oil (5.0 g, 82%).

Step 2: methyl 4-(1-(3-bromo-6-methoxypyridin-2-yl)prop-1-en-2-yl)-3-(methoxymethoxy)benzoate To a solution of diethyl ((3-bromo-6-methoxypyridine-2-yl) methyl) phosphate (5.96 g, 17.6 mmol) in DMF (20 mL) under ice bath was added 60% NaH (0.77 g, 19 mmol). The mixture was stirred for 0.5 h under ice bath and methyl 4-acetyl-3-(methoxymethoxy)benzoate (3.5 g, 15 mmol)

was added. And then the mixture was warmed to rt and stirred overnight, quenched with saturated ammonium chloride aqueous solution (10 mL) and extracted with EA (20 mL×2). The organic phase was combined, washed with saturated saline (20 mL), dried over anhydrous sodium sulfate, filtered and concentrated under reduced pressure. The residue was purified by a column chromatography using (PE/EA (v/v)=10/1) as eluent to give the title compound as yellow oil (2.9 g, 47%).

MS (ESI, pos. ion) m/z: 422.0 $[M+H]^+$;

Step 3: methyl 4-(1-(3-bromo-6-methoxypyridin-2-yl)prop-1-en-2-yl)-3-hydroxybenzoate To a solution of methyl 4-(1-(3-bromo-6-methoxypyridin-2-yl)prop-1-en-2-yl)-3-(methoxymethoxy)benzoate (2.9 g, 6.8 mmol) in THF (10 mL) was added hydrochloric acid (10 mL, 60 mmol, 6 M). The mixture was heated to 50° C. and stirred for 5 h. Then the reaction mixture was cooled to rt, diluted with water (20 mL), adjusted to alkaline by using potassium carbonate and extracted with EA (30 mL×2). The organic phase was combined, washed with saturated saline (10 mL), dried over anhydrous sodium sulfate, filtered and concentrated under reduced pressure. The residue was purified by a column chromatography using (PE/EA (v/v)=10/1) as eluent to give the title compound as yellow oil (2.3 g, 88%).

MS (ESI, pos. ion) m/z: 378.1 $[M+H]^+$;

Step 4: methyl 2-methoxy-10-methylbenzo[6,7]oxepino[3,2-b]pyridine-7-carboxylate A mixture of cuprous iodide (150 mg, 0.79 mmol), N,N-dimethylglycine (330 mg, 3.2 mmol), cesium carbonate (3.1 g, 9.5 mmol) and methyl 4-(1-(3-bromo-6-methoxypyridin-2-yl)prop-1-en-2-yl)-3-hydroxybenzoate (2.0 g, 5.3 mmol) in 1,4-dioxane (20 mL) was heated to reflux and stirred overnight. The reaction mixture was cooled to rt, filtered and concentrated under reduced pressure. The residue was purified by a column chromatography using (PE/EA (v/v)=10/1) as eluent to give the title compound as a yellow solid (1.0 g, 64%).

Step 5: methyl 10-methyl-2-oxo-1,2-dihydrobenzo[6,7]oxepino[3,2-b]pyridine-7-carboxylate To a solution of methyl 2-methoxy-10-methylbenzo[6,7]oxepino[3,2-b]pyridine-7-carboxylate (1.0 g, 3.4 mmol) and sodium iodide (1.5 g, 10 mmol) in MeCN (20 mL) was added trimethylchlorosilane (0.9 mL, 10 mmol). Then the reaction mixture was heated to 85° C. and stirred for 3 h, cooled to rt, quenched with saturated sodium thiosulfate aqueous solution (50 mL) and extracted with EA (50 mL×2). The organic phase was combined, washed with saturated saline (30 mL), dried over anhydrous sodium sulfate, filtered and concentrated under reduced pressure. The residue was purified by a column chromatography using (DCM/methanol (v/v)=30/1) as eluent to give the title compound as a yellow solid (950 mg, 100%).

MS (ESI, pos. ion) m/z: 284.0 $[M+H]^+$;

Step 6: methyl 2-((5-cyclopropyl-3-(2,6-dichlorophenyl)isoxazol-4-yl)methoxy)-10-methylbenzo[6,7]oxepino[3,2-b]pyridine-7-carboxylate A mixture of methyl 10-methyl-2-oxo-1,2-dihydrobenzo[6,7]oxepino[3,2-b]pyridine-7-carboxylate (950 mg, 3.4 mmol), 4-(chloromethyl)-5-cyclopropyl-3-(2,6-dichlorophenyl)isoxazole (2.0 g, 6.6 mmol) (See synthetic method of compound A6e in WO2011020615) and potassium phosphate (1.8 g, 8.4 mmol) in DMF (20 mL) was heated to 60° C. and stirred for 3 h. Then the reaction mixture was cooled to rt, diluted with water (40 mL) and extracted with EA (80 mL×2). The organic phase was combined, washed with saturated saline (20 mL), dried over anhydrous sodium sulfate, filtered and concentrated under reduced pressure. The residue was purified by a column chromatography using (PE/EA (v/v)=10/1) as eluent to give the title compound as a yellow solid (800 mg, 40%).

MS (ESI, pos. ion) m/z: 549.2 $[M+H]^+$;

Step 7: 2-((5-cyclopropyl-3-(2,6-dichlorophenyl)isoxazol-4-yl)methoxy)-10-methylbenzo[6,7]oxepino[3,2-b]pyridine-7-carboxylic acid To a mixed solution of methyl 2-((5-cyclopropyl-3-(2,6-dichlorophenyl)isoxazol-4-yl)methoxy)-10-methylbenzo[6,7]oxepino[3,2-b]pyridine-7-carboxylate (800 mg, 1.5 mmol) in THF (15 mL) and water (12 mL) was added sodium hydroxide (600 mg, 15 mmol). The mixture was heated to 60° C. and stirred overnight, concentrated under reduced pressure to remove most of the solvent, diluted with water (20 mL), adjusted to acidic with hydrochloric acid (25 mL, 1 M) and extracted with EA (30 mL×2). The organic phase was combined, washed with saturated saline (10 mL), dried over anhydrous sodium sulfate, filtered and concentrated under reduced pressure to give the title compound as a yellow solid (700 mg, 90%).

MS (ESI, pos. ion) m/z: 535.1 $[M+H]^+$;
$^1$H NMR (400 MHz, CDCl$_3$) δ 7.99-7.86 (m, 2H), 7.47 (d, J=8.1 Hz, 1H), 7.41-7.31 (m, 3H), 7.27-7.19 (m, 1H), 6.74 (s, 1H), 6.53 (d, J=8.7 Hz, 1H), 5.14 (s, 2H), 2.42 (s, 3H), 2.37-2.26 (m, 1H), 1.30-1.27 (m, 2H), 1.18-1.11 (m, 2H).

Example 19: 2-((5-cyclopropyl-3-(2,6-dichlorophenyl)isoxazol-4-yl)methoxy)-10-methyl-10,11-dihydrobenzo[6,7]oxepino[3,2-b]pyridine-7-carboxylic acid

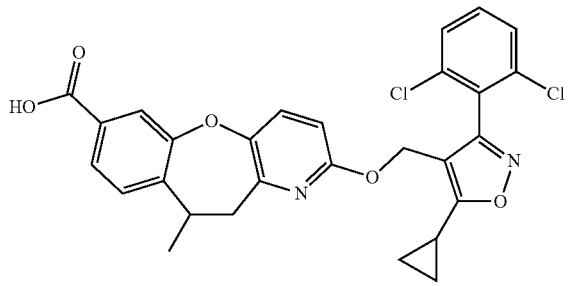 [SMILES: CC1Cc2nc(OCc3c(-c4c(Cl)cccc4Cl)noc3C3CC3)ccc2Oc2cc(C(=O)O)ccc21]

Step 1: methyl 4-(1-(3-bromo-6-methoxypyridin-2-yl)propan-2-yl)-3-(methoxymethoxy)benzoate A mixed solution of methyl 4-(1-(3-bromo-6-methoxypyridin-2-yl)prop-1-en-2-yl)-3-(methoxymethoxy)benzoate (2.9 g, 6.9 mmol), sodium acetate (3.4 g, 41 mmol) and 4-methylbenzenesulfonohydrazide (7.7 g, 41 mmol) in THF (20 mL) and water (20 mL) was heated to reflux and stirred overnight. Then the reaction mixture was cooled to rt, diluted with water (20 mL) and extracted with EA (100 mL×2). The organic phase was combined, washed with saturated saline (20 mL), dried over anhydrous sodium sulfate, filtered and concentrated under reduced pressure. The residue was purified by a column chromatography using (PE/EA (v/v)=4/1) as eluent to give the title compound as colourless oil (2.7 g, 93%).

MS (ESI, pos. ion) m/z: 424.0 [M+H]$^+$

Step 2: methyl 4-(1-(3-bromo-6-methoxypyridin-2-yl)propan-2-yl)-3-hydroxybenzoate To a solution of methyl 4-(1-(3-bromo-6-methoxypyridin-2-yl)propan-2-yl)-3-(methoxymethoxy)benzoate (2.7 g, 6.4 mmol) in THF (10 mL) was added hydrochloride acid (10 mL, 60 mmol, 6 M). The reaction mixture was heated to 50° C. and stirred overnight, cooled to rt, diluted with water (20 mL), adjusted to alkaline with potassium carbonate and extracted with EA (30 mL×2). The organic phase was combined, washed with saturated saline (10 mL), dried over anhydrous sodium sulfate, filtered and concentrated under reduced pressure. The residue was purified by a column chromatography using (PE/EA (v/v)=10/1) as eluent to give the title compound as colourless oil (2.3 g, 95%).

MS (ESI, pos. ion) m/z: 380.1 [M+H]$^+$

Step 3: methyl 2-methoxy-10-methyl-10,11-dihydrobenzo[6,7]oxepino[3,2-b]pyridine-7-carboxylate A solution of cuprous iodide (170 mg, 0.89 mmol), N,N-Dimethyl glycine (370 mg, 3.6 mmol), cesium carbonate (3.5 g, 11 mmol) and methyl 4-(1-(3-bromo-6-methoxypyridin-2-yl)propan-2-yl)-3-hydroxybenzoate (2.3 g, 6.0 mmol) in 1,4-dioxane (20 mL) was heated to reflux and stirred overnight under N$_2$ atmosphere. The reaction mixture was cooled to rt, filtered and concentrated under reduced pressure. The residue was purified by a column chromatography using (PE/EA (v/v)=10/1) as eluent to give the title compound as a yellow solid (1.1 g, 63%).

MS (ESI, pos. ion) m/z: 300.2 [M+H]$^+$

Step 4: methyl 10-methyl-2-oxo-1,2,10,11-tetrahydrobenzo[6,7]oxepino[3,2-b]pyridine-7-carboxylate To a solution of methyl 2-methoxy-10-methyl-10,11-dihydrobenzo[6,7]oxepino[3,2-b]pyridine-7-carboxylate (1.1 g, 3.7 mmol) and sodium iodide (1.7 g, 11 mmol) in MeCN (20 mL) was added trimethylchlorosilane (1.0 mL, 11.5 mmol). Then the reaction mixture was heated to 85° C. and stirred for 3 h, cooled to rt, quenched with saturated sodium thiosulfate aqueous solution (50 mL) and extracted with EA (50 mL×2). The organic phase was combined, washed with saturated saline (30 mL), dried over anhydrous sodium sulfate, filtered and concentrated under reduced pressure. The residue was purified by a column chromatography using (DCM/methanol (v/v)=30/1) as eluent to give the title compound as a yellow solid (1.0 g, 95%).

Step 5: methyl 2-((5-cyclopropyl-3-(2,6-dichlorophenyl)isoxazol-4-yl)methoxy)-10-methyl-1,11-dihydrobenzo[6,7]oxepino[3,2-b]pyridine-7-carboxylate A mixture of methyl 10-methyl-2-oxo-1,2,10,11-tetrahydrobenzo[6,7]oxepino[3,2-b]pyridine-7-carboxylate (1.0 g, 3.5 mmol), 4-(chloromethyl)-5-cyclopropyl-3-(2,6-dichlorophenyl)isoxazole (1.1 g, 3.6 mmol) (See synthetic method of compound A6e in WO2011020615) and potassium phosphate (1.5 g, 7.1 mmol) in DMF (10 mL) was heated to 60° C. and stirred for 3 h. Then the reaction mixture was cooled to rt, diluted with water (40 mL) and extracted with EA (80 mL×2). The organic phase was combined, washed with saturated saline (20 mL), dried over anhydrous sodium sulfate, filtered and concentrated under reduced pressure. The residue was purified by a column chromatography using (PE/EA (v/v)=50/1) as eluent to give the title compound as a light yellow solid (800 mg, 40%).

MS (ESI, pos. ion) m/z: 551.2 [M+H]$^+$;

Step 6: 2-((5-cyclopropyl-3-(2,6-dichlorophenyl)isoxazol-4-yl)methoxy)-10-methyl-1,11-dihydrobenzo[6,7]oxepino[3,2-b]pyridine-7-carboxylic acid To a mixed solution of methyl 2-((5-cyclopropyl-3-(2,6-dichlorophenyl)isoxazol-4-yl)methoxy)-10-methyl-10,11-dihydrobenzo[6,7]oxepino[3,2-b]pyridine-7-carboxylate (1.0 g, 1.8 mmol) in THF (5 mL) and water (5 mL) was added lithium hydroxide monohydrate (230 mg, 5.5 mmol). The mixture was heated to 60° C. and stirred for 4 h, concentrated under reduced pressure to remove most of the solvent, diluted with water (20 mL), adjusted to acidic with hydrochloric acid (10 mL, 1 M) and extracted with EA (30 mL×2). The organic phase was combined, washed with saturated saline (10 mL), dried over anhydrous sodium sulfate, filtered and concentrated under reduced pressure to give the title compound as a white solid (870 mg, 89%).

MS (ESI, pos. ion) m/z: 537.2 [M+H]$^+$;

1H NMR (400 MHz, CDCl$_3$) δ 7.95-7.71 (m, 2H), 7.42-7.29 (m, 4H), 7.26-7.17 (m, 1H), 6.39 (d, J=8.6 Hz, 1H), 5.12 (s, 2H), 3.77-3.54 (m, 1H), 3.29-3.16 (m, 1H), 2.85-2.74 (m, 1H), 2.35-2.29 (m, 1H), 1.45-1.37 (m, 2H), 1.34-1.23 (m, 3H), 1.19-1.06 (m, 2H).

Example 20: TR-FRET Farnesoid X Receptor Coactivator Assay

Purchasing invitrogen PV4833 kits. The procedure refers to LanthaScreen™ TR-FRET Farnesoid X Receptor Coactivator Assay First, the required amount of the compound was weighed and dissolved in 100% DMSO at the maximum concentration of 3000 µM. The solution at the maximum concentration was diluted by 3-fold serial dilution in DMSO to get 10 concentrations;

Second, the above prepared solutions of different concentrations were diluted to 50-fold with a buffer supplied with the kit, to 2× compound solution, followed by mixing and then 10 µL of the diluted solution was added to a 384 well plate;

Third, FXR-LBD was diluted with a buffer to 4× solution, and 5 µL of the diluent was added to the 384 well plate of second step;

Fourth, Fluorescein-SRC2-2 and Tb anti-GST antibody were diluted to 4× Fluorescein-SRC2-2 and Tb anti-GST antibody solution. Then two reagents were mixed together, and 5 µL of the mixture was added to the 384 well plate of third step;

Finally, the solution of the 384 well above was mixed uniformly by centrifuging, and then incubated at room temperature for 1 h. Then the TR-FRET Endpoint method was used for measuring the solution at wavelengths of 520 nm, 495 nm and 337 nm. EC$_{50}$ values were calculated according to the measured value of ER=520 nm/495 nm.

The TR-FRET farnesoid X receptor coactivator assay results of the partial compounds of the invention are shown in Table 2

TABLE 2

Test results of TR-FRET farnesoid X receptor protein coactivator activity

| Compound No. | $EC_{50}$ (nM) |
|---|---|
| Example 1 | 49.3 |
| Example 2 | 5.1 |
| Example 3 | 76.1 |
| Example 4 | 60.4 |
| Example 5 | 25.7 |
| Example 6 | 31.0 |
| Example 11 | 17.0 |
| Example 13 | 19.5 |
| Example 14 | 15.5 |

3. Conclusion:

$EC_{50}$ values of the partial example compounds in Table 2 indicated that the compounds of the present invention showed good farnesoid X receptor activation activity.

Example 21 Mammalian One Hybrid (M1H) Assay

Mammalian one hybrid technology is also called chimeric receptor gene assay. Based on the GAL4 chimera receptor assay, the activity of compounds which mediated activation of FXR was detected by dual luciferase reporter assay. The methods were as follows: cDNA encoding the FXR ligand binding domain (LBD), the yeast GAL4 DNA binding domain (DBD) and the *Renilla* luciferase DNA were fused to construct a chimera expression plasmid pBIND-FXR (Promega). The GeneBank number of cDNA of is Q96RI1.2, and the corresponding amino acid sequence is 261-481. The plasmid pG5Luc (Promega) was used as the reporter plasmid, containing the GAL4 upstream activation sequence (UAS) and the Firefly luciferase receptor gene. All GAL4 reporter gene assays were done in HEK293 cells. Cells were cultured at 37° C., 5% $CO_2$ under humidified conditions. The transfection mixture contains pBIND-FXR (25 ng/well), pG5Luc (25 ng/well), transfection reagent FuGENE HD (0.15 μl/well) and no FBS media (1.85 μl/well). The contents were mixed completely and incubated the mixtures for 15 minutes at room temperature. The volume of the transfection mixture was 2.5 μl/well. Trypsinized and diluted the cell slurry at a density of 600,000 cells/well (100 μl/well for 96-well plate). Then added required volume of transfection mixture prepared previously into the cell slurry, and dispensed 100 μl/well of the cell slurry into the 96-well plate and incubated the plate for 24 hours at 37° C., 5% $CO_2$ under humidified conditions. Compounds prediluted in complete medium were added into each well and then incubated at 37° C., 5% $CO_2$ under humidified conditions for 18 hours. The firefly and *renilla* luciferase signal was assayed by Promega's Dual Luciferase Reporter Assay System.

The % Activation value was calculated by the following equation: Activation %=[(X−Min)/(Max−Min)]×100%. "X" is the "F/R" value from compounds. "F/R" means "Firefly/*Renilla*". "Min" is the mean "F/R" value from no compound control. "Max" is the mean "F/R" value from reference compound control. Finally, the $EC_{50}$ value of each compounds were calculated by GraphPrism 5.0.

The results of GAL4 reporter gene test of the partial compounds of the invention are shown in Table 3.

TABLE 3

Result of GAL4 reporter gene test

| Example | $EC_{50}$ (nM) |
|---|---|
| example 5 | 104 |
| example 7 | 11 |
| example 8 | 26 |
| example 9 | 2 |
| example 10 | 12 |
| example 11 | 105 |
| example 12 | 136 |
| example 13 | 9 |
| example 14 | 12 |
| example 15 | 13 |
| example 16 | 5 |
| example 17 | 65 |
| example 18 | 93 |

$EC_{50}$ values of the partial example compounds in Table 3 indicated that the compounds of the present invention showed good FXR agonistic potency and then regulated expressions of downstream genes.

Example 22 Pharmacokinetics Test

Experimental animals: six healthy adult male SD rats (purchased from Hunan SJA Laboratory Animal Co. Ltd.) were divided into two groups, three rats in each group, and the two groups were given intravenous injection and oral administration respectively.

Drug preparation: a quantity of a compound of the present invention was weighed, and 5% DMSO, 10% Kolliphor HS15 and 85% saline (0.9%) were added to give target concentrations of the compound solution.

Administration and sample collection: animals were fasted for 12 h before administration, and fed at the time point of 3 hours after the administration. SD rats of one group were given intravenous injection (IV, 1 mg/kg) via hind legs and SD rats of the other group were given oral administration (PO, 5 mg/kg) respectively. Then blood was collected in the rat tail vein at the time point of 0, 0.083, 0.25, 0.5, 1, 2, 4, 6, 8, 24 h respectively, and the blood volume was about 200-400 μL/time point. After the collection of whole blood at each time point, the collected blood was set in K2EDTA anticoagulant tube, and the tube was placed in the incubator with ice packs. All samples were centrifuged for 5 min at 4° C. at 4600 r/min within 15 min. Plasma was separated and collected. The concentrations of different compounds in the plasma of the rats after administration were measured using LC/MS/MS method, and the pharmacokinetic parameters were calculated according to the curve of the drug concentration-time.

Pharmacokinetic properties of the compounds of the present invention were tested by the experiment above, and the pharmacokinetic parameters of the partial example compounds were shown in Table 4.

TABLE 4

Pharmacokinetic activity of the compound of the invention

| Compound No. | Route of adminstration | Dosage (mg/kg) | F(%) | $AUC_{INF}$ (h*ng/ml) | $AUC_{last}$ (h*ng/ml) | Cl (ml/min/kg) | $C_{max}$ (ng/ml) | $MRT_{INF}$ (h) | $T_{1/2}$ (h) | $T_{max}$ (h) | $V_{ss}$ (l/kg) |
|---|---|---|---|---|---|---|---|---|---|---|---|
| example 1 | iv | 1 | 55 | 1540 | 1540 | 11.2 | 1890 | 0.792 | 0.723 | 0.083 | 0.522 |
|  | po | 5 |  | 4210 | 4180 | N/A | 2760 | 1.32 | 0.914 | 0.500 | N/A |
| example 2 | iv | 1 | 72 | 1150 | 1150 | 14.8 | 2060 | 0.549 | 0.884 | 0.083 | 0.479 |
|  | po | 5 |  | 4110 | 4110 | N/A | 3640 | 0.931 | 0.71 | 0.500 | N/A |
| example 5 | iv | 1 | 95 | 1580 | 1580 | 10.6 | 3040 | 0.548 | 0.682 | 0.083 | 0.344 |
|  | po | 5 |  | 7480 | 7450 | N/A | 6430 | 1.07 | 0.839 | 0.500 | N/A |
| example 10 | iv | 1 | 88 | 1330 | 1330 | 12.6 | 3020 | 0.429 | 0.794 | 0.083 | 0.322 |
|  | po | 5 |  | 5840 | 5790 | N/A | 3760 | 1.38 | 0.957 | 0.500 | N/A |

The results of the partial example showed in Table 4 indicated that blood concentrations and exposure levels of the rats were high after oral administration of the compounds of the present invention, clear rate of the compound was low, and bioavailability of the compound was high. So the compounds of the present invention had good pharmacokinetic activity.

Finally, it should be noted that there are other ways to practice the invention. Accordingly, embodiments of the present invention is to be described as examples, but the present invention is not limited to the contents described herein, and further modifications within the scope of the present invention or the equivalents added in the claims are all examples within the scope of the invention. All publications or patents cited herein are incorporated by reference in this invention.

The invention claimed is:

1. A compound having Formula (I) or a stereoisomer, a geometric isomer, a tautomer, an N-oxide, a hydrate, a solvate, or a pharmaceutically acceptable salt thereof,

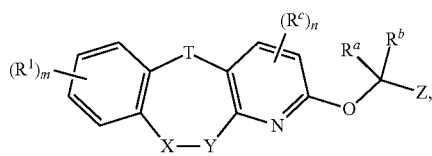

(I)

wherein:
T is —NH—, —O—, —S—, —C(=O)— or —CH$_2$—;
each of X and Y is independently a bond, —O—, —S(=O)$_t$—, —NR$^x$—, —CR$^y$R$^z$— or —C(=O)—, or —X—Y— is —CHR$^h$—CHR$^k$— or —CR$^y$=CR$^z$—;
each R$^x$ is independently hydrogen, deuterium, alkyl, aminoalkyl, haloalkyl, cycloalkyl, heterocyclyl, aryl, halo-substituted aryl or arylalkyl;
each R$^y$ and R$^z$ is independently hydrogen, deuterium, F, Cl, Br, I, hydroxy, amino, nitro, cyano, alkyl, haloalkyl, hydroxyalkyl, aminoalkyl, alkoxy, alkylamino, alkenyl, alkynyl, cycloalkyl, heterocyclyl, aryl, halo-substituted aryl or arylalkyl; or R$^y$ and R$^z$ together with the same carbon atom to which they are attached, independently and optionally form a cycloalkane ring or a heterocyclic ring, and wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;
each of R$^h$ and R$^k$ is independently hydrogen, deuterium, F, Cl, Br, I, hydroxy, amino, nitro, cyano, methyl, ethyl, isopropyl or trifluoromethyl; or R$^h$ and R$^k$, together with the carbon atoms to which they are attached, form a cycloalkane ring or a heterocyclic ring, wherein the cycloalkane ring and heterocyclic ring is independently and optionally substituted with substituents selected from F, Cl, Br, I, hydroxy, amino, nitro, cyano, methyl, ethyl, isopropyl and trifluoromethyl;
each of R$^a$ and R$^b$ is independently hydrogen, deuterium or C$_{1-3}$ alkyl;
each R$^c$ is independently hydrogen, deuterium, F, Cl, Br, I, oxo, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxymethyl, isopropoxymethyl, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—C$_{1-3}$ alkyl, —C(=O)NHS(=O)$_2$—C$_{1-3}$ alkyl, —C(=O)NHS(=O)$_2$-phenyl, —C(=O)NH—C$_{1-3}$ alkylene-S(=O)$_2$OH, —C(=O)NH—C$_{1-3}$ alkylene-C(=O)OH, —S(=O)$_2$NH$_2$, —S(=O)$_2$OH, —S(=O)$_2$—C$_{1-3}$ alkyl, —C(=O)NH$_2$ or —C(=O)N(CH$_3$)$_2$;
each R$^1$ is independently hydrogen, deuterium, F, Cl, Br, I, hydroxy, amino, nitro, cyano, alkyl, haloalkyl, hydroxyalkyl, aminoalkyl, alkoxy, alkylamino, haloalkoxy, alkoxyalkyl, alkenyl, alkynyl, cycloalkyl, cycloalkoxy, cycloalkylalkyl, heterocyclyl, heterocyclylalkyl, aryl, halo-substituted aryl, arylalkyl, heteroaryl, -L$^1$-C(=O)OR$^8$, -L$^1$-S(=O)$_t$R$^9$, —O-L$^2$-C(=O)OR$^8$, —O-L$^2$-S(=O)$_t$R$^9$, —C(=O)NR$^{10}$R$^{11}$, —C(=O)N(R$^{10}$)S(=O)$_2$R$^9$, —C(=NR$^{10}$)NR$^{10}$R$^{11}$, —C(=O)N(R$^{10}$)-L$^3$-S(=O)$_2$OR$^8$, —C(=O)N(R$^{10}$)C(=O)OR$^8$ or —C(=O)N(R$^{10}$)-L$^3$-C(=O)OR$^8$; or two adjacent R$^1$, together with the ring atoms to which they are attached, independently and optionally form a carbocyclic ring, heterocyclic ring, aromatic ring or heteroaromatic ring, and wherein each R$^1$ is independently and optionally substituted with one or more R$^{12}$;
each R$^8$ is independently hydrogen, deuterium, alkyl, aminoalkyl, alkenyl, alkynyl, haloalkyl, cycloalkyl, heterocyclyl or aryl;
each R$^9$ is independently hydrogen, deuterium, hydroxy, amino, alkyl, aminoalkyl, alkenyl, alkynyl, haloalkyl, cycloalkyl, heterocyclyl, aryl or —NR$^{10}$R$^{11}$;
each R$^{10}$ and R$^{11}$ is independently hydrogen, deuterium, alkyl, aminoalkyl, alkenyl, alkynyl, haloalkyl, cycloalkyl, heterocyclyl or aryl; or R[10] and R[11], together with the nitrogen atom to which they are attached, independently and optionally form a heterocyclic ring or heteroaromatic ring;

each R[12] is independently hydrogen, deuterium, F, Cl, Br, I, oxo, hydroxy, amino, nitro, cyano, alkyl, haloalkyl, alkoxy, alkylamino, alkenyl, alkynyl, cycloalkyl, heterocyclyl, aryl or heteroaryl;

each L[1] is independently a bond, —NH—, —C(=O)—, $C_{1-3}$ alkylene, $C_{2-4}$ alkenylene or $C_{2-4}$ alkynylene;

each L[2] is independently $C_{1-3}$ alkylene, $C_{2-4}$ alkenylene or $C_{2-4}$ alkynylene;

each L[3] is independently a bond or $C_{1-3}$ alkylene;

Z is

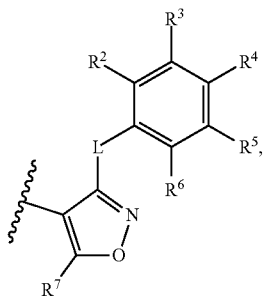 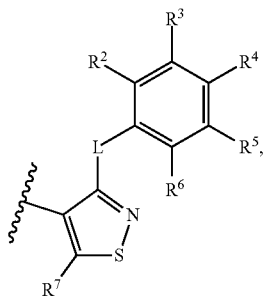

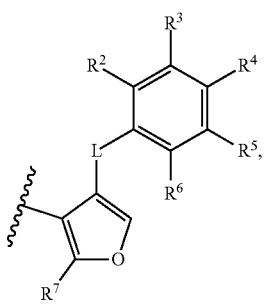 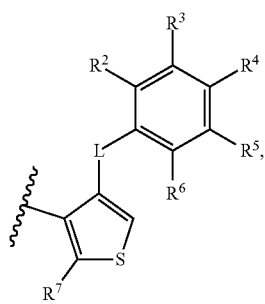

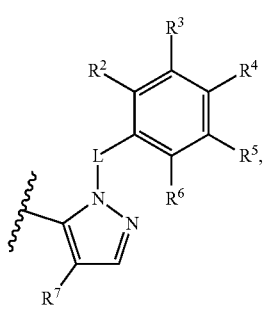 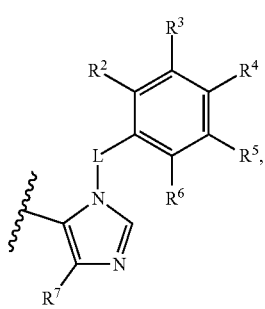

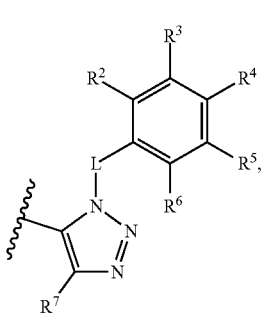 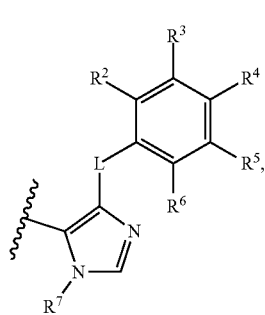

-continued

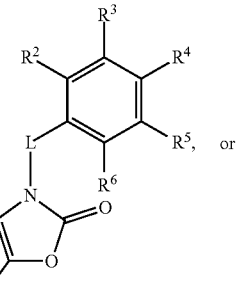, or

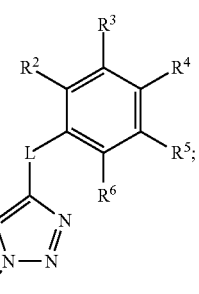;

each L is independently a bond, —O—, —S—, —NH—, —CH$_2$—, —CH$_2$—CH$_2$—, —O—CH$_2$—, —O—CH$_2$—CH$_2$— or —CH$_2$—O—CH$_2$—;

each R[2], R[3], R[4], R[5] and R[6] is independently hydrogen, deuterium, F, Cl, Br, I, hydroxy, amino, nitro, cyano, $C_{1-3}$ alkyl, $C_{1-3}$ haloalkyl, $C_{1-3}$ alkoxy or $C_{1-3}$ haloalkoxy;

each R[7] is independently hydrogen, deuterium, F, Cl, Br, I, hydroxy, amino, nitro, cyano, $C_{1-6}$ alkyl, $C_{1-6}$ hydroxyalkyl, $C_{1-6}$ haloalkyl, $C_{1-6}$ alkoxy, $C_{1-6}$ alkylamino, $C_{1-6}$ alkoxy-$C_{1-6}$ alkyl, $C_{3-6}$ cycloalkyl or $C_{2-6}$ heterocyclyl, and wherein the $C_{3-6}$ cycloalkyl and $C_{2-6}$ heterocyclyl is independently and optionally substituted with substituents selected from F, Cl, Br, I, hydroxy, amino, nitro and cyano;

m is 0, 1, 2, 3 or 4;

n is 0, 1 or 2; and each t is independently 0, 1 or 2;

with the proviso that a compound having formula (I) is not:

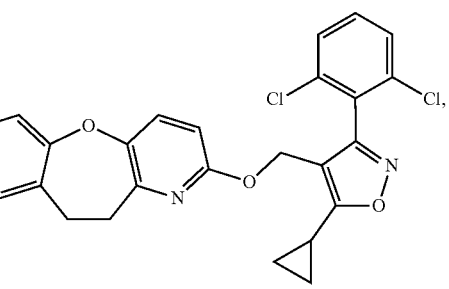

101
-continued
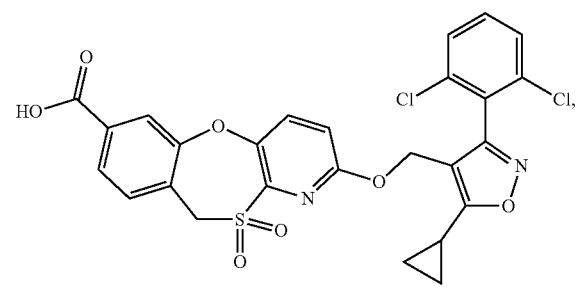
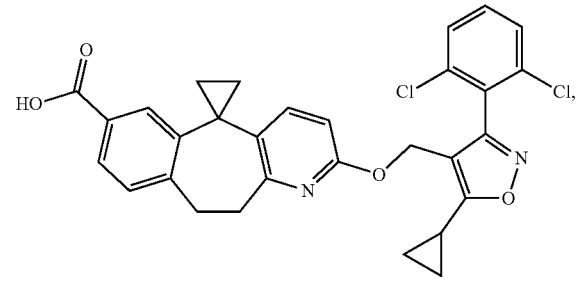
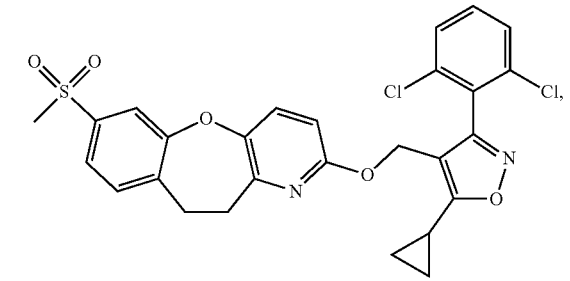
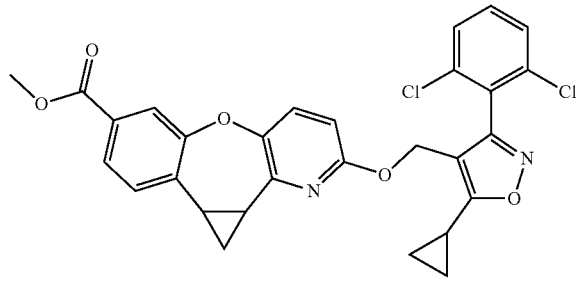
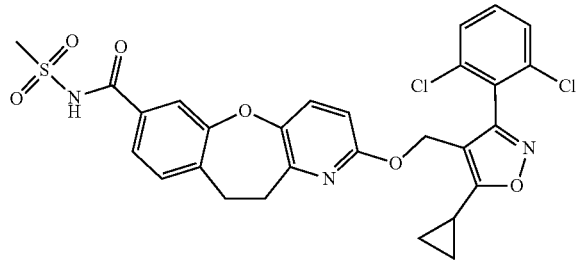
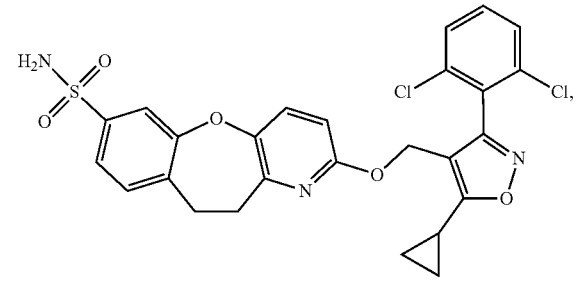
102
-continued
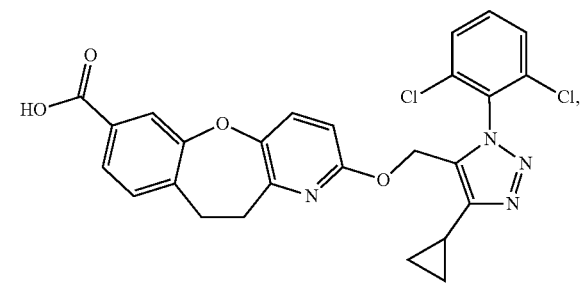
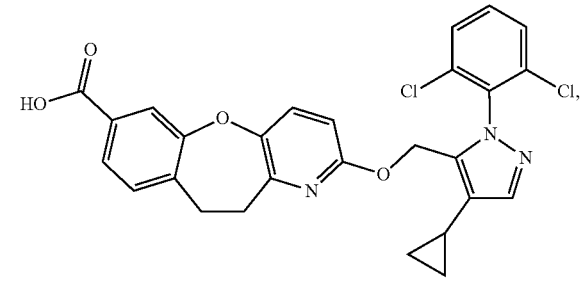
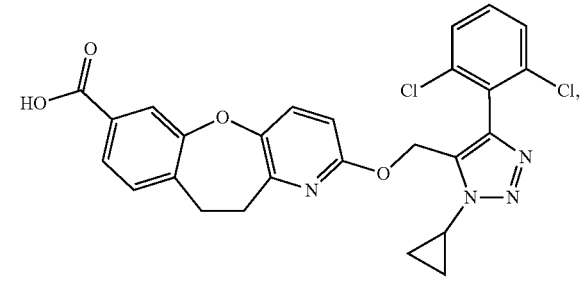
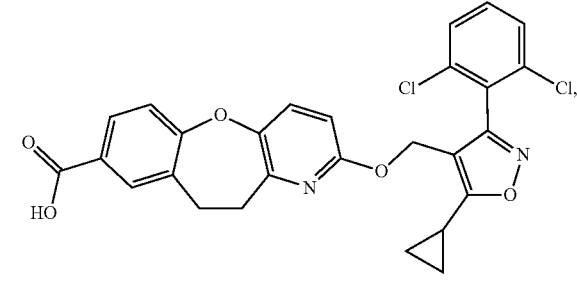
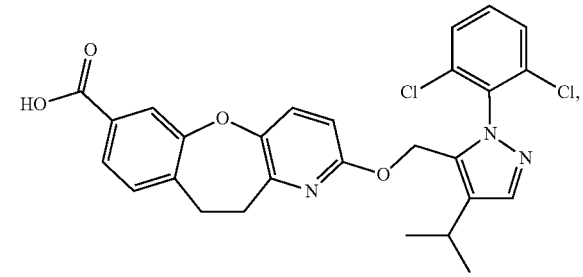
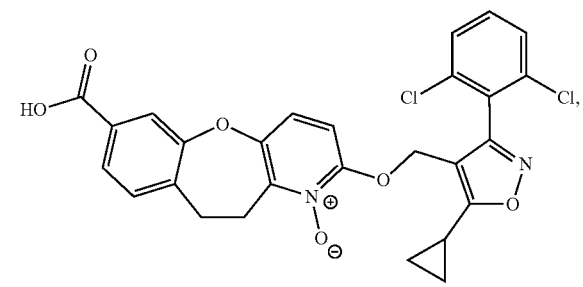

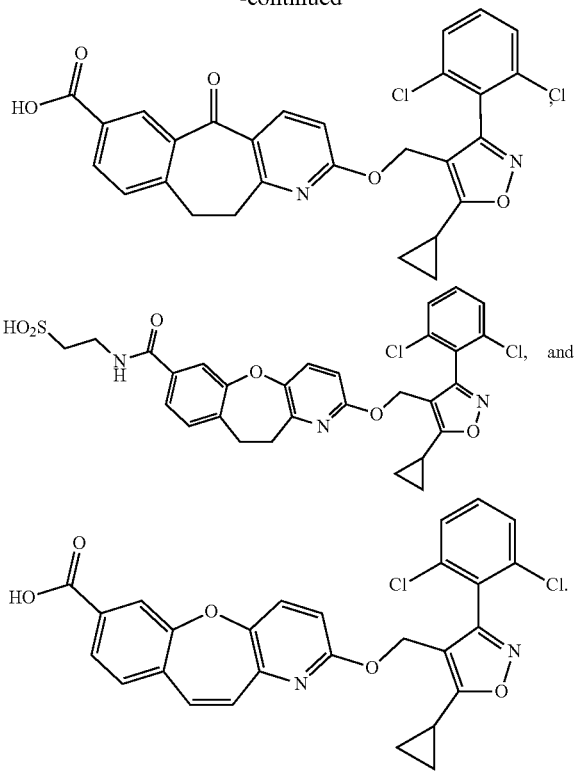

2. The compound of claim 1, wherein each $R^x$ is independently hydrogen, deuterium, $C_{1-6}$ alkyl, $C_{1-6}$ aminoalkyl, $C_{1-6}$ haloalkyl, $C_{3-6}$ cycloalkyl, $C_{2-6}$ heterocyclyl, phenyl, halo-substituted phenyl or benzyl;

each $R^y$ and $R^z$ is independently hydrogen, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{2-6}$ alkenyl, $C_{2-6}$ alkynyl, $C_{3-6}$ cycloalkyl, $C_{2-6}$ heterocyclyl, phenyl, halo-substituted phenyl or benzyl; or $R^y$ and $R^z$ together with the same carbon atom to which they are attached, independently and optionally form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl; and each of $R^h$ and $R^k$ is independently methyl, ethyl, isopropyl or trifluoromethyl; or $R^h$ and $R^k$ together with the carbon atoms to which they are attached, form a $C_{3-6}$ cycloalkane ring or $C_{2-6}$ heterocyclic ring, and wherein the $C_{3-6}$ cycloalkane ring and $C_{2-6}$ heterocyclic ring is independently and optionally substituted with substituents selected from F, Cl, Br, I, hydroxy, amino, nitro, cyano, methyl, ethyl, isopropyl and trifluoromethyl.

3. The compound of claim 1, wherein each $R^x$ is independently hydrogen, deuterium, methyl, ethyl, isopropyl, aminomethyl, difluoromethyl, trifluoromethyl, cyclopropyl, cyclohexyl, tetrahydropyranyl, piperidinyl, phenyl, halo-substituted phenyl or benzyl;

each $R^y$ and $R^z$ is independently hydrogen, deuterium, F, Cl, Br, I, hydroxy, amino, nitro, cyano, methyl, ethyl, n-propyl, isopropyl, difluoromethyl, trifluoromethyl, 2,2-difluoroethyl, 2,2,2-trifluoroethyl, hydroxymethyl, 2-hydroxyethyl, aminomethyl, methoxy, ethoxy, isopropoxy, t-butoxy, methylamino, dimethylamino, vinyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, halo-substituted phenyl or benzyl; or $R^y$ and $R^z$, together with the same carbon atom to which they are attached, independently and optionally form cyclopropane, cyclobutane, cyclopentane, cyclohexane, azetidine, tetrahydrofuran, pyrrolidine, piperidine, piperazine, tetrahydropyran, morpholine or thiomorpholine, and wherein the cyclopropane, cyclobutane, cyclopentane, cyclohexane, azetidine, tetrahydrofuran, pyrrolidine, piperidine, piperazine, tetrahydropyran, morpholine and thiomorpholine is independently and optionally substituted with substituents selected from F, Cl, Br, I, hydroxy, amino, nitro, cyano, methyl, ethyl, isopropyl and trifluoromethyl; and each of $R^h$ and $R^k$ is independently methyl, ethyl, isopropyl or trifluoromethyl; or $R^h$ and $R^k$, together with the carbon atoms to which they are attached, form cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinylene or thiomorpholinylene, and wherein the cyclopropylene, cyclobutylene, cyclopentylene, cyclohexylene, azetidinylene, tetrahydrofuranylene, pyrrolidinylene, piperidinylene, piperazinylene, tetrahydropyranylene, morpholinyl and thiomorpholinyl is independently and optionally substituted with substituents selected from F, Cl, Br, I, hydroxy, amino, nitro, cyano, methyl, ethyl, isopropyl and trifluoromethyl.

4. The compound of claim 1, wherein each $R^1$ is independently hydrogen, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy, $C_{1-6}$ alkoxy-$C_{1-3}$ alkyl, $C_{2-6}$ alkenyl, $C_{2-6}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, -$L^1$-C(=O)OR$^8$, -$L^1$-S(=O)$_t$R$^9$, —O-$L^2$-C(=O)OR$^8$, —O-$L^2$-S(=O)$_t$R$^9$, —C(=O)NR$^{10}$R$^{11}$, —C(=O)N(R$^{10}$)S(=O)$_2$R$^9$, —C(=NR$^{10}$)NR$^{10}$R$^{11}$, —C(=O)N(R$^{10}$)-$L^3$-S(=O)$_2$OR$^8$, —C(=O)N(R$^{10}$)C(=O)OR$^8$ or —C(=O)N(R$^{10}$)-$L^3$-C(=O)OR$^8$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each the $R^1$ is independently and optionally substituted with one or more $R^{12}$;

each $R^8$ is independently hydrogen, deuterium, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl or phenyl;

each $R^9$ is independently hydrogen, deuterium, hydroxy, amino, $C_{1-6}$ alkyl, $C_{1-6}$ aminoalkyl, $C_{2-6}$ alkenyl, $C_{2-6}$ alkynyl, $C_{2-6}$ haloalkyl, $C_{3-6}$ cycloalkyl, $C_{2-6}$ heterocyclyl, phenyl or —NR$^{10}$R$^{11}$;

each $R^{10}$ and $R^{11}$ is independently hydrogen, deuterium, $C_{1-6}$ alkyl, $C_{1-6}$ aminoalkyl, $C_{2-6}$ alkenyl, $C_{2-6}$ alkynyl, $C_{1-6}$ haloalkyl, $C_{3-6}$ cycloalkyl, $C_{2-6}$ heterocyclyl or phenyl; or $R^{10}$ and $R^{11}$, together with the nitrogen atom to which they are attached, independently and optionally form a $C_{2-6}$ heterocyclic ring or $C_{1-5}$ heteroaromatic ring; and each $R^{12}$ is independently hydrogen, deuterium, F, Cl, Br, I, oxo, hydroxy, amino, nitro, cyano, $C_{1-6}$ alkyl, $C_{1-6}$ haloalkyl, $C_{1-6}$ alkoxy, $C_{1-6}$ alkylamino, $C_{2-6}$ alkenyl, $C_{2-6}$ alkynyl, $C_{3-6}$ cycloalkyl, $C_{2-6}$ heterocyclyl, phenyl or $C_{1-5}$ heteroaryl.

5. The compound of claim 1, wherein each $R^1$ is independently hydrogen, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy, $C_{1-3}$ alkoxy-$C_{1-3}$ alkyl, $C_{2-4}$ alkenyl, $C_{2-4}$ alkynyl, $C_{3-6}$ cycloalkyl, $C_{3-6}$ cycloalkoxy, $C_{3-6}$ cycloalkyl-$C_{1-3}$ alkyl, $C_{2-6}$ heterocyclyl, $C_{2-6}$ heterocyclyl-$C_{1-3}$ alkyl, phenyl, halo-substituted phenyl, benzyl, $C_{1-5}$ heteroaryl, -$L^1$-C(=O)O$R^8$, -$L^1$-S(=O)$_r R^9$, —O-$L^2$-C(=O)O$R^8$, —O-$L^2$-S(=O)$_r R^9$, —C(=O)N$R^{10}R^{11}$, —C(=O)N($R^{10}$)S(=O)$_2 R^9$, —C(=N$R^{10}$)N$R^{10}R^{11}$, —C(=O)N($R^{10}$)-$L^3$-S(=O)$_2 OR^8$, —C(=O)N($R^{10}$)C(=O)O$R^8$ or —C(=O)N($R^{10}$)-$L^3$-C(=O)O$R^8$; or two adjacent $R^1$, together with the ring atoms to which they are attached, independently and optionally form a $C_{3-6}$ carbocyclic ring, $C_{2-6}$ heterocyclic ring, benzene ring or $C_{1-5}$ heteroaromatic ring, and wherein each $R^1$ is independently and optionally substituted with one or more $R^{12}$;

each $R^8$ is independently hydrogen, deuterium, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl or phenyl;

each $R^9$ is independently hydrogen, deuterium, hydroxy, amino, $C_{1-3}$ alkyl, $C_{1-3}$ aminoalkyl, $C_{2-4}$ alkenyl, $C_{2-4}$ alkynyl, $C_{2-4}$ haloalkyl, $C_{3-6}$ cycloalkyl, $C_{2-6}$ heterocyclyl, phenyl or —N$R^{10}R^{11}$;

each $R^{10}$ and $R^{11}$ is independently hydrogen, deuterium, $C_{1-3}$ alkyl, $C_{1-3}$ aminoalkyl, $C_{2-4}$ alkenyl, $C_{2-4}$ alkynyl, $C_{1-3}$ haloalkyl, $C_{3-6}$ cycloalkyl, $C_{2-6}$ heterocyclyl or phenyl; or $R^{10}$ and $R^{11}$, together with the nitrogen atom to which they are attached, independently and optionally form a $C_{2-6}$ heterocyclic ring or $C_{1-5}$ heteroaromatic ring; and each $R^{12}$ is independently hydrogen, deuterium, F, Cl, Br, I, oxo, hydroxy, amino, nitro, cyano, $C_{1-3}$ alkyl, $C_{1-3}$ haloalkyl, $C_{1-3}$ alkoxy, $C_{1-3}$ alkylamino, $C_{2-4}$ alkenyl, $C_{2-4}$ alkynyl, $C_{3-6}$ cycloalkyl, $C_{2-6}$ heterocyclyl, phenyl or $C_{1-5}$ heteroaryl.

6. The compound of claim 1, wherein each $R^1$ is independently hydrogen, deuterium, F, Cl, Br, I, hydroxy, amino, nitro, cyano, methyl, ethyl, n-propyl, isopropyl, difluoromethyl, trifluoromethyl, difluoromethoxy, trifluoromethoxy, hydroxymethyl, aminomethyl, methylamino, dimethylamino, methoxylmethyl, isopropoxylmethyl, ethenyl, ethynyl, cyclopropyl, cyclobutyl, cyclopentyl, cyclohexyl, azetidinyl, tetrahydrofuranyl, pyrrolidinyl, piperidinyl, piperazinyl, tetrahydropyranyl, morpholinyl, thiomorpholinyl, phenyl, thiazolyl, thienyl, oxazolyl, triazolyl, tetrazolyl, pyridinyl, pyrimidinyl, —COOH, —C(=O)O—$C_{1-3}$ alkyl, —C(=O)NHS(=O)$_2$—$C_{1-3}$ alkyl, —C(=O)NHS(=O)$_2$-phenyl, —C(=O)NH—$C_{1-3}$ alkylene-S(=O)$_2$OH, —C(=O)NH—$C_{1-3}$ alkylene-C(=O)OH, —S(=O)$_2$NH$_2$, —S(=O)$_2$OH, —S(=O)$_2$—$C_{1-3}$ alkyl, —C(=O)NH$_2$ or —C(=O)N(CH$_3$)$_2$; wherein each $R^1$ is independently and optionally substituted with one or more $R^{12}$; and each $R^{12}$ is independently hydrogen, deuterium, F, Cl, Br, I, oxo, hydroxy, amino, nitro, cyano, methyl, trifluoromethyl, methoxy, methylamino, vinyl, ethynyl, cyclopropyl, cyclohexyl, tetrahydrofuranyl, piperazinyl, phenyl or pyridinyl.

7. The compound of claim 1, wherein each $R^2$, $R^3$, $R^4$, $R^5$ and $R^6$ is independently hydrogen, deuterium, F, Cl, Br, I, hydroxy, amino, nitro, cyano, methyl, isopropyl, difluoromethyl, trifluoromethyl, methoxy, isopropoxy, difluoromethoxy or trifluoromethoxy; and each $R^7$ is independently hydrogen, deuterium, F, Cl, Br, I, hydroxy, amino, nitro, cyano, methyl, ethyl, isopropyl, t-butyl, hydroxymethyl, 2-hydroxyisopropyl, difluoromethyl, trifluoromethyl, 2-fluoroisopropyl, methoxy, isopropoxy, t-butoxy, dimethylamino, isopropoxymethyl, t-butoxymethyl, cyclopropyl, cyclobutyl, cyclopentyl, cyclohexyl, tetrahydrofuranyl, pyrrolidinyl, piperidinyl, piperazinyl, morpholinyl or thiomorpholinyl;

wherein said cyclopropyl, cyclobutyl, cyclopentyl, cyclohexyl, tetrahydrofuranyl, pyrrolidinyl, piperidinyl, piperazinyl, morpholinyl and thiomorpholinyl is independently and optionally substituted with substituents selected from F, Cl, Br, I, hydroxyl, amino, nitro and cyano.

8. A compound having one of the following structures:

(1)

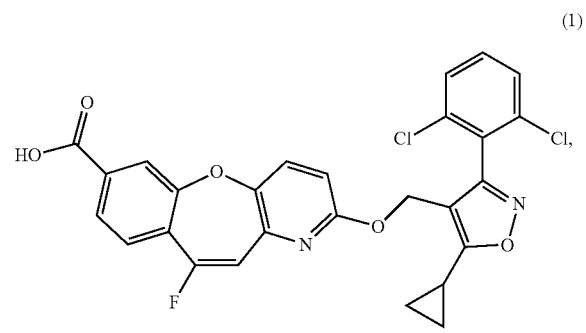

(2)

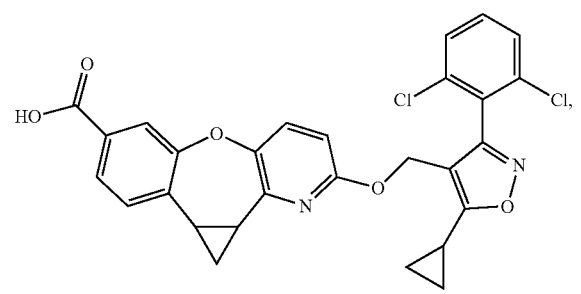

(3)

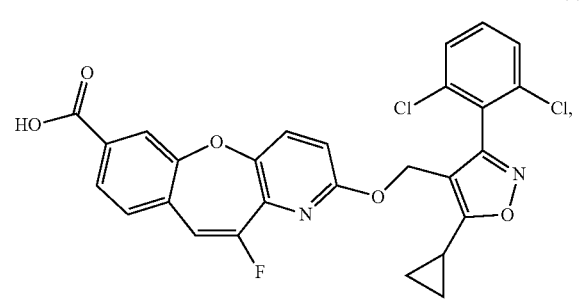

-continued

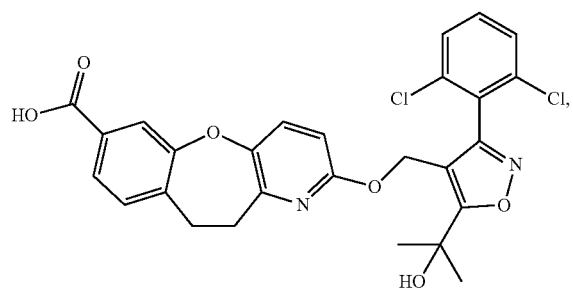
(14)
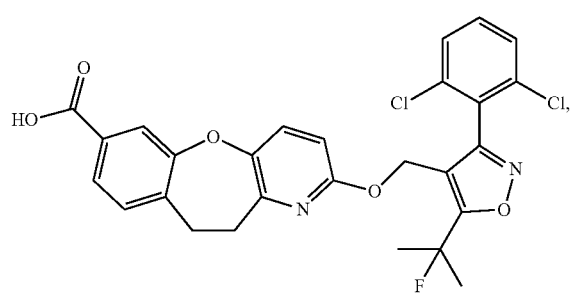
(15)
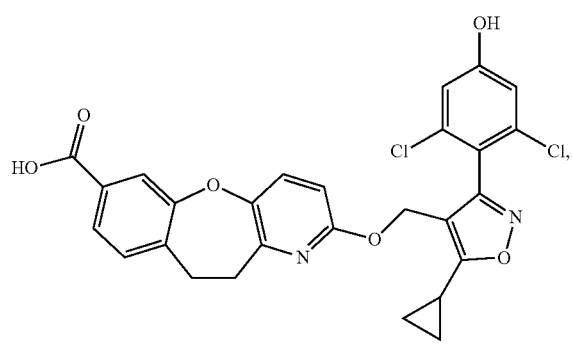
(16)
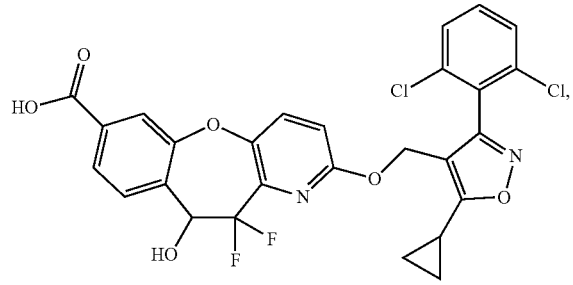
(17)
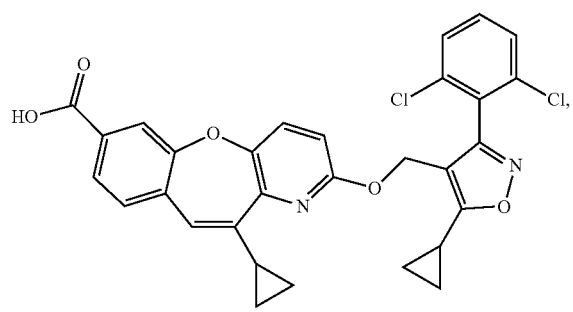
(18)
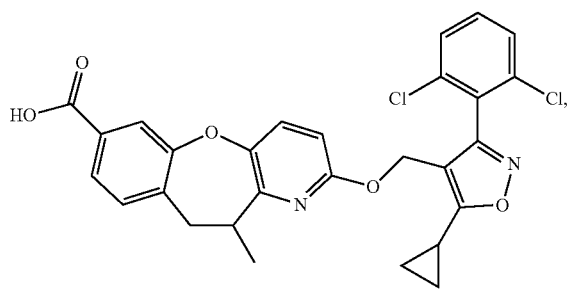
(19)
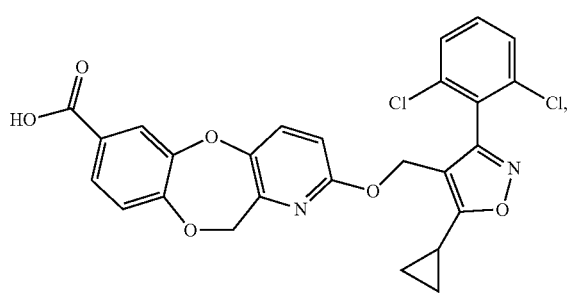
(20)
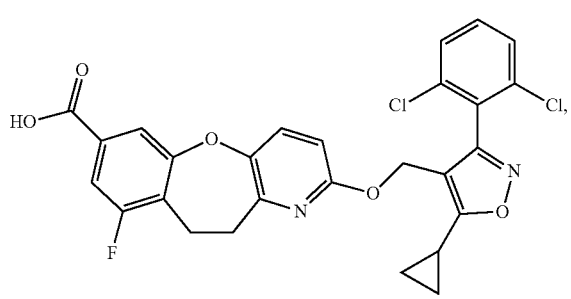
(21)
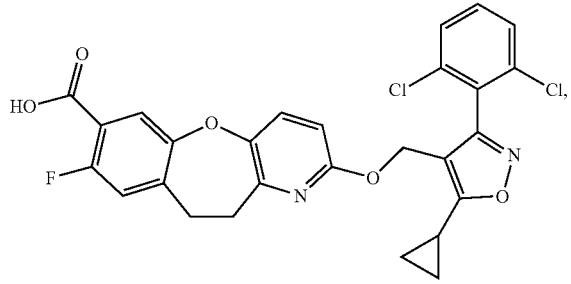
(22)
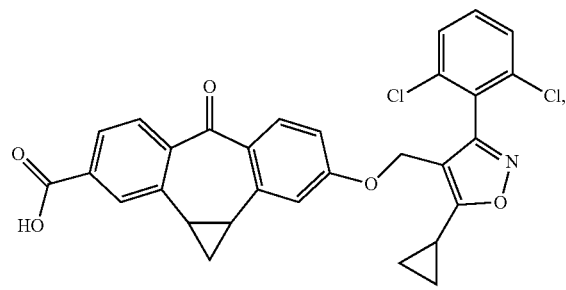
(23)

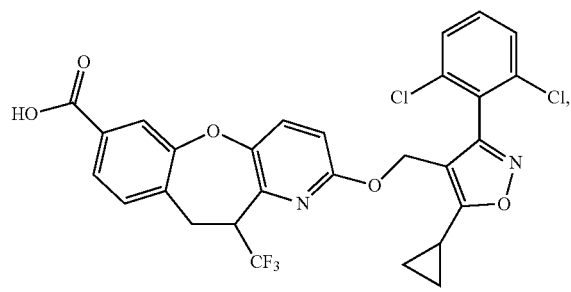 (24)
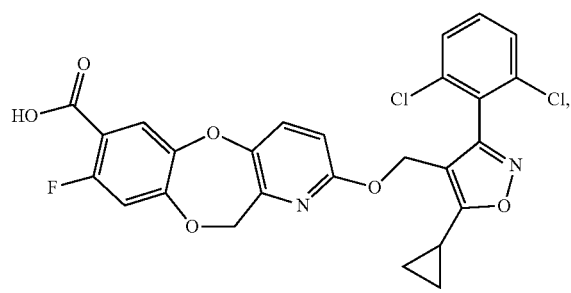 (25)
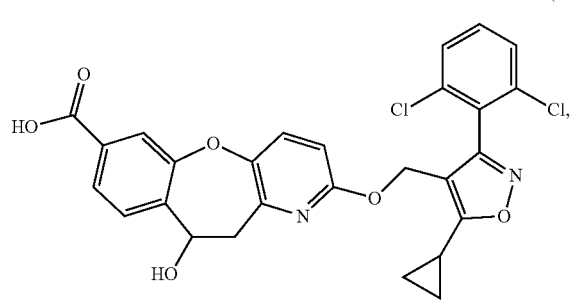 (26)
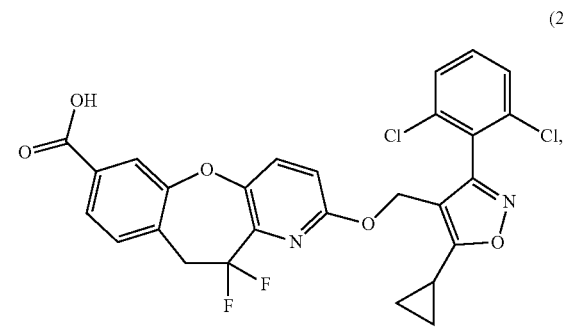 (27)
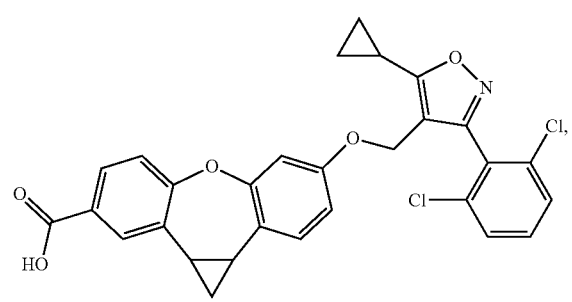 (28)
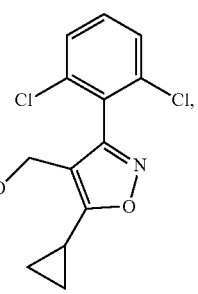 (29)
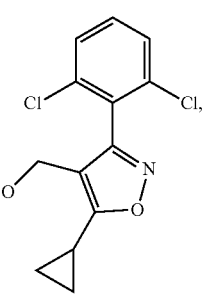 (30)
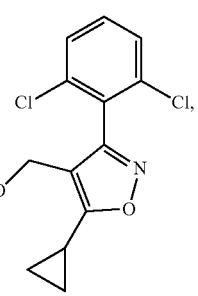 (31)
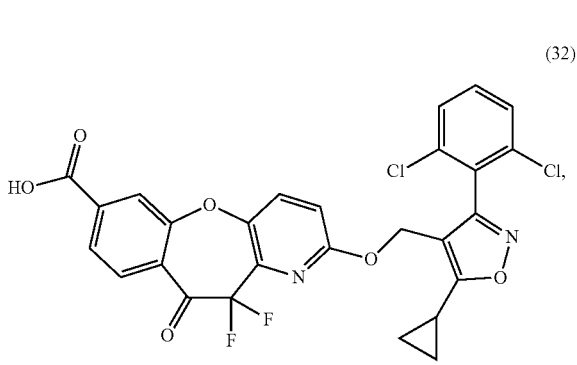 (32)
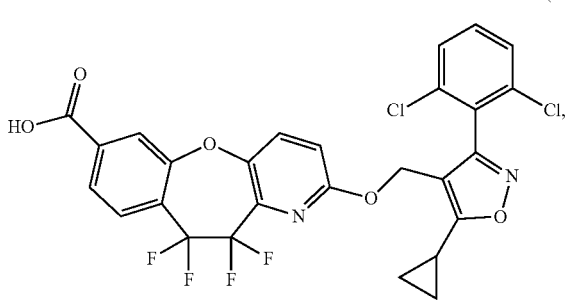 (33)

(34)
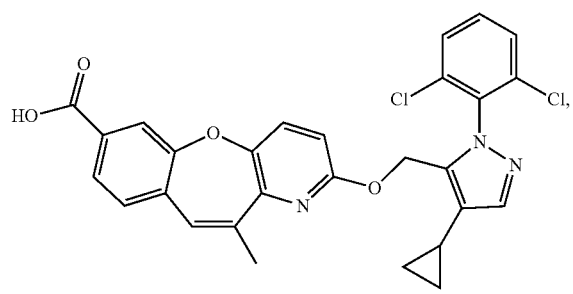
(35)
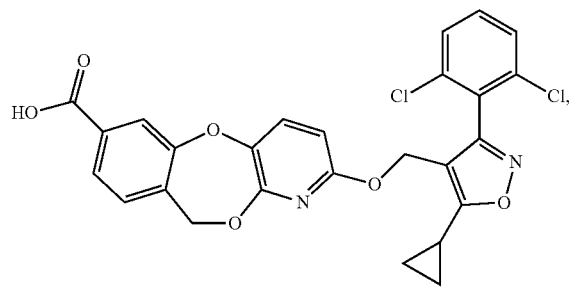
(36)
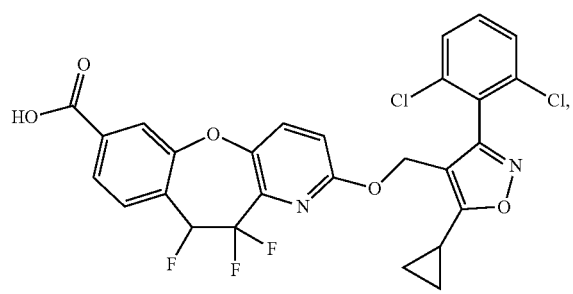
(37)
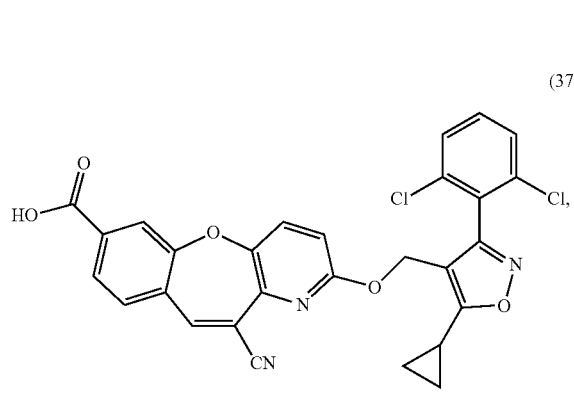
(38)
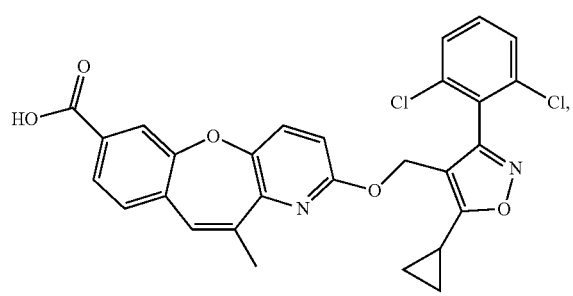
(39)
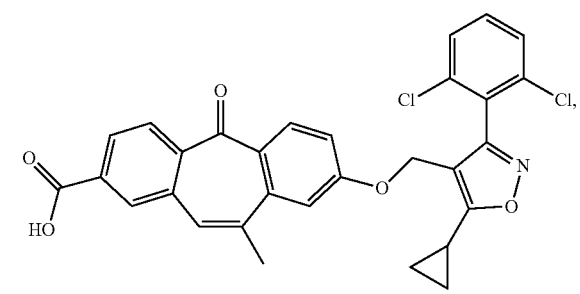
(40)
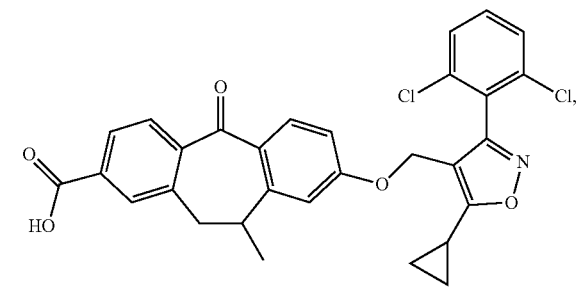
(41)
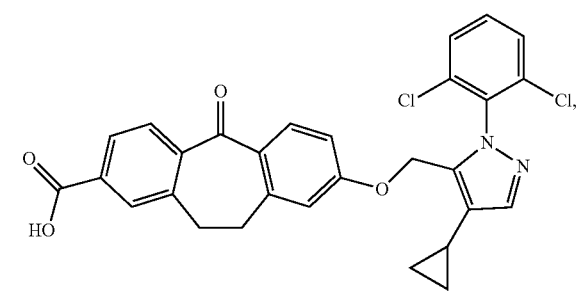
(42)
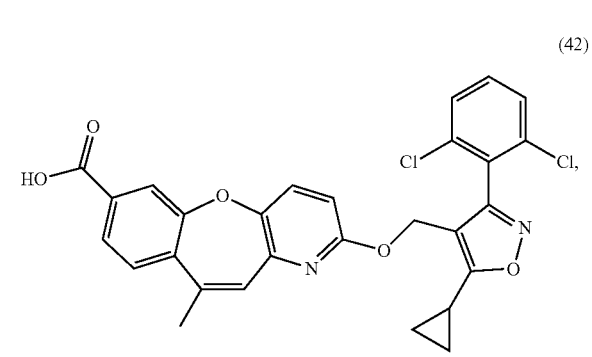
(43)
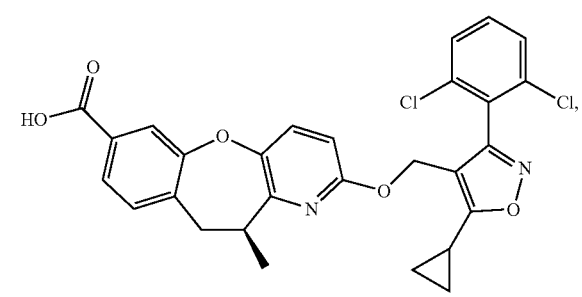

-continued
(44)
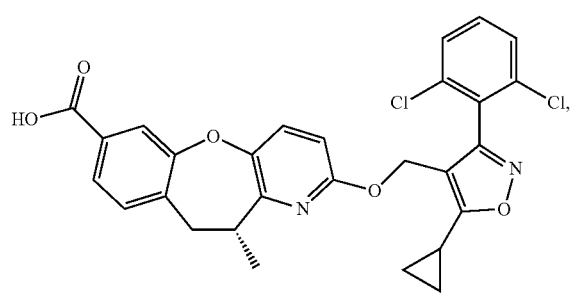
(45)
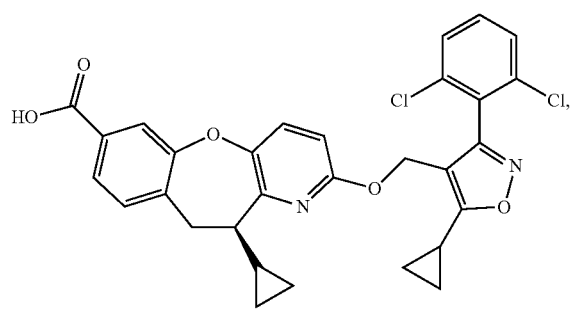
(46)
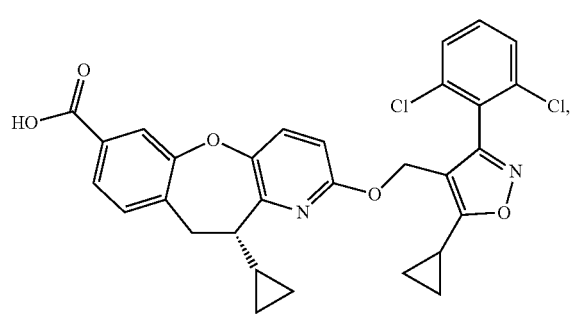
(47)
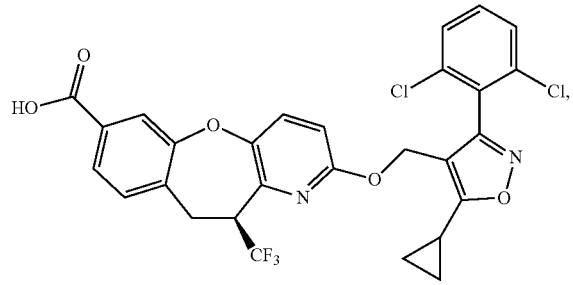
(48)
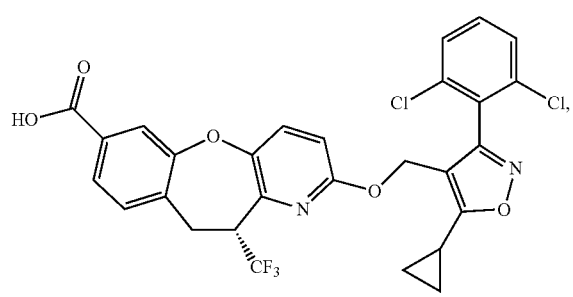
-continued
(49)
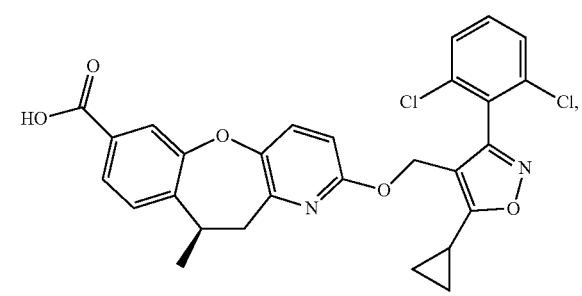
(50)
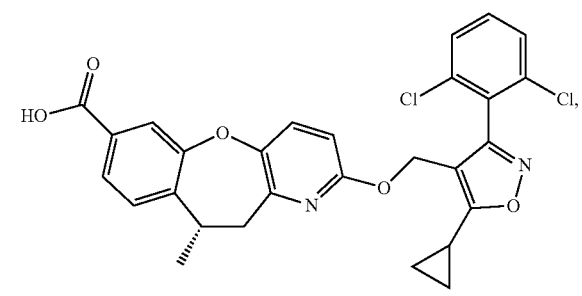
(51)
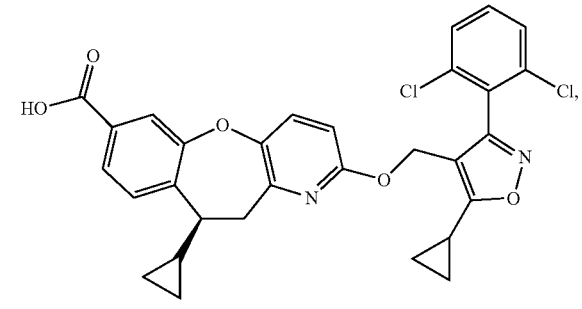
(52)
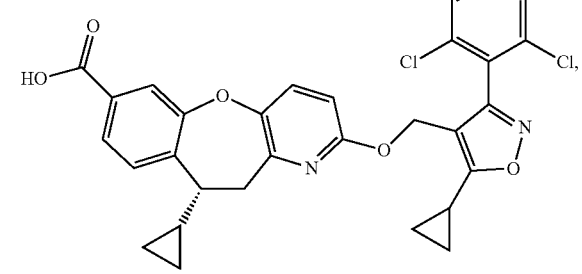
(53)

(54)

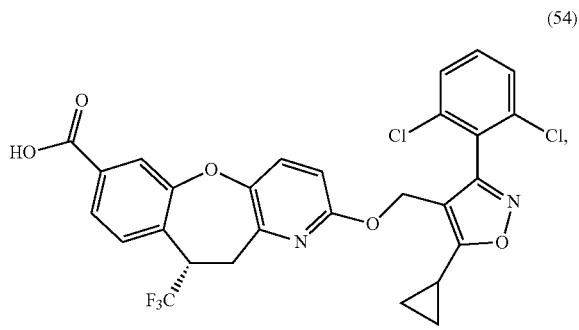

(55)

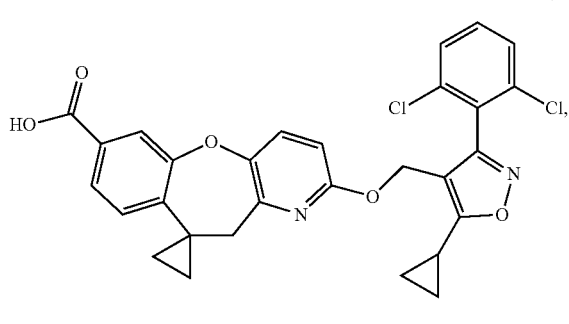

(56)

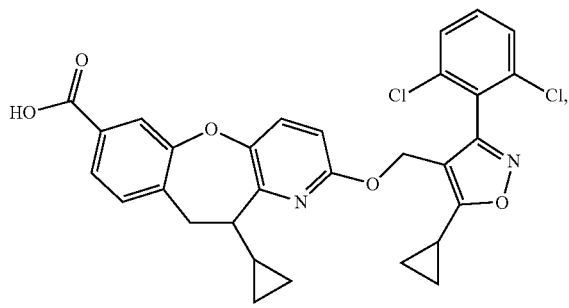

(57)

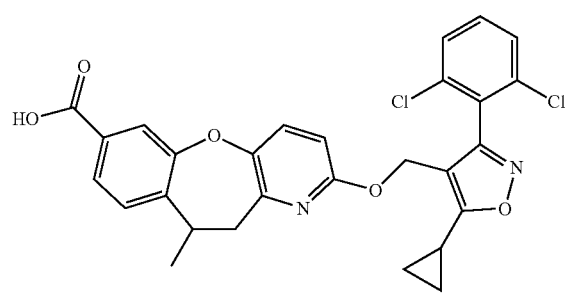

or a stereoisomer, a geometric isomer, a tautomer, an N-oxide, a hydrate, a solvate, or a pharmaceutically acceptable salt thereof.

9. A pharmaceutical composition comprising the compound of claim 1, wherein the pharmaceutical composition optionally further comprises a pharmaceutically acceptable carrier, excipient, diluent, adjuvant, vehicle, or a combination thereof.

10. A method of managing, treating or lessening a disease mediated by FXR in a patient comprising administering to the patient a therapeutic effective amount of the compound of claim 1, wherein the disease mediated by FXR is obesity, metabolic syndrome, insulin resistance, hyperglycemia, hyperinsulinemia, elevated blood level of fatty acid or glycerol, hyperlipidemia, hypertriglyceridemia, hypercholesterolemia, X syndrome, atherosclerosis, hypertension, acute anemia, neutropenia, dyslipidemia, type II diabetes, diabetic nephropathy, diabetic retinopathy, acute myocardial infarction, veno-occlusive disease, heart failure, peripheral aterial occlusive diseases, sexual dysfunction, stroke or thrombosis.

11. A method of managing, treating or lessening a disease mediated by FXR in a patient comprising administering to the patient a therapeutic effective amount of the pharmaceutical composition of claim 9, wherein the disease mediated by FXR is obesity, metabolic syndrome, insulin resistance, hyperglycemia, hyperinsulinemia, elevated blood level of fatty acid or glycerol, hyperlipidemia, hypertriglyceridemia, hypercholesterolemia, X syndrome, atherosclerosis, hypertension, acute anemia, neutropenia, dyslipidemia, type II diabetes, diabetic nephropathy, diabetic retinopathy, acute myocardial infarction, veno-occlusive disease, heart failure, peripheral aterial occlusive diseases, sexual dysfunction, stroke or thrombosis.

* * * * *